(12) United States Patent
Frazier et al.

(10) Patent No.: US 10,676,524 B2
(45) Date of Patent: *Jun. 9, 2020

(54) THERAPEUTIC CD47 ANTIBODIES

(71) Applicant: Arch Oncology, Inc., St. Louis, MO (US)

(72) Inventors: William A. Frazier, St. Louis, MO (US); Pamela T. Manning, Chesterfield, MO (US); Gerhard Frey, St. Louis, MO (US); Hwai Wen Chang, St. Louis, MO (US)

(73) Assignee: Arch Oncology, Inc., St. Louis, MO (US)

( * ) Notice: Subject to any disclaimer, the term of this patent is extended or adjusted under 35 U.S.C. 154(b) by 149 days.

This patent is subject to a terminal disclaimer.

(21) Appl. No.: 15/723,534

(22) Filed: Oct. 3, 2017

(65) Prior Publication Data

US 2018/0057592 A1 Mar. 1, 2018

Related U.S. Application Data

(63) Continuation of application No. 14/302,348, filed on Jun. 11, 2014, now abandoned, which is a continuation-in-part of application No. PCT/US2013/074766, filed on Dec. 12, 2013.

(60) Provisional application No. 61/833,691, filed on Jun. 11, 2013, provisional application No. 61/736,301, filed on Dec. 12, 2012.

(51) Int. Cl.
   *C07K 16/28* (2006.01)
   *A61K 39/00* (2006.01)

(52) U.S. Cl.
   CPC ...... *C07K 16/2803* (2013.01); *C07K 16/2896* (2013.01); *A61K 2039/505* (2013.01); *C07K 2317/24* (2013.01); *C07K 2317/33* (2013.01); *C07K 2317/71* (2013.01); *C07K 2317/73* (2013.01); *C07K 2317/75* (2013.01); *C07K 2317/76* (2013.01); *C07K 2317/92* (2013.01)

(58) Field of Classification Search
   CPC ............ C07K 16/2803; C07K 16/2896; C07K 16/00-468
   See application file for complete search history.

(56) References Cited

U.S. PATENT DOCUMENTS

| | | | |
|---|---|---|---|
| 6,261,839 B1 | 7/2001 | Multhoff | |
| 7,514,229 B2 | 4/2009 | Jamieson | |
| 7,531,643 B2 | 5/2009 | Fukushima | |
| 7,696,325 B2 | 4/2010 | Fukushima | |
| 8,101,719 B2 | 1/2012 | Kikuchi | |
| 8,236,313 B2 | 8/2012 | Isenberg | |
| 8,562,997 B2 | 10/2013 | Jaiswal | |
| 8,728,476 B2 | 5/2014 | Van | |
| 8,758,750 B2 | 6/2014 | Weissman | |
| 8,759,495 B2 | 6/2014 | Boghaert | |
| 8,951,527 B2 | 2/2015 | Isenberg | |
| 9,017,675 B2 | 4/2015 | Liu | |
| 9,045,541 B2 | 6/2015 | Eckelman | |
| 9,221,908 B2 | 12/2015 | Frazier | |
| 9,382,320 B2 | 7/2016 | Liu | |
| 9,518,116 B2 | 12/2016 | Frazier | |
| 9,518,117 B2 | 12/2016 | Frazier | |
| 10,239,945 B2 | 3/2019 | Manning | |
| 10,259,873 B2 | 4/2019 | Frazier | |
| 2001/0041670 A1 | 11/2001 | Simantov | |
| 2003/0108546 A1 | 6/2003 | Fukushima | |
| 2004/0213792 A1 | 10/2004 | Clemmons | |
| 2006/0088522 A1 | 4/2006 | Boghaert | |
| 2007/0111238 A1 | 5/2007 | Jamieson | |
| 2010/0173382 A1 | 7/2010 | Boghaert | |
| 2010/0203559 A1 | 8/2010 | Ester | |
| 2011/0117085 A1 | 5/2011 | Rotem-Yehudar | |
| 2011/0177064 A1 | 7/2011 | Whiteman | |
| 2013/0142786 A1 | 6/2013 | Liu | |

(Continued)

FOREIGN PATENT DOCUMENTS

| AU | 2014201010 | 3/2014 |
|---|---|---|
| BY | 6782 C1 | 3/2005 |

(Continued)

OTHER PUBLICATIONS

U.S. Appl. No. 15/345,691; Notice of Allowance, dated Nov. 28, 2018; 18 pages.
U.S. Appl. No. 15/820,054; Notice of Allowance, dated Nov. 7, 2018; 16 pages.
U.S. Appl. No. 15/871,802; Examiner-Initiated Interview Summary dated Oct. 26, 2018; 2 pages.
U.S. Appl. No. 15/871,802; Final Office Action dated Oct. 26, 2018; 32 pages.
U.S. Appl. No. 16/223,009; Application as tiled, dated Dec. 17, 2018; 148 pages.
Chao, M. et al., "Therapeutic Antibody Targeting of CD47 Eliminates Human Acute Lymphoblastic Leukemia", Cancer Res., 71(4):1374-84, (2011).

(Continued)

*Primary Examiner* — Jessica H Roark
(74) *Attorney, Agent, or Firm* — Dennis A. Bennett; Charles H. Rexer, Jr.

(57) ABSTRACT

Provided are monoclonal antibodies and antigen-binding fragments thereof that bind to CD47 of multiple mammalian species, block the binding of SIRPalpha and TSP1 to CD47, promote phagocytosis of susceptible cancer cells, and reverse TSP1 inhibition of nitric oxide signaling, as well as monoclonal antibodies and antigen binding fragments thereof that compete with the former for binding to CD47 and that exhibit similar biological activities. Also provided are combinations of any of the foregoing. Such antibody compounds are variously effective in 1) treating tissue ischemia and ischemia-reperfusion injury (IRI) in the setting of organ preservation and transplantation, pulmonary hypertension, sickle cell disease, myocardial infarction, stroke, and other instances of surgery and/or trauma in which IRI is a component of pathogenesis; 2) in treating autoimmune and inflammatory diseases; and 3) as anti-cancer agents for treating susceptible cancer cells, promoting their phagocytic uptake and clearance.

4 Claims, 9 Drawing Sheets

Specification includes a Sequence Listing.

(56) References Cited

U.S. PATENT DOCUMENTS

| | | |
|---|---|---|
| 2013/0224188 A1 | 8/2013 | Eckelman |
| 2014/0065169 A1 | 3/2014 | Jaiswal |
| 2014/0140989 A1 | 5/2014 | Eckelman |
| 2014/0161799 A1 | 6/2014 | Frazier |
| 2014/0161825 A1 | 6/2014 | Jaiswal |
| 2014/0199308 A1 | 7/2014 | Van |
| 2014/0294765 A1 | 10/2014 | Cojocaru |
| 2014/0363442 A1 | 12/2014 | Frazier |
| 2014/0369924 A1 | 12/2014 | Weissman |
| 2015/0030600 A1 | 1/2015 | Marks |
| 2015/0274826 A1 | 10/2015 | Frazier |
| 2016/0130336 A1 | 5/2016 | Lai |
| 2016/0137733 A1 | 5/2016 | Frazier |
| 2016/0137734 A1 | 5/2016 | Frazier |
| 2016/0289326 A1 | 10/2016 | Chao |
| 2017/0151282 A1 | 6/2017 | Discher |
| 2017/0283498 A1 | 10/2017 | Frazier |
| 2018/0051081 A1 | 2/2018 | Frazier |
| 2018/0142019 A1 | 5/2018 | Manning |
| 2018/0171014 A1 | 6/2018 | Manning |
| 2019/0112373 A1 | 4/2019 | Manning |
| 2019/0248892 A1 | 8/2019 | Frazier |
| 2019/0309066 A1 | 10/2019 | Manning |

FOREIGN PATENT DOCUMENTS

| | | |
|---|---|---|
| CN | 103665165 | 3/2014 |
| EP | 0256654 A2 | 2/1988 |
| EP | 1035132 | 9/2000 |
| EP | 1693385 | 8/2006 |
| EP | 2111869 | 10/2009 |
| JP | 2007008895 | 1/2007 |
| WO | 1999012973 | 3/1999 |
| WO | 199940940 | 8/1999 |
| WO | 199940940 A1 | 8/1999 |
| WO | 1999040940 | 8/1999 |
| WO | 200105968 A1 | 1/2001 |
| WO | 2003050295 | 6/2003 |
| WO | 2004096133 A2 | 11/2004 |
| WO | 2008043072 A2 | 4/2008 |
| WO | 2008060785 | 5/2008 |
| WO | 2008060785 A2 | 5/2008 |
| WO | 2009091547 | 7/2009 |
| WO | 2009091601 | 7/2009 |
| WO | 2009131453 A1 | 10/2009 |
| WO | 2011083140 | 7/2011 |
| WO | 2011143624 | 11/2011 |
| WO | 2011143624 A2 | 11/2011 |
| WO | 2013119714 | 8/2013 |
| WO | 2014087248 | 6/2014 |
| WO | 2014093678 | 6/2014 |
| WO | 2014093678 A2 | 6/2014 |
| WO | 2014149477 A1 | 9/2014 |
| WO | 2014093678 A3 | 11/2014 |
| WO | 2014123580 | 10/2015 |
| WO | 2015191861 A1 | 12/2015 |
| WO | 2017049251 A2 | 3/2017 |
| WO | 2018075960 | 4/2018 |
| WO | 2018175790 | 9/2018 |

OTHER PUBLICATIONS

International Application No. PCT/US2017/057716; International Preliminary Report on Patentability, dated Apr. 23, 2019; 16 pages.
Majeti, R. et al., "CD47 is an Adverse Prognostic Factor and Therapeutic Antibody Target on Human Acute Myeloid Leukemia Stem Cells", Cell, 138(2):286-99, (2009).
Akewanlop, et al., "Phagocytosis of Breast Cancer Cells Mediated by Anti-Muc-1 Monoclonal Antibody, DF3, and its Bispecific Antibody", Cancer Research, vol. 61, (May 15, 2001).
Almagro, J. et al., Humanization of antibodies, Frontiers in Bioscience 13, 1619-1633, Jan. 1, 2008.
Almagro, J. et al., Progress and Challenges in the Design and Clinical Development of Antibodies for Cancer Therapy, Front Immunol. Jan. 4, 2018;8:1751.
Baker, Monya, "Cancer and Stem Cells: Beckman Conference", Nature Reports Stem Cells, (Mar. 13, 2008).
Brown, Eric J. et al., "Integrin-Associated Protein (CD47) and it's Ligands", Trends in Cell Biology, 11(3):130-5, (2001).
Cameron, C. et al., "Myxoma Virus M128L is Expressed as a Cell Surface CD47-Like Virulence Factor that Contributes to the Downregulation of Macrophage Activation in Vivo", Virology, vol. 337, pp. 55-67 (2005).
Carter, P., Potent antibody therapeutics by design, Nature Reviews Immunology, vol. 6, 343-357, May 2006.
Chao, et al., "Targeting CD47 Eliminates Human Acute Myeloid Leu-Kemia Stem Cells", May 14, 2008, cited Jan 3, 2017.
Chen, Thomas T. et al., "Expression and Activation of Signal Regulatory Protein Alpha on Astrocytomas", Cancer Research, 64:117-27, (2004).
Cooper, G.M., "The Development and Causes of Cancer", The Cell: A Molecular Approach, (2000), cited Jan 3, 2017.
Finlay WJ etr al., Natural and man-made V-gene repertoires for antibody discovery, Front Immunol. Nov. 15, 2012;3:342.
Galluzzi, Lorenzo, et al, "Immunogenic cell death in cancer and infectious disease," Nature Reviews, Immunology, vol. 17, Feb. 2017.
Head, et al., "Ligation of CD47 Mediates Phosphatidylserine Expression on Erythrocytes and a Concomitant Loss of Viability in Vitro", British Journal of Haematology, 130:788-90, (2005).
Henson, Peter M. et al., "Apoptotic Cell Removal", Current Biology, 11:R795-R805, (2011).
Humana Press Inc., "Handbook of Cancer Vaccines", Humana Press Inc., 2004.
International Search Report and Written Opinion of the International Searching Authority for PCT/2017/057716 dated Feb. 21, 2018.
Isenberg, Jeff et al., "Differential Interactions of Thrombospondin-1, -2 and -4 with CD47 and Effects on cGMP Signaling and Ischemic Injury Response", The Journal of Biological Chemistry, vol. 284, No. 2, (Jan. 9, 2009).
Jamieson, Catriona et al., "Increased Expression of CD47 is a Constant Marker in Mouse and Human Myeloid Leukemias", Blood, vol. 106, (2005).
Kim, Min Jung et al., "Association of CD47 with Natural Killer Cell-Mediated Cytotoxicty of Head-and-Neck Squamous Cell Carcinoma Lines", Tumor Biology, 29:28-34, (2008).
Kroemer, G. et al., "Classificatio of Cell Death", Cell Death Difference, 16(1):3-11, (Jan. 2009).
L'Esperance, Sylvain et al., "Gene Expression Profiling of Paired Ovarian Tumors Obtained Prior to and Following Adjuvant Chemotherapy: Molecular Signatures of Chemoresistant Tumors", International Journal of Oncology, 29:5-24, (2006).
Majeti, et al., "Acute Myeloid Leukemia—Therapy, Excluding Transplantation", Blood, vol. 112, (Nov. 16, 2008).
Majeti, Ravindra et al., "CD47 is an Independent Prognostic Factor and Therapeutic Antibody Target on Human Acute Myeloid Leukemia Stem Cells", Blood, vol. 112, (2008).
Mughal, Tariq I. et al., "Understanding Leukemias, Lymphomas and Myelomas", Taylor & Francis, pp. 47-48, 53, (2006).
Munn, "Phagocytosis of Tumor Cells by Human Monocytes Cultured in Recombinant Macrophage Colony-Stimulating Factor", J. Exp. Med., vol. 172, (Jul. 1990).
National Cancer Institute, "Cancer Classification", cited Jan. 3, 2017.
Oldenborg, et al., "Role of CD47 in Erythroid Cells and in Autoimmunity", Leukemia & Lymphoma, 45(7):1319-27, (2004).
Olsson, et al., "Platelet Homeostasis is Regulated by Platelet Expression of CD47 Under Normal Conditions and in Passive Immune Thromocytopenia", Blood, 105(9):3577-82, (May 1, 2005).
Pietsch, et al., "Anti-Leukemic Activity and Tolerability of Anti-Human CD47 Monoclonal Antibodies", American Association of Cancer Research Abstract 2470, (Jan. 2017).

(56) References Cited

OTHER PUBLICATIONS

Raetz, Elizabeth A. et al., "Gene Expression Profiling Reveals Intrinsic Differences Between T-cell Acute Lymphoblastic Leukemia and T-cell Lymphoblastic Lymphoma", Pediatr. Bllod Cancer, (47):130-40, (2006).
Reichert, Janice M., "Marketed Therapeutic Antibodies Compendium", mAbs, Lades Bioscience, 4(3):413-5, (2012).
Roitt A. et al., Immunology (Published by "Mir" Publishing House, Moscow, 2000, p. 110-111.
Science Daily, "Scientists Discover New Way to Distinguish Self from Other", cited Jan. 22, 2017.
Sick E et al., CD47 update: a multifaceted actor in the tumour microenvironment of potential therapeutic interest, Br J Pharmacol. Dec. 2012;167(7): pp. 1415-1430.
Singer M. et al., Genes and Genomes (Published by "Mir" Publishing House, Moscow, 1998, vol. 1, p. 63-64.
Sonderegger S et al., Interleukin (IL)11 mediates protein secretion and modification in human extravillous trophoblasts, Hum Reprod. Oct. 2011;26(10):2841-9.
Soto-Pantoja, et al., "Inhibitory Signaling Through Signal Regulatory Protein-A is Not Sufficient to Explain the Antitumor Activities of CD47 Antibodies", PNAS, 109:E2842, (2012).
Strome, Scott et al., "A Mechanistic Perspective of Monoclonal Antibodies in Cancer Therapy Beyond Target-Related Effects", The Oncologist, vol. 12, (2007).
Submissions dated Jul. 21, 2011 filed during prosecution of U.S. Appl. No. 12/321,215, a continuation-in-part of U.S. Appl. No. 11/528,890.
Submissions of James Poole Limited of Dec. 22, 2016 on EP2282772.
Subramanian S. et al., Phylogenetic divergence of CD47 interactions with human signal regulatory protein alpha reveals locus of species specificity. Implications for the binding site, J Biol Chem. Jan. 19, 2007;282(3):1805-1818.
Takizawa, Hitoshi et al., "Macrophage Tolerance: CD47-SIRP-Alpha-Mediated Signals Matter", Nature Immunology, (8):1287-9, (2007).
Trounson, "Stem Cells, Plasticity and Cancer—Uncomfortable Bed Fellows", Development, vol. 131, (2004).
Van Beek, Ellen M. et al., "Signal Regulatory Proteins in the Immune System", J. Immunol., ISSN: 175:7781-7, (Dec. 2005).
Van Den Berg, Timo K. et al., "Innate Immune 'Self' Recognition: A Role for CD47-SIRPa Interactions in Hemotopoietic Stem Transplantation", Trends Immunology, 29(5):203-6, (Apr. 3, 2008).
Vermeer DW et al., Radiation-induced loss of cell surface CD47 enhances immune-mediated clearance mediated clearance of human papillomavirus-positive cancer, Int J Cancer. Jul. 2013;133(1):120-9.
Wang, Hui et al., "Attenuation of Phagocytosis of Xenogeneic Cells by Manipulating CD47", Blood, vol. 109, No. 2, (Jan. 15, 2007).
Weiskopf and Weissman, "Macrophages are Critical Effectors of Antibody Therapies for Cancer", mAbs, vol. 7, No. 2, (2015).
Weiskopf, et al., "Engineered SIRPa Variants as Immunotherapeutic Adjuvants to Anticancer Antibodies", Science, 341:88-91, (Jul. 5, 2013).
Weissman, Irving et al., "The E. Donnell Thomas Lecture; Normal and Neoplastic Stem Cells", Biol. Blood Marrow Transplant, (2008).
Wikipedia, "Cancer Immunotherapy", cited Jan 8, 2017.
Wikipedia, "Monoclonal Antibody", cited Jan 8, 2017.
Yang Y et al., Wogonin induced calreticulin/annexin A1 exposure dictates the immunogenicity of cancer cells in a PERK/AKT dependent manner, PLoS One. 2012;7(12):e50811.
Zhao, et al., "Is Targeting of CD47-SIRPa Enough for Treating Hematopoietic Malignancy", Blood, 119:4333-4, (May 3, 2012).
Zipin-Roitman A et al., CXCL10 promotes invasion-related properties in human colorectal carcinoma cells, Cancer Res. Apr. 1, 2007;67(7):3396-405.
Chao, M. et al., "Anti-CD47 antibody synergizes with rituximab to promote phagocytosis and eradicate non-Hodgkin lymphoma", Cell, 142(5):699-713, (2010).
Cioffi, M. et al., "Inhibition of CD47 Effectively Targets Pancreatic Cancer Stem Cells via Dual Mechanisms", Clinical Cancer Research, 21(10):2325-37, (2015).
Hanahan, D. et al., "The hallmarks of cancer", Cell, 100(1):57-70, (2000).
Johnstone, R. et al., "Apoptosis: A Link between Cancer Genetics and Chemotherapy", Cell, 108:153-64, (2002).
Liu, J. et al., "Pre-Clinical Development of a Humanized Anti-CD47 Antibody with Anti-Cancer Therapeutic Potential", PLoS ONE, 10(9):e0137345, (2015).
McKenzie, S. et al., "Apoptosis evasion: the role of survival pathways in prostate cancer progression and therapeutic resistance.", J. Cell Biochem., 97(1):18-32, (2006).
Weiskopf, K. et al., "CD47-blocking immunotherapies stimulate macrophage-mediated destruction of small-cell lung cancer", J Clin Invest., 126(7):2610-20, (2016).
Written Submission of Opposition to EP2242512 Following Preliminary Opinion on Behalf of James Roger Wilding, (Jun. 27, 2018); 13 pages.
Written Submission of Opposition to EP2242512 Following Preliminary Opinion on Behalf of Opponent Avidity IP Ltd, (Jun. 27, 2018); 29 pages.
Written Submission of Opposition to EP2242512 Following Preliminary Opinion on Behalf of Surface Oncology, Inc., (Jun. 27, 2018); 21 pages.
Written Submission of Opposition to EP2242512 Following Preliminary Opinion on Behalf of the Board of Trustees of the Leland Stanford Junior University, (Jun. 27, 2018); 16 pages.
Written Submission of Opposition to EP2242512 Following Preliminary Opinion on Behalf of Tioma Therapeutics, Inc., (Jun. 27, 2018); 21 pages.
Zhao, X. et al., "CD47-signal regulatory protein-(SIRP) interactions form a barrier for antibody-mediated tumor cell destruction", Proceedings of the National Academy of Sciences, 108(45)18342-7, (2011).
"Chain L, Diels Alder Catalytic Antibody Germline Precursor", Database Protein, NCBIM Genbank Accession No. 1A4J_L, (Oct. 10, 2012).
"Chimeric Anti-Human Type VII Collagen Immunoglobulin G1 [Synthetic Construct]", Database Protein, NCBI, Genbank Accession No. ACN 59874.1, (Nov. 20, 2009).
Abcam anti-CD47 antibody [EPR 4150(2)] ab108415, available at www.abcam.com/cd47-antibody-epr41502-ab108415.html (last visited Jul. 20, 2015).
Ahmed et al., "Targeting Cd47 as an Apoptotic Trigger of Human Lung Carcinoma Tumors", Amer Inst Chem Eng. 2005 mtg abstract #457d.
Avent et al., "Monoclonal antibodies that recognize different membrane proteins that are deficient in Rh null, human erythrocytes", Biochem. J. (1988) 251, 499-505.
Blazar B R et al., CD47 (integrin-associated protein) engagement of dendritic cell and macrophage counterreceptors is required to prevent the clearance of donor lymphohematopoietic cells, Journal Exp. Med., vol. 194, No. 4, Aug. 20, 2001 541-549.
Brown et al., 'Integrin-associated Protein: A 50-kD Plasma Membrane Antigen Physically and Functionally Associated with Integrins', The Journal of Cell Biology, vol. 111, Dec. 1, 1990, pp. 2785-2794.
Campbell et al., 'An Ovarian Tumor Marker with Homology to Vaccinia Virus Contains an IgV-like Region and Multiple Transmembrane Domains', Cancer Research, vol. 52, Oct. 1. 1992, pp. 5416-5420.
Chao MP et al., Anti-CD47 antibody synergizes with Rituximab to promote phagocytosis and eradicate non-Hodgkin lymphoma, Cell 2010 plus supplemental info.
Chao, et al., "The CD47-SIRP alpha Pathway in Cancer Immune Evasion and Potential Therapeutic Implications," Curr Opin Immunol., Apr. 2012; 24(2): 225-232.
Danielsen et al., 'Dysregulation of CD47 and the ligands thrombospondin 1 and 2 in multiple myeloma', British Journal of Haematology, 138, 756-760. (2007).
Edris B et al., Antibody therapy targeting the CD47 protein is effective in a model of aggressive metastatic leiomyosarcoma, PNAS, 2012, 6656-6661.

(56) References Cited

OTHER PUBLICATIONS

Epenetos et al., 'Monoclonal antibodies for imaging and therapy', Br. J. Cancer (1989), 59, 152-155.

Florian et al., 'Evaluation of normal and neoplastic human mast cells for expression of CD172a (SIRP-alpha), CD47, and SHP-1', Journal of Leukocyte Biology vol. 77, Jun. 2005.

Frazier WA et al., Therapeutic CD47 Antibodies, Vasculox Inc., US20140161799A1, Examiner initiated interview summary, dated Aug. 14, 2015.

Frazier WA et al., Therapeutic CD47 Antibodies, Vasculox Inc., US20140161799A1, Notice of Allowance, dated Aug. 14, 2015.

Frazier Wa et al., Therapeutic CD47 Antibodies, Vasculox Inc., WO0140293678A1, International Preliminary Report on Patentability Chapter I, dated Jun. 16, 2015.

Gardai et al., 'Cell-Surface Calreticulin Initiates Clearance of Viable or Apoptotic Cells through trans-Activation of LRP on the Phagocyte', Cell, vol. 123, 321-334, Oct. 21, 2005.

Gresham et al., 'A Novel Member of the Integrin Receptor Family Mediates Arg-Gly-Asp-stimulated Neutrophil Phagocytosis', The Journal of Cell Biology, vol. 108, May 1989, 1935-1943.

Han et al., 'CD47, a Ligand for the Macrophage Fusion Receptor, Participates in Macrophage Multinucleation', The Journal of Biological Chemistry, vol. 275, No. 48, Issue of Dec. 1, pp. 37984-37992, 2000.

International Search Report, PCT Application No. PCT/US2013/074766, dated Oct. 10, 2014, 6 pgs.

Isenberg, J. et al., Treatment of Liver Ischemia/Reperfusion Injury by Limiting Thrombospondin-1/CD47 Signaling, Surgery 144(5), 752-761, 2008.

Jaiswal S et al., CD47 is upregulated on circulating hematopoietic stem cells and leukemia cells to avoid phagocytosis, Jul. 24, 2009, Cell 138, 271-285.

Jiang p. et al., Integrin-associated Protein is a Ligand for the P84 Neural Adhesion Molecule, The Journal of Biological Chemistry, vol. 274, No. 2, Issue of Jan. 8, 1999, pp. 559-562.

Kaiser et al., 'Expression of insulin-like growth factor receptors I and II in normal human lung and in lung cancer', J Cancer Res Clin Oncol (1993) 119:665-668.

Kenemans, P., CA 125 and OA 3 as target antigens for immunodiagnosis and immunotherapy in ovarian cancer, European Journal of Obstetrics & Gynecology and Reproductive Biology, 36 (1990) 221-238.

Kikuchi et al., "A bivalent single-chain Fv fragment against CD47 induces apoptosis for leukemic cells", Biochemical and Biophysical Research Communications 315 (2004) 912-918.

Kikuchi et al., "Apoptosis inducing bivalent single-chain antibody fragments against CD47 showed antitumor potency for multiple myeloma", Leukemia Research 29 (2005) 445-450.

Knapp et al., 'CD Antigens 1989', Blood, vol. 74, No. 4 Sep. 1989: pp. 1448-1450.

Lamy et al., 'CD47 and the 19 kDa Interacting Protein-3 (BNIP3) in T Cell Apoptosis', The Journal of Biological Chemistry, vol. 278, No. 26, Issue of Jun. 27, pp. 23915-23921, 2003.

Latour et al., "Bidirectional Negative Regulation of Human T and Dendritic Cells by CD47 and Its Cognate Receptor Signal-Regulator Protein-alpha: Down-Regulation of IL-12 Responsiveness and Inhibition of Dendritic Cell Activation", The Journal of Immunology, 2001, 167: 2547-2554.

Legrand, et al., 'Functional CD47/Signal Regulatory Protein Alpha (SIRP(alpha)) Interaction is Required for Optimal Human T- and Natural Killer-(NK) Cell Homeostasis in Vivo', Proceedings of the National Academy of Sciences, vol. 108, No. 32, 2001, pp. 13224-13229.

Lindberg et al., 'Molecular Cloning of Integrin-associated Protein: An Immunoglobulin Family Member with Multiple Membrane-spanning Domains Implicated in CvB3-dependent Ligand Binding', The Journal of Cell Biology, vol. 123, No. 2, Oct. 1993, 485-496.

Lindberg et al., 'Rh-related Antigen CD47 is the Signal-transducer Integrin-associated Protein', The Journal of Biological Chemistry, vol. 269, No. 3, Issue of Jan. 21, pp. 1567-1570, 1994.

Lindberg F P et al., Decreased resistance to bacterial infection and granulocyte defects in IAP-deficient mice, Science New Series, vol. 274, No. 5288 (Nov. 1, 1996), pp. 795-798.

Liu et al., 'Signal Regulatory Protein (SIRP-alpha), a Cellular Ligand for CD47, Regulates Neutrophil Transmigration', The Journal of Biological Chemistry, vol. 277, No. 12, Issue of Mar. 22, pp. 10028-10036, 2002.

Liu, A. 'Differential Expression of Cell Surface Molecules in Prostate Cancer Cells', Cancer Research 60, 3429-3434, Jul. 1, 2000.

Majeti R et al., CD47 is an adverse prognostic factor and therapeutic antibody target on human acute myeloid leukemia stem cells, Cell 2009, 138, p. 286-299.

Majeti, "Monoclonal antibody therapy directed against human acute myeloid leukemia stem cells.", Oncogene, (Nov. 15, 2010), vol. 30, No. 9, pp. 1009-1019, XP055094665.

Manna et al, 'The Mechanism of CD47-Dependent Killing of T Cells: Heterotrimeric Gi-Dependent Inhibition of Protein Kinase A', The Journal of Immunology, (Apr. 1, 2003), vol. 170, No. 7, doi:10.4049/jimmunol.170.7.3544, Issn 0022-1767, pp. 3544-3553, XP055116597.

Manna et al., 'CD47 Mediates Killing of Breast Tumor Cells via Gi-Dependent Inhibition of Protein Kinase A', Cancer Research 64, 1026-1036, Feb. 1, 2004.

Mateo et al., 'CD47 ligation induces caspase-independent cell death in chronic lymphocytic leukemia', Nature Medicine, vol. 5, No. 11, Nov. 1999, pp. 1277-1284.

Mawby et al., "Isolation and characterization of CD47 glycoprotein: a multispanning membrane protein which is the same as integrin-associated protein (IAP) and the ovarian tumour marker OA3", Biochem. J. (1994) 304, 525-530.

Motegi et al., "Role of CD47-SHPS-1 system in regulation of cell migration", The EMBO Journal vol. 22, No. 11, pp. 2634-2644, 2003.

Nishiyama et al., 'Overexpression of Integrin-associated Protein (CD47) in Rat Kidney Treated with a Renal Carcinogen, Ferric Nitrilotriacetate', Jpn. J. Cancer Res. 88, 120-128, Feb. 1997.

Obeid M et al., Ecto-calreticulin in immunogenic chemotherapy, Immunological Reviews 2007, vol. 220: 22-34.

Oldenborg PA et al., CD47-signal regulatory protein alpha (SIRPa) regulates Fcgamma and complement receptor-mediated phagocytosis, Journal Exp Med, vol. 193, No. 7, Apr. 2, 2001 p. 855-861.

Per-Arne Oldenborg et al., 'Role of CD47 as a Marker of Self on Red Blood Cells', Science vol. 288, Jun. 16, 2000, pp. 2051-2054.

Pettersen et al., 'CD99 Signals Caspase-Independent T Cell Death', The Journal of Immunology, 2001, 166: 4931-4942.

Pettersen et al., "CD47 Signals T Cell Death", The Journal of Immunology, 1999, 162: 7031-7040.

Poets et al., "Monoclonal Antibody Against Human Ovarian Tumor-Associated Antigens", JNCI, vol. 76, 1986, 781-791.

Rebres et al., "Novel CD47-Dependent Intercellular Adhesion Modulates Cell Migration", Journal of Cellular Physiology, 205:182-193 (2005).

Roberts, D. et al., The Matricellular Protein Thrombospondin-1 Globally Regulates Cardiovascular Function and Responses to Stress via CD47, Matrix Biology 31(3), 162-169, 2012.

Sagawa et al., 'A new disulfide-linked dimer of a single-chain antibody fragment against human CD47 induces apoptosis in lymphoid malignant cells via the hypoxia inducible factor-1 alpha pathway', Cancer Sci, Jun. 2011, vol. 102, No. 6, 1208-1215.

Samani et al., 'The Role of the IGF System in Cancer Growth and Metastasis: Overview and Recent Insights', Endocrine Reviews 28(1):20-47, (2007).

Seiffert et al., 'Human Signal-Regulatory Protein is Expressed on Normal, But Not on Subsets of Leukemic Myeloid Cells and Mediates Cellular Adhesion Involving Its Counterreceptor CD47' Blood, vol. 94, No. 11 Dec. 1, 1999: pp. 3633-3643.

Subramanian et al., 'Species- and cell type-specific interactions between CD47 and human SIRP-alpha', Blood, Mar. 15, 2006, vol. 107, No. 6.

(56) References Cited

OTHER PUBLICATIONS

Tamoto et al., 'Gene-Expression Profile Changes Correlated with Tumor Progression and Lymph Node Metastasis in Esophageal Cancer', Clinical Cancer Research, vol. 10, 3629-3638, Jun. 1, 2004.
Ticchioni et al., "Integrin-Associated Protein (CD47) is a Comitogenic Molecule on CD3-Activated Human T Cells", The Journal of Immunology, 1997, 158: 677-684.
Uno et al., "Antitumor activity of a monoclonal antibody against CD47 in xenograft models of human leukemia", Oncology Reports 17: 1189-1194, 2007.
US20140161799A1, Examiner Initiated Interview Summary, dated Aug. 14, 2015, 1 page.
Van Ravenswaay Claasen et al., "Analysis of Production, Purification, and Cytolytic Potential of Bi-Specific Antibodies Reactive With Ovarian-Carcinoma-Associated Antigens and the T-Cell Antigen CD3", Int. J. Cancer: 55, 128-136 (1993).
Vernon-Wilson et al., 'CD47 is a ligand for rat macrophage membrane signal regulatory protein SIRP (OX41) and human Sirp alpha 1', Eur. J. Immunol. 2000. 30: 2130-2137.
Willingham S B et al., The CD47-signal regulatory protein alpha (SIRPa) interaction is a therapeutic target for human solid tumors, PNAS, Apr. 24, 2012, vol. 109, No. 17, p. 6662-6667.
WO2015191861, International Search Report and Written Opinion, dated Oct. 15, 2015, 6 pages.
Yamao T et al., Negative regulation of platelet clearance and of the macrophage phagocytic response by the transmembrane glycoprotein SHPS-1, Journal of Biological Chemistry, vol. 277, No. 42, Issue of Oct. 18, 2002, pp. 39833-39839.
Zhan et al., 'Global gene expression profiling of multiple myeloma, monoclonal gammopathy of undetermined significance, and normal bone marrow plasma cells', Blood, Mar. 1, 2002, z vol. 99, No. 5.
International Application No. PCT/US2013/074766; International Preliminary Report on Patentability, dated Jun. 16, 2015; 08 pages.
International Application No. PCT/US2015/035345; International Preliminary Report on Patentability, dated Dec. 15, 2016; 04 pages.
International Application No. PCT/US2015/035345; International Search Report and Written Opinion of the International Search Authority; dated Oct. 15, 2015; 06 pages.
International Application No. PCT/US2016/052383; International Preliminary Report on Patentability, dated Mar. 20, 2018; 11 pages.
International Application No. PCT/US2016/052383; International Search Report and Written Opinion of the International Search Authority, dated Mar. 1, 2017; 16 pages.
International Application No. PCT/US2017/057716; International Search Report and Written Opinion of the International Search Authority, dated Feb. 21, 2018; 22 pages.
U.S. Appl. No. 14/104,007; Examiner Initiated Interview Summary dated Aug. 14, 2015; 01 page.
U.S. Appl. No. 14/104,007; Notice of Allowance dated Aug. 14, 2015; 14 pages.
U.S. Appl. No. 14/302,348; Affidavit-traversing rejections or objections rule 132 dated Feb. 1, 2017; 17 pages.
U.S. Appl. No. 14/302,348; Final Office Action dated Mar. 13, 2017; 11 pages.
U.S. Appl. No. 14/302,348; Non-Final Office Action dated Aug. 1, 2016; 15 pages.
U.S. Appl. No. 14/302,348; Notice of Allowance dated Oct. 6, 2017; 02 pages.
U.S. Appl. No. 14/302,348; Notice of Allowance dated Sep. 27, 2017; 05 pages.
U.S. Appl. No. 14/737,053; Affidavit-traversing rejections or objections rule 132 dated Feb. 2, 2017; 17 pages.
U.S. Appl. No. 14/737,053; Final Office Action dated Mar. 14, 2017; 11 pages.
U.S. Appl. No. 14/737,053; Non-Final Office Action dated Aug. 2, 2016; 15 pages.
U.S. Appl. No. 14/737,053; Notice of Allowance dated Sep. 25, 2017; 05 pages.
U.S. Appl. No. 14/940,751; Notice of Allowance dated Aug. 4, 2016; 10 pages.
U.S. Appl. No. 14/940,755; Notice of Allowance dated Aug. 4, 2016; 10 pages.
U.S. Appl. No. 15/345,691; Non-Final Office Action dated Dec. 6, 2017; 16 pages.
U.S. Appl. No. 15/820,054, filed Nov. 21, 2017; 106 pages.
U.S. Appl. No. 15/871,802, filed Jan. 15, 2018; 170 pages.
U.S. Appl. No. 15/871,802; Non-Final Office Action dated Mar. 1, 2018; 15 pages.
Giusti, A. et al., "Somatic Diversification of S107 from an Antiphosphocholine to an Anti-DNA Autoantibody is Due to a Single Base Change in its Heavy Chain Variable Region", Proc Natl Acad Sci USA., 84(9):2926-30, (1987).
Mariuzza, R. et al., "The Structural Basis of Antigen-Antibody Recognition", Annu Rev Biophys Biophys Chem., 16:139-59, (1987).
Rudikoff, S. et al., "Single Amino Acid Substitution Altering Antigen-Binding Specificity", Proc Natl Acad Sci U S A, 79(6):1979-83, (1982).
U.S. Appl. No. 15/345,691; Final Office Action dated Jul. 12, 2018; 14 pages.
U.S. Appl. No. 15/820,054; Non-Final Office Action dated Jul. 20, 2018; 33 pages.
Winkler, K. et al., "Changing the Antigen Binding Specificity by Single Point Mutations of an Anti-p24 (HIV-1) Antibody", J Immunol., 165(8):4505-14, (2000).
U.S. Appl. No. 16/223,009; Non-Final Office Action dated Feb. 8, 2019; 17 pages.
U.S. Appl. No. 16/271,513, filed Feb. 8, 2019; 105 pages.
U.S. Appl. No. 16/288,957, filed Feb. 28, 2019; 63 pages.
Anonymous, "Tumor-Toxic CD47 mAb Therapy for Leukemia: A Proof of Concept Study", retreived online at https://www.sbir.gov/print/sbirsearch/detail/677077 dated Oct. 1, 2017; 3 pages, (2013).
Declaration of Henry Shelton EARP, date of signatory Dec. 21, 2016, with Exhibits HSE-1 and HSE-2; pages.
Declaration of Kristy Richards, date of signatory Dec. 20, 2016, with Exhibit KR-1; 31 pages.
Declaration of Ravindra Majeti, date of signatory Dec. 16, 2016, with exhibits RM-1 to RM-3 (D3, D3a, D3b); 86 pages.
European Patent Application No. 2240780; Register Extract, dated Nov. 26, 2016; 3 pages.
European Patent Application No. 2282772; Register Extract, dated Jan. 25, 2017; 2 pages.
International Application No. PCT/US2009/000319; Assignment Data Extract, dated Nov. 21, 2016; 1 page.
International Application No. PCT/US2009/000319; Patent Assignment Abstract of Title, dated Apr. 20, 2016; 1 page.
International Application No. PCT/US2009/000319; PCT Request form, dated Jan. 15, 2009; 6 pages.
International Application No. PCT/US2018/023860; International Preliminary Report on Patentability, dated Oct. 3, 2019; 10 pages.
International Application No. PCT/US2018/023860; International Search Report and Written Opinion of the International Searching Authority, dated Jun. 20, 2018; 14 pages.
Liu, X. et al., "CD47 Blockade Triggers T Cell-Mediated Destruction of Immunogenic Tumors", Nat Med., 21 (10):1209-15, (2015).
U.S. Appl. No. 15/723,523; Non-Final Office Action, dated Jul. 12, 2019; 53 pages.
U.S. Appl. No. 15/871,802; Non-Final Office Action, dated Jun. 4, 2019; 31 pages.
U.S. Appl. No. 16/223,009; Final Office Action, dated Jun. 4, 2019; 27 pages.
U.S. Appl. No. 16/271,513; Non-Final Office Action, dated Sep. 9, 2019; 28 pages.
U.S. Appl. No. 16/452,432; Application as filed, dated Jun. 25, 2019; 163 pages.
U.S. Appl. No. 61/011,324; Excerpt from the USPTO website regarding Assignments Data, dated Nov. 15, 2016; 1 page.
U.S. Appl. No. 61/189,786; Excerpt from the USPTO website regarding Assignments Data, dated Nov. 15, 2016; 1 page.

SEQUENCE LISTING

```
<160> NUMBER OF SEQ ID NOS: 121

<210> SEQ ID NO 1
<211> LENGTH: 16
<212> TYPE: PRT
<213> ORGANISM: Artificial Sequence
<220> FEATURE:
<223> OTHER INFORMATION: light chain complementarity determining region

<400> SEQUENCE: 1

Arg Ser Ser Gln Ser Leu Val His Ser Asn Gly Asn Thr Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: light chain complementarity determining region

<400> SEQUENCE: 2

Lys Val Ser Tyr Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: light chain complementarity determining region
```

```
<400> SEQUENCE: 3

Ser Gln Asn Thr His Val Pro Arg Thr
1               5

<210> SEQ ID NO 4
<211> LENGTH: 10
<212> TYPE: PRT
<213> ORGANISM: Artificial Sequence
<220> FEATURE:
<223> OTHER INFORMATION: heavy chain complementarity determining region

<400> SEQUENCE: 4

Gly Tyr Thr Phe Thr Asn Tyr Tyr Val Phe
1               5                   10

<210> SEQ ID NO 5
<211> LENGTH: 17
<212> TYPE: PRT
<213> ORGANISM: Artificial Sequence
<220> FEATURE:
<223> OTHER INFORMATION: heavy chain complementarity determining region

<400> SEQUENCE: 5

Asp Ile Asn Pro Val Asn Gly Asp Thr Asn Phe Asn Glu Lys Phe Lys
1               5                   10                  15

Asn

<210> SEQ ID NO 6
<211> LENGTH: 7
<212> TYPE: PRT
<213> ORGANISM: Artificial Sequence
<220> FEATURE:
<223> OTHER INFORMATION: heavy chain complementarity determining region

<400> SEQUENCE: 6

Gly Gly Tyr Thr Met Asp Tyr
1               5

<210> SEQ ID NO 7
<211> LENGTH: 106
<212> TYPE: PRT
<213> ORGANISM: Artificial Sequence
<220> FEATURE:
<223> OTHER INFORMATION: light chain variable region

<400> SEQUENCE: 7

Asp Val Val Met Thr Gln Thr Pro Leu Ser Leu Ser Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Arg Thr Phe Gly Gln Gly
            100                 105

<210> SEQ ID NO 8
```

```
<211> LENGTH: 106
<212> TYPE: PRT
<213> ORGANISM: Artificial Sequence
<220> FEATURE:
<223> OTHER INFORMATION: light chain variable region

<400> SEQUENCE: 8

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 9
<211> LENGTH: 106
<212> TYPE: PRT
<213> ORGANISM: Artificial Sequence
<220> FEATURE:
<223> OTHER INFORMATION: light chain variable region

<400> SEQUENCE: 9

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Arg Thr Phe Gly Gln Gly
            100                 105

<210> SEQ ID NO 10
<211> LENGTH: 106
<212> TYPE: PRT
<213> ORGANISM: Artificial Sequence
<220> FEATURE:
<223> OTHER INFORMATION: light chain variable region

<400> SEQUENCE: 10

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45
```

```
Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105
```

<210> SEQ ID NO 11
<211> LENGTH: 106
<212> TYPE: PRT
<213> ORGANISM: Artificial Sequence
<220> FEATURE:
<223> OTHER INFORMATION: light chain variable region

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Tyr Arg Phe Ser Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
                85                  90                  95

Thr His Val Pro Arg Thr Phe Gly Gln Gly
            100                 105
```

<210> SEQ ID NO 12
<211> LENGTH: 106
<212> TYPE: PRT
<213> ORGANISM: Artificial Sequence
<220> FEATURE:
<223> OTHER INFORMATION: light chain variable region

<400> SEQUENCE: 12

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105
```

<210> SEQ ID NO 13
<211> LENGTH: 106
<212> TYPE: PRT
<213> ORGANISM: Artificial Sequence

```
<220> FEATURE:
<223> OTHER INFORMATION: light chain variable region

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Ile Pro
    50                  55                  60

Ala Arg Phe Ser Gly Ser Gly Ser Gly Thr Glu Phe Thr Leu Thr Ile
65                  70                  75                  80

Ser Ser Leu Gln Ser Glu Asp Phe Ala Val Tyr Tyr Cys Ser Gln Asn
                85                  90                  95

Thr His Val Pro Arg Thr Phe Gly Gln Gly
            100                 105

<210> SEQ ID NO 14
<211> LENGTH: 106
<212> TYPE: PRT
<213> ORGANISM: Artificial Sequence
<220> FEATURE:
<223> OTHER INFORMATION: light chain variable region

<400> SEQUENCE: 14

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 15
<211> LENGTH: 106
<212> TYPE: PRT
<213> ORGANISM: Artificial Sequence
<220> FEATURE:
<223> OTHER INFORMATION: light chain variable region

<400> SEQUENCE: 15

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 16
<211> LENGTH: 106
<212> TYPE: PRT
<213> ORGANISM: Artificial Sequence
<220> FEATURE:
<223> OTHER INFORMATION: light chain variable region

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Val His Ser
            20                  25                  30

Asn Gly Asn Thr Tyr Leu His Trp Tyr Gln Gln Lys Pro Gly Lys Ala
            35                  40                  45

Pro Lys Leu Leu Ile Tyr Lys Val Ser Tyr Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 17
<211> LENGTH: 106
<212> TYPE: PRT
<213> ORGANISM: Artificial Sequence
<220> FEATURE:
<223> OTHER INFORMATION: light chain variable region

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Tyr Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 18
<211> LENGTH: 106
<212> TYPE: PRT
<213> ORGANISM: Artificial Sequence
<220> FEATURE:
<223> OTHER INFORMATION: light chain variable region

```
<400> SEQUENCE: 18

Glu Ile Val Leu Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Glu Ala Glu Asp Ala Ala Thr Tyr Tyr Cys Ser Gln Asn
                85                  90                  95

Thr His Val Pro Arg Thr Phe Gly Gln Gly
            100                 105

<210> SEQ ID NO 19
<211> LENGTH: 106
<212> TYPE: PRT
<213> ORGANISM: Artificial Sequence
<220> FEATURE:
<223> OTHER INFORMATION: light chain variable region

<400> SEQUENCE: 19

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100                 105

<210> SEQ ID NO 20
<211> LENGTH: 106
<212> TYPE: PRT
<213> ORGANISM: Artificial Sequence
<220> FEATURE:
<223> OTHER INFORMATION: light chain variable region

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Ser Gln Asn
             85                  90                  95

Thr His Val Pro Arg Thr Phe Gly Gln Gly
            100                 105

<210> SEQ ID NO 21
<211> LENGTH: 106
<212> TYPE: PRT
<213> ORGANISM: Artificial Sequence
<220> FEATURE:
<223> OTHER INFORMATION: light chain variable region

<400> SEQUENCE: 21

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
             85                  90                  95

Thr His Val Pro Arg Thr Phe Gly Gln Gly
            100                 105

<210> SEQ ID NO 22
<211> LENGTH: 106
<212> TYPE: PRT
<213> ORGANISM: Artificial Sequence
<220> FEATURE:
<223> OTHER INFORMATION: light chain variable region

<400> SEQUENCE: 22

Ala Ile Gln Leu Thr Gln Ser Pro Ser Ser Leu Ser Ala Ser Val Gly
1               5                  10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
             85                  90                  95

Thr His Val Pro Arg Thr Phe Gly Gln Gly
            100                 105

<210> SEQ ID NO 23
<211> LENGTH: 106
<212> TYPE: PRT
<213> ORGANISM: Artificial Sequence
<220> FEATURE:
<223> OTHER INFORMATION: light chain variable region

<400> SEQUENCE: 23

Ala Ile Gln Leu Thr Gln Ser Pro Ser Ser Leu Ser Ala Ser Val Gly
```

```
              1               5                  10                  15
Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
            35                  40                  45

Pro Arg Leu Leu Ile Tyr Lys Val Ser Tyr Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
                100                 105

<210> SEQ ID NO 24
<211> LENGTH: 106
<212> TYPE: PRT
<213> ORGANISM: Artificial Sequence
<220> FEATURE:
<223> OTHER INFORMATION: light chain variable region

<400> SEQUENCE: 24

Ala Ile Gln Leu Thr Gln Ser Pro Ser Ser Leu Ser Ala Ser Val Gly
 1               5                  10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
            35                  40                  45

Pro Arg Leu Leu Ile Tyr Lys Val Ser Tyr Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
                100                 105

<210> SEQ ID NO 25
<211> LENGTH: 106
<212> TYPE: PRT
<213> ORGANISM: Artificial Sequence
<220> FEATURE:
<223> OTHER INFORMATION: light chain variable region

<400> SEQUENCE: 25

Glu Ile Val Leu Thr Gln Ser Pro Ala Thr Leu Ser Val Ser Pro Gly
 1               5                  10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
            35                  40                  45

Pro Arg Leu Leu Ile Tyr Lys Val Ser Tyr Arg Phe Ser Gly Val Pro
            50                  55                  60

Ser Arg Phe Ser Gly Ser Gly Ser Gly Thr Asp Phe Thr Phe Thr Ile
 65                  70                  75                  80

Ser Ser Leu Glu Ala Glu Asp Ala Ala Thr Tyr Tyr Cys Ser Gln Asn
                 85                  90                  95
```

Thr His Val Pro Arg Thr Phe Gly Gln Gly
            100              105

<210> SEQ ID NO 26
<211> LENGTH: 106
<212> TYPE: PRT
<213> ORGANISM: Artificial Sequence
<220> FEATURE:
<223> OTHER INFORMATION: light chain variable region

<400> SEQUENCE: 26

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100             105

<210> SEQ ID NO 27
<211> LENGTH: 106
<212> TYPE: PRT
<213> ORGANISM: Artificial Sequence
<220> FEATURE:
<223> OTHER INFORMATION: light chain variable region

<400> SEQUENCE: 27

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Arg Thr Phe Gly Gln Gly
            100             105

<210> SEQ ID NO 28
<211> LENGTH: 106
<212> TYPE: PRT
<213> ORGANISM: Artificial Sequence
<220> FEATURE:
<223> OTHER INFORMATION: light chain variable region

<400> SEQUENCE: 28

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser

```
                    20                  25                  30

Asn Gly Asn Thr Tyr Leu His Trp Tyr Gln Gln Lys Pro Gly Gln Ala
                35                  40                  45

Pro Arg Leu Leu Ile Tyr Lys Val Ser Tyr Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105

<210> SEQ ID NO 29
<211> LENGTH: 106
<212> TYPE: PRT
<213> ORGANISM: Artificial Sequence
<220> FEATURE:
<223> OTHER INFORMATION: light chain variable region

<400> SEQUENCE: 29

Glu Ile Val Leu Thr Gln Ser Pro Ala Thr Leu Ser Val Ser Pro Gly
 1               5                  10                  15

Glu Arg Ala Thr Leu Ser Cys Arg Ser Gln Ser Leu Val His Ser
                20                  25                  30

Asn Gly Asn Thr Tyr Leu His Trp Tyr Gln Gln Lys Pro Gly Gln Ala
                35                  40                  45

Pro Arg Leu Leu Ile Tyr Lys Val Ser Tyr Arg Phe Ser Gly Val Pro
         50                  55                  60

Ser Arg Phe Ser Gly Ser Gly Ser Gly Thr Asp Phe Thr Phe Thr Ile
 65                  70                  75                  80

Ser Ser Leu Glu Ala Glu Asp Ala Ala Thr Tyr Tyr Cys Ser Gln Asn
                 85                  90                  95

Thr His Val Pro Arg Thr Phe Gly Gln Gly
            100                 105

<210> SEQ ID NO 30
<211> LENGTH: 106
<212> TYPE: PRT
<213> ORGANISM: Artificial Sequence
<220> FEATURE:
<223> OTHER INFORMATION: light chain variable region

<400> SEQUENCE: 30

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Val His Ser
                20                  25                  30

Asn Gly Asn Thr Tyr Leu His Trp Tyr Gln Gln Lys Pro Gly Lys Ala
                35                  40                  45

Pro Lys Leu Leu Ile Tyr Lys Val Ser Tyr Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Arg Thr Phe Gly Gln Gly
            100                 105
```

<210> SEQ ID NO 31
<211> LENGTH: 106
<212> TYPE: PRT
<213> ORGANISM: Artificial Sequence
<220> FEATURE:
<223> OTHER INFORMATION: light chain variable region

<400> SEQUENCE: 31

```
Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Tyr Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Asn
                85                  90                  95

Thr His Val Pro Arg Thr Phe Gly Gln Gly
            100                 105
```

<210> SEQ ID NO 32
<211> LENGTH: 319
<212> TYPE: DNA
<213> ORGANISM: Artificial Sequence
<220> FEATURE:
<223> OTHER INFORMATION: light chain variable region

<400> SEQUENCE: 32

```
gatgttgtta tgacccaaac tccactctcc ctgtctgtca gtcttggaga tcaagcctcc    60
atctcttgca gatctagtca gagccttgta cacagtaatg aaacacccta tttacattgg   120
tacctgcaga agccaggcca gtctccaaag ctcctgatct acaaagtttc ctaccgattt   180
tctggggtcc cagacaggtt cagtggcagt ggatcaggga cagatttcac actcaagatc   240
agcagagtgg aggctgagga tctgggagtt tatttctgct ctcaaaatac acatgttcct   300
cggacgttcg gccaaggag                                                319
```

<210> SEQ ID NO 33
<211> LENGTH: 318
<212> TYPE: DNA
<213> ORGANISM: Artificial Sequence
<220> FEATURE:
<223> OTHER INFORMATION: light chain variable region

<400> SEQUENCE: 33

```
gatattgtga tgacccagac tccactctcc ctgcccgtca cccctggaga gccggcctcc    60
atctcctgca gatctagtca gagccttgta cacagtaatg aaacacccta tttacattgg   120
tatcagcaga aaccagggaa agctcctaag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                 318
```

<210> SEQ ID NO 34
<211> LENGTH: 318
<212> TYPE: DNA

<213> ORGANISM: Artificial Sequence
<220> FEATURE:
<223> OTHER INFORMATION: light chain variable region

<400> SEQUENCE: 34

```
gatgttgtga tgactcagtc tccactctcc ctgcccgtca cccttggaca gccggcctcc    60
atctcctgca gatctagtca gagccttgta cacagtaatg gaaacaccta tttacattgg   120
taccagcaga aacctggcca ggctcccagg ctcctcatct ataaagtttc ctaccgattt   180
tctggggtcc catcaaggtt cagcggcagt ggatctggga cagaattcac tctcaccatc   240
agcagcctgc agcctgatga ttttgcaact tattactgtt ctcaaaatac acatgttcct   300
cggacgttcg gccaaggg                                                  318
```

<210> SEQ ID NO 35
<211> LENGTH: 318
<212> TYPE: DNA
<213> ORGANISM: Artificial Sequence
<220> FEATURE:
<223> OTHER INFORMATION: light chain variable region

<400> SEQUENCE: 35

```
gatgttgtga tgactcagtc tccactctcc ctgcccgtca cccttggaca gccggcctcc    60
atctcctgca gatctagtca gagccttgta cacagtaatg gaaacaccta tttacattgg   120
tatcagcaga aaccagggaa agctcctaag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                  318
```

<210> SEQ ID NO 36
<211> LENGTH: 318
<212> TYPE: DNA
<213> ORGANISM: Artificial Sequence
<220> FEATURE:
<223> OTHER INFORMATION: light chain variable region

<400> SEQUENCE: 36

```
gacatccaga tgacccagtc tccatcctcc ctgtctgcat ctgtaggaga cagagtcacc    60
atcacttgca gatctagtca gagccttgta cacagtaatg gaaacaccta tttacattgg   120
tacctgcaga agccagggca gtctccacag ctcctgatct ataaagtttc ctaccgattt   180
tctgggatcc cagccaggtt cagtggcagt gggtctggga cagagttcac tctcaccatc   240
agcagcctgc agtctgaaga ttttgcagtt tattactgtt ctcaaaatac acatgttcct   300
cggacgttcg gccaaggg                                                  318
```

<210> SEQ ID NO 37
<211> LENGTH: 318
<212> TYPE: DNA
<213> ORGANISM: Artificial Sequence
<220> FEATURE:
<223> OTHER INFORMATION: light chain variable region

<400> SEQUENCE: 37

```
gatattgtga tgacccagac tccactctcc ctgcccgtca cccctggaga gccggcctcc    60
atctcctgca gatctagtca gagccttgta cacagtaatg gaaacaccta tttacattgg   120
tacctgcaga agccagggca gtctccacag ctcctgatct ataaagtttc ctaccgattt   180
tctggggtcc cagacaggtt cagtggcagt gggtcaggca ctgatttcac actgaaaatc   240
```

```
agcagggtgg aggctgagga tgttggagtt tattactgtt ctcaaaatac acatgttcct    300
cggacgttcg gccaaggg                                                   318

<210> SEQ ID NO 38
<211> LENGTH: 318
<212> TYPE: DNA
<213> ORGANISM: Artificial Sequence
<220> FEATURE:
<223> OTHER INFORMATION: light chain variable region

<400> SEQUENCE: 38
gacatccaga tgacccagtc tccatcctcc ctgtctgcat ctgtaggaga cagagtcacc    60
atcacttgca gatctagtca gagccttgta cacagtaatg gaaacaccta tttacattgg   120
tacctgcaga agccagggca gtctccacag ctcctgatct ataaagtttc ctaccgattt   180
tctgggatcc cagccaggtt cagtggcagt gggtctggga cagagttcac tctcaccatc   240
agcagcctgc agtctgaaga ttttgcagtt tattactgtt ctcaaaatac acatgttcct   300
cggacgttcg gccaaggg                                                   318

<210> SEQ ID NO 39
<211> LENGTH: 318
<212> TYPE: DNA
<213> ORGANISM: Artificial Sequence
<220> FEATURE:
<223> OTHER INFORMATION: light chain variable region

<400> SEQUENCE: 39
gatattgtga tgacccagac tccactctcc ctgcccgtca cccctggaga gccggcctcc    60
atctcctgca gatctagtca gagccttgta cacagtaatg gaaacaccta tttacattgg   120
tacctgcaga agccagggca gtctccacag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                   318

<210> SEQ ID NO 40
<211> LENGTH: 318
<212> TYPE: DNA
<213> ORGANISM: Artificial Sequence
<220> FEATURE:
<223> OTHER INFORMATION: light chain variable region

<400> SEQUENCE: 40
gatattgtga tgacccagac tccactctcc ctgcccgtca cccctggaga gccggcctcc    60
atctcctgca gatctagtca gagccttgta cacagtaatg gaaacaccta tttacattgg   120
tatcagcaga aaccagggaa agctcctaag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                   318

<210> SEQ ID NO 41
<211> LENGTH: 318
<212> TYPE: DNA
<213> ORGANISM: Artificial Sequence
<220> FEATURE:
<223> OTHER INFORMATION: light chain variable region
```

<400> SEQUENCE: 41

```
gatgttgtga tgactcagtc tccactctcc ctgcccgtca cccttggaca gccggcctcc    60
atctcctgca gatctagtca gagccttgta cacagtaatg gaaacaccta tttacattgg   120
tatcagcaga aaccagggaa agctcctaag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                  318
```

<210> SEQ ID NO 42
<211> LENGTH: 318
<212> TYPE: DNA
<213> ORGANISM: Artificial Sequence
<220> FEATURE:
<223> OTHER INFORMATION: light chain variable region

<400> SEQUENCE: 42

```
gatattgtga tgacccagac tccactctcc ctgcccgtca cccctggaga gccggcctcc    60
atctcctgca gatctagtca gagccttgta cacagtaatg gaaacaccta tttacattgg   120
tacctgcaga agccagggca gtctccacag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                  318
```

<210> SEQ ID NO 43
<211> LENGTH: 318
<212> TYPE: DNA
<213> ORGANISM: Artificial Sequence
<220> FEATURE:
<223> OTHER INFORMATION: light chain variable region

<400> SEQUENCE: 43

```
gaaattgtgt tgacacagtc tccagccacc ctgtctgtgt ctccagggga aagagccacc    60
ctctcctgca gatctagtca gagccttgta cacagtaatg gaaacaccta tttacattgg   120
taccagcaga aacctggcca ggctcccagg ctcctcatct ataaagtttc ctaccgattt   180
tctggggtcc cctcgaggtt cagtggcagt ggatctggga cagatttcac ctttaccatc   240
agtagcctgg aagctgaaga tgctgcaaca tattactgtt ctcaaaatac acatgttcct   300
cggacgttcg gccaaggg                                                  318
```

<210> SEQ ID NO 44
<211> LENGTH: 318
<212> TYPE: DNA
<213> ORGANISM: Artificial Sequence
<220> FEATURE:
<223> OTHER INFORMATION: light chain variable region

<400> SEQUENCE: 44

```
gatattgtga tgacccagac tccactctcc ctgcccgtca cccctggaga gccggcctcc    60
atctcctgca gatctagtca gagccttgta cacagtaatg gaaacaccta tttacattgg   120
tatcagcaga aaccagggaa agctcctaag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                  318
```

<210> SEQ ID NO 45
<211> LENGTH: 318
<212> TYPE: DNA
<213> ORGANISM: Artificial Sequence
<220> FEATURE:
<223> OTHER INFORMATION: light chain variable region

<400> SEQUENCE: 45

```
gatattgtga tgacccagac tccactctcc ctgcccgtca cccctggaga gccggcctcc     60
atctcctgca gatctagtca gagccttgta cacagtaatg aaacaccta tttacattgg    120
tatcagcaga aaccagggaa agctcctaag ctcctgatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318
```

<210> SEQ ID NO 46
<211> LENGTH: 318
<212> TYPE: DNA
<213> ORGANISM: Artificial Sequence
<220> FEATURE:
<223> OTHER INFORMATION: light chain variable region

<400> SEQUENCE: 46

```
gatgttgtga tgactcagtc tccactctcc ctgcccgtca cccttggaca gccggcctcc     60
atctcctgca gatctagtca gagccttgta cacagtaatg aaacaccta tttacattgg    120
tatcagcaga aaccagggaa agctcctaag ctcctgatct ataaagtttc ctaccgattt    180
tctggggtcc cagacaggtt cagtggcagt gggtcaggca ctgatttcac actgaaaatc    240
agcagggtgg aggctgagga tgttggagtt tattactgtt ctcaaaatac acatgttcct    300
cggacgttcg gccaaggg                                                  318
```

<210> SEQ ID NO 47
<211> LENGTH: 318
<212> TYPE: DNA
<213> ORGANISM: Artificial Sequence
<220> FEATURE:
<223> OTHER INFORMATION: light chain variable region

<400> SEQUENCE: 47

```
gccatccagt tgacccagtc tccatcctcc ctgtctgcat ctgtaggaga cagagtcacc     60
atcacttgca gatctagtca gagccttgta cacagtaatg aaacaccta tttacattgg    120
taccagcaga aacctggcca ggctcccagg ctcctcatct ataaagtttc ctaccgattt    180
tctggggtcc catcaaggtt cagcggcagt ggatctggga cagaattcac tctcaccatc    240
agcagcctgc agcctgatga ttttgcaact tattactgtt ctcaaaatac acatgttcct    300
cggacgttcg gccaaggg                                                  318
```

<210> SEQ ID NO 48
<211> LENGTH: 318
<212> TYPE: DNA
<213> ORGANISM: Artificial Sequence
<220> FEATURE:
<223> OTHER INFORMATION: light chain variable region

<400> SEQUENCE: 48

```
gccatccagt tgacccagtc tccatcctcc ctgtctgcat ctgtaggaga cagagtcacc     60
```

```
atcacttgca gatctagtca gagccttgta cacagtaatg gaaacaccta tttacattgg      120
taccagcaga aacctggcca ggctcccagg ctcctcatct ataaagtttc ctaccgattt      180
tctggggtcc cagacaggtt cagtggcagt gggtcaggca ctgatttcac actgaaaatc      240
agcagggtgg aggctgagga tgttggagtt tattactgtt ctcaaaatac acatgttcct      300
cggacgttcg gccaaggg                                                    318
```

<210> SEQ ID NO 49
<211> LENGTH: 318
<212> TYPE: DNA
<213> ORGANISM: Artificial Sequence
<220> FEATURE:
<223> OTHER INFORMATION: light chain variable region

<400> SEQUENCE: 49

```
gccatccagt tgacccagtc tccatcctcc ctgtctgcat ctgtaggaga cagagtcacc       60
atcacttgca gatctagtca gagccttgta cacagtaatg gaaacaccta tttacattgg      120
taccagcaga aacctggcca ggctcccagg ctcctcatct ataaagtttc ctaccgattt      180
tctggggtcc cagacaggtt cagtggcagt gggtcaggca ctgatttcac actgaaaatc      240
agcagggtgg aggctgagga tgttggagtt tattactgtt ctcaaaatac acatgttcct      300
cggacgttcg gccaaggg                                                    318
```

<210> SEQ ID NO 50
<211> LENGTH: 318
<212> TYPE: DNA
<213> ORGANISM: Artificial Sequence
<220> FEATURE:
<223> OTHER INFORMATION: light chain variable region

<400> SEQUENCE: 50

```
gaaattgtgt tgacacagtc tccagccacc ctgtctgtgt ctccagggga aagagccacc       60
ctctcctgca gatctagtca gagccttgta cacagtaatg gaaacaccta tttacattgg      120
taccagcaga aacctggcca ggctcccagg ctcctcatct ataaagtttc ctaccgattt      180
tctggggtcc cctcgaggtt cagtggcagt ggatctggga cagatttcac ctttaccatc      240
agtagcctgg aagctgaaga tgctgcaaca tattactgtt ctcaaaatac acatgttcct      300
cggacgttcg gccaaggg                                                    318
```

<210> SEQ ID NO 51
<211> LENGTH: 318
<212> TYPE: DNA
<213> ORGANISM: Artificial Sequence
<220> FEATURE:
<223> OTHER INFORMATION: light chain variable region

<400> SEQUENCE: 51

```
gatgttgtga tgactcagtc tccactctcc ctgcccgtca cccttggaca gccggcctcc       60
atctcctgca gatctagtca gagccttgta cacagtaatg gaaacaccta tttacattgg      120
tatcagcaga aaccagggaa agctcctaag ctcctgatct ataaagtttc ctaccgattt      180
tctggggtcc cagacaggtt cagtggcagt gggtcaggca ctgatttcac actgaaaatc      240
agcagggtgg aggctgagga tgttggagtt tattactgtt ctcaaaatac acatgttcct      300
cggacgttcg gccaaggg                                                    318
```

<210> SEQ ID NO 52
<211> LENGTH: 318

<212> TYPE: DNA
<213> ORGANISM: Artificial Sequence
<220> FEATURE:
<223> OTHER INFORMATION: light chain variable region

<400> SEQUENCE: 52

```
gatattgtga tgacccagac tccactctcc ctgcccgtca cccctggaga gccggcctcc    60
atctcctgca gatctagtca gagccttgta cacagtaatg aaacaccta tttacattgg   120
tacctgcaga agccagggca gtctccacag ctcctgatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                318
```

<210> SEQ ID NO 53
<211> LENGTH: 318
<212> TYPE: DNA
<213> ORGANISM: Artificial Sequence
<220> FEATURE:
<223> OTHER INFORMATION: light chain variable region

<400> SEQUENCE: 53

```
gccatccagt tgacccagtc tccatcctcc ctgtctgcat ctgtaggaga cagagtcacc    60
atcacttgca gatctagtca gagccttgta cacagtaatg aaacaccta tttacattgg   120
taccagcaga aacctggcca ggctcccagg ctcctcatct ataaagtttc ctaccgattt   180
tctggggtcc cagacaggtt cagtggcagt gggtcaggca ctgatttcac actgaaaatc   240
agcagggtgg aggctgagga tgttggagtt tattactgtt ctcaaaatac acatgttcct   300
cggacgttcg gccaaggg                                                318
```

<210> SEQ ID NO 54
<211> LENGTH: 318
<212> TYPE: DNA
<213> ORGANISM: Artificial Sequence
<220> FEATURE:
<223> OTHER INFORMATION: light chain variable region

<400> SEQUENCE: 54

```
gaaattgtgt tgacacagtc tccagccacc ctgtctgtgt ctccagggga aagagccacc    60
ctctcctgca gatctagtca gagccttgta cacagtaatg aaacaccta tttacattgg   120
taccagcaga aacctggcca ggctcccagg ctcctcatct ataaagtttc ctaccgattt   180
tctggggtcc cctcgaggtt cagtggcagt ggatctggga cagatttcac ctttaccatc   240
agtagcctgg aagctgaaga tgctgcaaca tattactgtt ctcaaaatac acatgttcct   300
cggacgttcg gccaaggg                                                318
```

<210> SEQ ID NO 55
<211> LENGTH: 318
<212> TYPE: DNA
<213> ORGANISM: Artificial Sequence
<220> FEATURE:
<223> OTHER INFORMATION: light chain variable region

<400> SEQUENCE: 55

```
gatattgtga tgacccagac tccactctcc ctgcccgtca cccctggaga gccggcctcc    60
atctcctgca gatctagtca gagccttgta cacagtaatg aaacaccta tttacattgg   120
tatcagcaga aaccagggaa agctcctaag ctcctgatct ataaagtttc ctaccgattt   180
```

```
tctggggtcc cagacaggtt cagtggcagt gggtcaggca ctgatttcac actgaaaatc      240 agcaggggtgg aggctgagga tgttggagtt tattactgtt ctcaaaatac acatgttcct      300
cggacgttcg gccaaggg                                                    318
```

<210> SEQ ID NO 56
<211> LENGTH: 318
<212> TYPE: DNA
<213> ORGANISM: Artificial Sequence
<220> FEATURE:
<223> OTHER INFORMATION: light chain variable region

<400> SEQUENCE: 56

```
gccatccagt tgacccagtc tccatcctcc ctgtctgcat ctgtaggaga cagagtcacc       60
atcacttgca gatctagtca gagccttgta cacagtaatg aaacaccta tttacattgg      120 taccagcaga aacctggcca ggctcccagg ctcctcatct ataaagtttc ctaccgattt      180
tctggggtcc catcaaggtt cagcggcagt ggatctggga cagaattcac tctcaccatc      240
agcagcctgc agcctgatga ttttgcaact tattactgtt ctcaaaatac acatgttcct      300
cggacgttcg gccaaggg                                                    318
```

<210> SEQ ID NO 57
<211> LENGTH: 109
<212> TYPE: PRT
<213> ORGANISM: Artificial Sequence
<220> FEATURE:
<223> OTHER INFORMATION: heavy chain variable region

<400> SEQUENCE: 57

```
Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
            20                  25                  30

Tyr Val Phe Trp Val Lys Gln Arg Pro Gly Gln Gly Leu Glu Trp Ile
        35                  40                  45

Gly Asp Ile Asn Pro Val Asn Gly Asp Thr Asn Phe Asn Glu Lys Phe
    50                  55                  60

Lys Asn Lys Ala Thr Leu Thr Val Asp Lys Ser Ser Thr Thr Thr Tyr
65                  70                  75                  80

Leu Gln Leu Ser Ser Leu Thr Ser Glu Asp Ser Ala Val Tyr Tyr Cys
                85                  90                  95

Thr Arg Gly Gly Tyr Thr Met Asp Tyr Trp Gly Gln Gly
            100                 105
```

<210> SEQ ID NO 58
<211> LENGTH: 109
<212> TYPE: PRT
<213> ORGANISM: Artificial Sequence
<220> FEATURE:
<223> OTHER INFORMATION: heavy chain variable region

<400> SEQUENCE: 58

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
```

```
                50                  55                  60
Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Thr Met Asp Tyr Trp Gly Gln Gly
                100                 105
```

<210> SEQ ID NO 59
<211> LENGTH: 109
<212> TYPE: PRT
<213> ORGANISM: Artificial Sequence
<220> FEATURE:
<223> OTHER INFORMATION: heavy chain variable region

<400> SEQUENCE: 59

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Thr Phe Thr Asn Tyr
                 20                  25                  30

Tyr Val Phe Trp Val Arg Gln Ala Arg Gly Gln Arg Leu Glu Trp Ile
                 35                  40                  45

Gly Asp Ile Asn Pro Val Asn Gly Asp Thr Asn Phe Asn Glu Lys Phe
 50                  55                  60

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Thr Met Asp Tyr Trp Gly Gln Gly
                100                 105
```

<210> SEQ ID NO 60
<211> LENGTH: 109
<212> TYPE: PRT
<213> ORGANISM: Artificial Sequence
<220> FEATURE:
<223> OTHER INFORMATION: heavy chain variable region

<400> SEQUENCE: 60

```
Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Asn Tyr
                 20                  25                  30

Tyr Val Phe Trp Val Arg Gln Ala Arg Gly Gln Arg Leu Glu Trp Ile
                 35                  40                  45

Gly Asp Ile Asn Pro Val Asn Gly Asp Thr Asn Phe Asn Glu Lys Phe
 50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Thr Met Asp Tyr Trp Gly Gln Gly
                100                 105
```

<210> SEQ ID NO 61
<211> LENGTH: 109
<212> TYPE: PRT
<213> ORGANISM: Artificial Sequence
<220> FEATURE:

<223> OTHER INFORMATION: heavy chain variable region

<400> SEQUENCE: 61

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Pro Gly Lys Gly Leu Glu Trp Val
        35                  40                  45

Ser Asp Ile Asn Pro Val Asn Gly Asp Thr Asn Phe Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 62
<211> LENGTH: 109
<212> TYPE: PRT
<213> ORGANISM: Artificial Sequence
<220> FEATURE:
<223> OTHER INFORMATION: heavy chain variable region

<400> SEQUENCE: 62

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Pro Gly Lys Gly Leu Glu Trp Val
        35                  40                  45

Ser Asp Ile Asn Pro Val Asn Gly Asp Thr Asn Phe Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 63
<211> LENGTH: 109
<212> TYPE: PRT
<213> ORGANISM: Artificial Sequence
<220> FEATURE:
<223> OTHER INFORMATION: heavy chain variable region

<400> SEQUENCE: 63

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val

```
                 65                  70                  75                  80
Leu Thr Met Thr Asn Met Asp Pro Val Asp Thr Ala Thr Tyr Tyr Cys
                    85                  90                  95

Ala Arg Gly Gly Tyr Thr Met Asp Tyr Trp Gly Gln Gly
                100                 105

<210> SEQ ID NO 64
<211> LENGTH: 109
<212> TYPE: PRT
<213> ORGANISM: Artificial Sequence
<220> FEATURE:
<223> OTHER INFORMATION: heavy chain variable region

<400> SEQUENCE: 64

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
                20                  25                  30

Tyr Val Phe Trp Val Arg Gln Ala Arg Gly Gln Arg Leu Glu Trp Ile
            35                  40                  45

Gly Asp Ile Asn Pro Val Asn Gly Asp Thr Asn Phe Asn Glu Lys Phe
        50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
                100                 105

<210> SEQ ID NO 65
<211> LENGTH: 109
<212> TYPE: PRT
<213> ORGANISM: Artificial Sequence
<220> FEATURE:
<223> OTHER INFORMATION: heavy chain variable region

<400> SEQUENCE: 65

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Asn Tyr
                20                  25                  30

Tyr Val Phe Trp Ile Arg Gln Ser Pro Ser Arg Gly Leu Glu Trp Leu
            35                  40                  45

Gly Asp Ile Asn Pro Val Asn Gly Asp Thr Asn Phe Asn Glu Lys Phe
        50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Thr Met Asp Tyr Trp Gly Gln Gly
                100                 105

<210> SEQ ID NO 66
<211> LENGTH: 109
<212> TYPE: PRT
<213> ORGANISM: Artificial Sequence
<220> FEATURE:
<223> OTHER INFORMATION: heavy chain variable region

<400> SEQUENCE: 66
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 67
<211> LENGTH: 109
<212> TYPE: PRT
<213> ORGANISM: Artificial Sequence
<220> FEATURE:
<223> OTHER INFORMATION: heavy chain variable region

<400> SEQUENCE: 67

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 68
<211> LENGTH: 109
<212> TYPE: PRT
<213> ORGANISM: Artificial Sequence
<220> FEATURE:
<223> OTHER INFORMATION: heavy chain variable region

<400> SEQUENCE: 68

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys

```
                    85                  90                  95

Ala Arg Gly Gly Tyr Thr Met Asp Tyr Trp Gly Gln Gly
                100                 105

<210> SEQ ID NO 69
<211> LENGTH: 109
<212> TYPE: PRT
<213> ORGANISM: Artificial Sequence
<220> FEATURE:
<223> OTHER INFORMATION: heavy chain variable region

<400> SEQUENCE: 69

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
                100                 105

<210> SEQ ID NO 70
<211> LENGTH: 109
<212> TYPE: PRT
<213> ORGANISM: Artificial Sequence
<220> FEATURE:
<223> OTHER INFORMATION: heavy chain variable region

<400> SEQUENCE: 70

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Ile Arg Gln Ser Pro Ser Arg Gly Leu Glu Trp Leu
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
                100                 105

<210> SEQ ID NO 71
<211> LENGTH: 109
<212> TYPE: PRT
<213> ORGANISM: Artificial Sequence
<220> FEATURE:
<223> OTHER INFORMATION: heavy chain variable region

<400> SEQUENCE: 71

Gln Val Gln Leu Gln Glu Ser Gly Pro Gly Leu Val Lys Pro Ser Gln
1               5                   10                  15
```

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
 50                  55                  60

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly
            100                 105

<210> SEQ ID NO 72
<211> LENGTH: 109
<212> TYPE: PRT
<213> ORGANISM: Artificial Sequence
<220> FEATURE:
<223> OTHER INFORMATION: heavy chain variable region

<400> SEQUENCE: 72

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
 50                  55                  60

Lys Asn Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 73
<211> LENGTH: 109
<212> TYPE: PRT
<213> ORGANISM: Artificial Sequence
<220> FEATURE:
<223> OTHER INFORMATION: heavy chain variable region

<400> SEQUENCE: 73

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
 50                  55                  60

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Gly Gly Tyr Thr Met Asp Tyr Trp Gly Gln Gly

<210> SEQ ID NO 74
<211> LENGTH: 109
<212> TYPE: PRT
<213> ORGANISM: Artificial Sequence
<220> FEATURE:
<223> OTHER INFORMATION: heavy chain variable region

<400> SEQUENCE: 74

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Ile Arg Gln Pro Pro Gly Lys Gly Leu Glu Trp Ile
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 75
<211> LENGTH: 109
<212> TYPE: PRT
<213> ORGANISM: Artificial Sequence
<220> FEATURE:
<223> OTHER INFORMATION: heavy chain variable region

<400> SEQUENCE: 75

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

Tyr Val Phe Trp Ile Arg Gln Ser Pro Ser Arg Gly Leu Glu Trp Leu
        35                  40                  45

Gly Asp Ile Asn Pro Val Asn Gly Asp Thr Asn Phe Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 76
<211> LENGTH: 109
<212> TYPE: PRT
<213> ORGANISM: Artificial Sequence
<220> FEATURE:
<223> OTHER INFORMATION: heavy chain variable region

<400> SEQUENCE: 76

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Asn Tyr
            20                  25                  30

```
Tyr Val Phe Trp Ile Arg Gln Ser Pro Ser Arg Gly Leu Glu Trp Leu
            35                  40                  45

Gly Asp Ile Asn Pro Val Asn Gly Asp Thr Asn Phe Asn Glu Lys Phe
     50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 77
<211> LENGTH: 109
<212> TYPE: PRT
<213> ORGANISM: Artificial Sequence
<220> FEATURE:
<223> OTHER INFORMATION: heavy chain variable region

<400> SEQUENCE: 77

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Asn Tyr
            20                  25                  30

Tyr Val Phe Trp Val Arg Gln Ala Pro Gly Gln Gly Leu Glu Trp Met
            35                  40                  45

Gly Asp Ile Asn Pro Val Asn Gly Asp Thr Asn Phe Asn Glu Lys Phe
     50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
            100                 105

<210> SEQ ID NO 78
<211> LENGTH: 109
<212> TYPE: PRT
<213> ORGANISM: Artificial Sequence
<220> FEATURE:
<223> OTHER INFORMATION: heavy chain variable region

<400> SEQUENCE: 78

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
            35                  40                  45

Gly Asp Ile Asn Pro Val Asn Gly Asp Thr Asn Phe Asn Glu Lys Phe
     50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Tyr Tyr Cys
                85                  90                  95

Ala Arg Gly Gly Tyr Thr Met Asp Tyr Trp Gly Gln Gly
            100                 105
```

-continued

```
<210> SEQ ID NO 79
<211> LENGTH: 109
<212> TYPE: PRT
<213> ORGANISM: Artificial Sequence
<220> FEATURE:
<223> OTHER INFORMATION: heavy chain variable region

<400> SEQUENCE: 79

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 80
<211> LENGTH: 109
<212> TYPE: PRT
<213> ORGANISM: Artificial Sequence
<220> FEATURE:
<223> OTHER INFORMATION: heavy chain variable region

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Gly Tyr Thr Met Asp Tyr Trp Gly Gln Gly
            100                 105

<210> SEQ ID NO 81
<211> LENGTH: 109
<212> TYPE: PRT
<213> ORGANISM: Artificial Sequence
<220> FEATURE:
<223> OTHER INFORMATION: heavy chain variable region

<400> SEQUENCE: 81

Gln Val Gln Leu Gln Glu Ser Gly Pro Gly Leu Val Lys Pro Gly Ala
1               5                   10                  15

Thr Val Lys Ile Ser Cys Lys Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45
```

```
Gly Asp Ile Asn Pro Val Asn Gly Asp Thr Asn Phe Asn Glu Lys Phe
        50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Tyr Thr Met Asp Tyr Trp Gly Gln Gly
                100                 105
```

<210> SEQ ID NO 82
<211> LENGTH: 327
<212> TYPE: DNA
<213> ORGANISM: Artificial Sequence
<220> FEATURE:
<223> OTHER INFORMATION: heavy chain variable region

<400> SEQUENCE: 82

```
gaggtccagc tgcagcagtt tggggctgaa ctggtgaagc ctggggcttc aatgaagttg      60
tcctgcaagg cttctggcta caccttcacc aactactatg tattctgggt gaaacagagg     120
cctggacaag gccttgagtg gattggagac attaatcctg tcaatggtga ctactaacttc    180 aatgagaaat tcaagaacaa ggccacactg actgtagaca gtcctccac cacaacatac      240 ttgcaactca gcagcctgac atctgaggac tctgcggtct attactgtac aagagggggt     300
tatactatgg actactgggg tcaagga                                         327
```

<210> SEQ ID NO 83
<211> LENGTH: 327
<212> TYPE: DNA
<213> ORGANISM: Artificial Sequence
<220> FEATURE:
<223> OTHER INFORMATION: heavy chain variable sequence

<400> SEQUENCE: 83

```
caggtgcagc tgcaggagtc gggcccagga ctggtgaagc cttcacagac cctgtccctc      60
acctgcactg tctctggcta caccttcacc aactactatg tattctgggt gcgacaggct     120
cgtggacaac gccttgagtg dataggtgac attaatcctg tcaatggtga ctactaacttc    180 aatgagaaat tcaagaacag agtcaccatc tcagccgaca gtccatcag caccgcctac      240 ctgcagtgga gcagcctgaa ggcctcggac accgccatgt attactgtgc gagagggggt     300
tatactatgg actactgggg ccaggga                                         327
```

<210> SEQ ID NO 84
<211> LENGTH: 327
<212> TYPE: DNA
<213> ORGANISM: Artificial Sequence
<220> FEATURE:
<223> OTHER INFORMATION: heavy chain variable sequence

<400> SEQUENCE: 84

```
caggtgcagc tgcaggagtc gggcccagga ctggtgaagc cttcacagac cctgtccctc      60
acctgcactg tctctggcta caccttcacc aactactatg tattctgggt gcgacaggct     120
cgtggacaac gccttgagtg dataggtgac attaatcctg tcaatggtga ctactaacttc    180 aatgagaaat tcaagaacag agtcaccatc tcagccgaca gtccatcag caccgcctac      240 ctgcagtgga gcagcctgaa ggcctcggac accgccatgt attactgtgc gagagggggt     300
tatactatgg actactgggg ccaggga                                         327
```

<210> SEQ ID NO 85
<211> LENGTH: 327
<212> TYPE: DNA
<213> ORGANISM: Artificial Sequence
<220> FEATURE:
<223> OTHER INFORMATION: heavy chain variable sequence

<400> SEQUENCE: 85

| gaagtgcagc tggtgcagtc tggagcagag gtgaaaaagc ccggggagtc tctgaggatc | 60 |
| tcctgtaagg gttctggcta caccttcacc aactactatg tattctgggt gcgacaggct | 120 |
| cgtggacaac gccttgagtg gataggtgac attaatcctg tcaatggtga tactaacttc | 180 |
| aatgagaaat tcaagaacag agtcacgatt accgcggaca atccacgag cacagcctac | 240 |
| atggagctga gcagcctgag atctgaggac acggccgtgt attactgtgc gagagggggt | 300 |
| tatactatgg actactgggg ccaggga | 327 |

<210> SEQ ID NO 86
<211> LENGTH: 327
<212> TYPE: DNA
<213> ORGANISM: Artificial Sequence
<220> FEATURE:
<223> OTHER INFORMATION: heavy chain variable region

<400> SEQUENCE: 86

| caggtgcagc tgcaggagtc gggcccagga ctggtgaagc cttcacagac cctgtccctc | 60 |
| acctgcactg tctctggcta caccttcacc aactactatg tattctgggt ccgccaggct | 120 |
| ccagggaagg ggctggagtg ggtcagtgac attaatcctg tcaatggtga tactaacttc | 180 |
| aatgagaaat tcaagaacag agtcaccata tcagtagaca cgtccaagaa ccagttctcc | 240 |
| ctgaagctga gctctgtgac cgccgcggac acggctgtgt attactgtgc gagagggggt | 300 |
| tatactatgg actactgggg ccaggga | 327 |

<210> SEQ ID NO 87
<211> LENGTH: 327
<212> TYPE: DNA
<213> ORGANISM: Artificial Sequence
<220> FEATURE:
<223> OTHER INFORMATION: heavy chain variable region

<400> SEQUENCE: 87

| caggtgcagc tgcaggagtc gggcccagga ctggtgaagc cttcacagac cctgtccctc | 60 |
| acctgcactg tctctggcta caccttcacc aactactatg tattctgggt ccgccaggct | 120 |
| ccagggaagg ggctggagtg ggtcagtgac attaatcctg tcaatggtga tactaacttc | 180 |
| aatgagaaat tcaagaacag agtcaccata tcagtagaca cgtccaagaa ccagttctcc | 240 |
| ctgaagctga gctctgtgac cgccgcggac acggctgtgt attactgtgc gagagggggt | 300 |
| tatactatgg actactgggg ccaggga | 327 |

<210> SEQ ID NO 88
<211> LENGTH: 327
<212> TYPE: DNA
<213> ORGANISM: Artificial Sequence
<220> FEATURE:
<223> OTHER INFORMATION: heavy chain variable region

<400> SEQUENCE: 88

| caggtgcagc tgcaggagtc gggcccagga ctggtgaagc cttcacagac cctgtccctc | 60 |
| acctgcactg tctctggcta caccttcacc aactactatg tattctgggt gcgacaggct | 120 |

```
cgtggacaac gccttgagtg gataggtgac attaatcctg tcaatggtga tactaacttc      180
aatgagaaat tcaagaacag actcaccatc tccaaggaca cctccaaaaa ccaggtggtc      240
cttacaatga ccaacatgga ccctgtggac acagccacgt attactgtgc aagagggggt      300
tatactatgg actactgggg ccaggga                                          327

<210> SEQ ID NO 89
<211> LENGTH: 327
<212> TYPE: DNA
<213> ORGANISM: Artificial Sequence
<220> FEATURE:
<223> OTHER INFORMATION: heavy chain variable region

<400> SEQUENCE: 89
caggtgcagc tgcaggagtc gggcccagga ctggtgaagc ctggggctac agtgaaaatc       60
tcctgcaagg tttctggcta caccttcacc aactactatg tattctgggt gcgacaggct     120
cgtggacaac gccttgagtg gataggtgac attaatcctg tcaatggtga tactaacttc     180
aatgagaaat tcaagaacag agtcacgatt accgcggaca atccacgag cacagcctac      240 atggagctga gcagcctgag atctgaggac acggccgtgt attactgtgc gagagggggt     300
tatactatgg actactgggg ccaggga                                          327

<210> SEQ ID NO 90
<211> LENGTH: 327
<212> TYPE: DNA
<213> ORGANISM: Artificial Sequence
<220> FEATURE:
<223> OTHER INFORMATION: heavy chain variable region

<400> SEQUENCE: 90
cagatcacct tgaaggagtc tggtcctacg ctggtgaaac ccacacagac cctcacgctg       60
acctgcacct tctctggcta caccttcacc aactactatg tattctggat caggcagtcc     120
ccatcgagag gccttgagtg gctgggtgac attaatcctg tcaatggtga tactaacttc     180
aatgagaaat tcaagaacag attcaccatc tccagagaca cgccaagaa ctcactgtat      240 ctgcaaatga acagcctgag agccgaggac acggctgtgt attactgtgc gagagggggt     300
tatactatgg actactgggg ccaggga                                          327

<210> SEQ ID NO 91
<211> LENGTH: 327
<212> TYPE: DNA
<213> ORGANISM: Artificial Sequence
<220> FEATURE:
<223> OTHER INFORMATION: heavy chain variable region

<400> SEQUENCE: 91
caggtgcagc tgcaggagtc gggcccagga ctggtgaagc cttcacagac cctgtccctc       60
acctgcactg tctctggcta caccttcacc aactactatg tattctgggt gcgacaggct     120
cgtggacaac gccttgagtg gataggtgac attaatcctg tcaatggtga tactaacttc     180
aatgagaaat tcaagaacag actcaccatc tccaaggaca cctccaaaaa ccaggtggtc     240
cttacaatga ccaacatgga ccctgtggac acagccacgt attactgtgc aagagggggt     300
tatactatgg actactgggg ccaggga                                          327

<210> SEQ ID NO 92
<211> LENGTH: 327
<212> TYPE: DNA
```

<213> ORGANISM: Artificial Sequence
<220> FEATURE:
<223> OTHER INFORMATION: heavy chain variable region

<400> SEQUENCE: 92

```
caggtgcagc tgcaggagtc gggcccagga ctggtgaagc cttcacagac cctgtccctc    60
acctgcactg tctctggcta ccttcacc aactactatg tattctgggt gcgacaggct    120
cgtggacaac gccttgagtg gataggtgac attaatcctg tcaatggtga tactaacttc    180
aatgagaaat tcaagaacag actcaccatc tccaaggaca cctccaaaaa ccaggtggtc    240
cttacaatga ccaacatgga ccctgtggac acagccacgt attactgtgc aagaggggt    300
tatactatgg actactgggg ccaggga                                        327
```

<210> SEQ ID NO 93
<211> LENGTH: 327
<212> TYPE: DNA
<213> ORGANISM: Artificial Sequence
<220> FEATURE:
<223> OTHER INFORMATION: heavy chain variable region

<400> SEQUENCE: 93

```
caggtgcagc tgcaggagtc gggcccagga ctggtgaagc ctggggctac agtgaaaatc    60
tcctgcaagg tttctggcta ccttcacc aactactatg tattctgggt gcgacaggct    120
cgtggacaac gccttgagtg gataggtgac attaatcctg tcaatggtga tactaacttc    180
aatgagaaat tcaagaacag agtcacgatt accgcggaca atccacgag cacagcctac    240
atggagctga gcagcctgag atctgaggac acggccgtgt attactgtgc gagaggggt    300
tatactatgg actactgggg ccaggga                                        327
```

<210> SEQ ID NO 94
<211> LENGTH: 327
<212> TYPE: DNA
<213> ORGANISM: Artificial Sequence
<220> FEATURE:
<223> OTHER INFORMATION: heavy chain variable region

<400> SEQUENCE: 94

```
caggtgcagc tgcaggagtc gggcccagga ctggtgaagc ctggggctac agtgaaaatc    60
tcctgcaagg tttctggcta caccttcacc aactactatg tattctgggt gcgacaggct    120
cgtggacaac gccttgagtg gataggtgac attaatcctg tcaatggtga tactaacttc    180
aatgagaaat tcaagaacag agtcacgatt accgcggaca atccacgag cacagcctac    240
atggagctga gcagcctgag atctgaggac acggccgtgt attactgtgc gagaggggt    300
tatactatgg actactgggg ccaggga                                        327
```

<210> SEQ ID NO 95
<211> LENGTH: 327
<212> TYPE: DNA
<213> ORGANISM: Artificial Sequence
<220> FEATURE:
<223> OTHER INFORMATION: heavy chain variable region

<400> SEQUENCE: 95

```
gaagtgcagc tggtgcagtc tggagcagag gtgaaaaagc ccggggagtc tctgaggatc    60
tcctgtaagg gttctggcta caccttcacc aactactatg tattctggat caggcagtcc    120
ccatcgagag gccttgagtg gctgggtgac attaatcctg tcaatggtga tactaacttc    180
aatgagaaat tcaagaacag agtcacgatt accgcggaca atccacgag cacagcctac    240
```

```
atggagctga gcagcctgag atctgaggac acggccgtgt attactgtgc gagaggggt    300 tatactatgg actactgggg ccaggga                                        327
```

<210> SEQ ID NO 96
<211> LENGTH: 327
<212> TYPE: DNA
<213> ORGANISM: Artificial Sequence
<220> FEATURE:
<223> OTHER INFORMATION: heavy chain variable region

<400> SEQUENCE: 96

```
caggtgcagc tgcaggagtc gggcccagga ctggtgaagc cttcacagac cctgtccctc    60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag agtcaccatc tcagccgaca gtccatcag caccgcctac    240 ctgcagtgga gcagcctgaa ggcctcggac accgccatgt attactgtgc gagaggggt    300 tatactatgg actactgggg ccaggga                                        327
```

<210> SEQ ID NO 97
<211> LENGTH: 327
<212> TYPE: DNA
<213> ORGANISM: Artificial Sequence
<220> FEATURE:
<223> OTHER INFORMATION: heavy chain variable region

<400> SEQUENCE: 97

```
caggtgcagc tgcaggagtc gggcccagga ctggtgaagc cttcacagac cctgtccctc    60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag actcaccatc tccaaggaca cctccaaaaa ccaggtggtc    240
cttacaatga ccaacatgga ccctgtggac acagccacgt attactgtgc aagaggggt    300 tatactatgg actactgggg ccaggga                                        327
```

<210> SEQ ID NO 98
<211> LENGTH: 327
<212> TYPE: DNA
<213> ORGANISM: Artificial Sequence
<220> FEATURE:
<223> OTHER INFORMATION: heavy chain variable region

<400> SEQUENCE: 98

```
caggtgcagc tgcaggagtc gggcccagga ctggtgaagc cttcacagac cctgtccctc    60
acctgcactg tctctggcta caccttcacc aactactatg tattctgggt gcgacaggct    120
cgtggacaac gccttgagtg gataggtgac attaatcctg tcaatggtga tactaacttc    180
aatgagaaat tcaagaacag agtcaccatc tcagccgaca gtccatcag caccgcctac    240 ctgcagtgga gcagcctgaa ggcctcggac accgccatgt attactgtgc gagaggggt    300 tatactatgg actactgggg ccaggga                                        327
```

<210> SEQ ID NO 99
<211> LENGTH: 327
<212> TYPE: DNA
<213> ORGANISM: Artificial Sequence
<220> FEATURE:
<223> OTHER INFORMATION: heavy chain variable region

<400> SEQUENCE: 99

```
gaggtccagc tggtacagtc tggggctgag gtgaagaagc ctggggctac agtgaaaatc    60
tcctgcaagg tttctggcta caccttcacc aactactatg tattctggat ccgccagccc   120
ccagggaagg gctggagtg gattggtgac attaatcctg tcaatggtga tactaacttc   180
aatgagaaat tcaagaacag agtcacgatt accgcggaca atccacgag cacagcctac    240
atggagctga gcagcctgag atctgaggac acggccgtgt attactgtgc gagaggggt    300
tatactatgg actactgggg ccaggga                                       327
```

<210> SEQ ID NO 100
<211> LENGTH: 327
<212> TYPE: DNA
<213> ORGANISM: Artificial Sequence
<220> FEATURE:
<223> OTHER INFORMATION: heavy chain variable region

<400> SEQUENCE: 100

```
gaagtgcagc tggtgcagtc tggagcagag gtgaaaaagc ccggggagtc tctgaggatc    60
tcctgtaagg gttctggcta caccttcacc aactactatg tattctggat caggcagtcc   120
ccatcgagag gccttgagtg gctgggtgac attaatcctg tcaatggtga tactaacttc   180
aatgagaaat tcaagaacag agtcacgatt accgcggaca atccacgag cacagcctac    240
atggagctga gcagcctgag atctgaggac acggccgtgt attactgtgc gagaggggt    300
tatactatgg actactgggg ccaggga                                       327
```

<210> SEQ ID NO 101
<211> LENGTH: 327
<212> TYPE: DNA
<213> ORGANISM: Artificial Sequence
<220> FEATURE:
<223> OTHER INFORMATION: heavy chain variable region

<400> SEQUENCE: 101

```
gaagtgcagc tggtgcagtc tggagcagag gtgaaaaagc ccggggagtc tctgaggatc    60
tcctgtaagg gttctggcta caccttcacc aactactatg tattctggat caggcagtcc   120
ccatcgagag gccttgagtg gctgggtgac attaatcctg tcaatggtga tactaacttc   180
aatgagaaat tcaagaacag agtcacgatt accgcggaca atccacgag cacagcctac    240
atggagctga gcagcctgag atctgaggac acggccgtgt attactgtgc gagagggggt   300
tatactatgg actactgggg ccaggga                                       327
```

<210> SEQ ID NO 102
<211> LENGTH: 327
<212> TYPE: DNA
<213> ORGANISM: Artificial Sequence
<220> FEATURE:
<223> OTHER INFORMATION: heavy chain variable region

<400> SEQUENCE: 102

```
cagatcacct tgaaggagtc tggtcctacg ctggtgaaac ccacacagac cctcacgctg    60
acctgcacct tctctggcta caccttcacc aactactatg tattctgggt gcgacaggcc   120
cctggacaag ggcttgagtg gatgggtgac attaatcctg tcaatggtga tactaacttc   180
aatgagaaat tcaagaacag agtcacgatt accgcggaca atccacgag cacagcctac    240
atggagctga gcagcctgag atctgaggac acggccgtgt attactgtgc gagagggggt   300
tatactatgg actactgggg ccaggga                                       327
```

<210> SEQ ID NO 103
<211> LENGTH: 327
<212> TYPE: DNA
<213> ORGANISM: Artificial Sequence
<220> FEATURE:
<223> OTHER INFORMATION: heavy chain variable region

<400> SEQUENCE: 103

```
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                        327
```

<210> SEQ ID NO 104
<211> LENGTH: 327
<212> TYPE: DNA
<213> ORGANISM: Artificial Sequence
<220> FEATURE:
<223> OTHER INFORMATION: heavy chain variable region

<400> SEQUENCE: 104

```
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                        327
```

<210> SEQ ID NO 105
<211> LENGTH: 327
<212> TYPE: DNA
<213> ORGANISM: Artificial Sequence
<220> FEATURE:
<223> OTHER INFORMATION: heavy chain variable region

<400> SEQUENCE: 105

```
caggtgcagc tgcaggagtc gggcccagga ctggtgaagc cttcacagac cctgtccctc    60
acctgcactg tctctggcta caccttcacc aactactatg tattctgggt gcgacaggct   120
cgtggacaac gccttgagtg gataggtgac attaatcctg tcaatggtga tactaacttc   180
aatgagaaat tcaagaacag actcaccatc tccaaggaca cctccaaaaa ccaggtggtc   240
cttacaatga ccaacatgga ccctgtggac acagccacgt attactgtgc aagagggggt   300
tatactatgg actactgggg ccaggga                                        327
```

<210> SEQ ID NO 106
<211> LENGTH: 327
<212> TYPE: DNA
<213> ORGANISM: Artificial Sequence
<220> FEATURE:
<223> OTHER INFORMATION: heavy chain variable region

<400> SEQUENCE: 106

```
caggtgcagc tgcaggagtc gggcccagga ctggtgaagc ctggggctac agtgaaaatc    60
```

```
tcctgcaagg tttctggcta caccttcacc aactactatg tattctgggt gcgacaggct    120
cgtggacaac gccttgagtg gataggtgac attaatcctg tcaatggtga tactaacttc    180
aatgagaaat tcaagaacag agtcacgatt accgcggaca atccacgag cacagcctac     240 atggagctga gcagcctgag atctgaggac acggccgtgt attactgtgc gagaggggt     300 tatactatgg actactgggg ccaggga                                        327
```

<210> SEQ ID NO 107
<211> LENGTH: 219
<212> TYPE: PRT
<213> ORGANISM: Artificial Sequence
<220> FEATURE:
<223> OTHER INFORMATION: complete light chain

<400> SEQUENCE: 107

```
Asp Val Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 108
<211> LENGTH: 660
<212> TYPE: DNA
<213> ORGANISM: Artificial Sequence
<220> FEATURE:
<223> OTHER INFORMATION: complete light chain

<400> SEQUENCE: 108

```
gatgttgtta tgacccaaac tccactctcc ctgtctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc ctaccgattt    180
tctggggtcc cagacaggtt cagtggcagt ggatcaggga cagatttcac actcaagatc   240
```

```
agcagagtgg aggctgagga tctgggagtt tatttctgct ctcaaaatac acatgttcct    300
cggacgttcg gccaagggac caaggtggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga    660
```

<210> SEQ ID NO 109
<211> LENGTH: 446
<212> TYPE: PRT
<213> ORGANISM: Artificial Sequence
<220> FEATURE:
<223> OTHER INFORMATION: complete heavy chain

<400> SEQUENCE: 109

```
Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
            20                  25                  30

Tyr Val Phe Trp Val Lys Gln Arg Pro Gly Gln Gly Leu Glu Trp Ile
        35                  40                  45

Gly Asp Ile Asn Pro Val Asn Gly Asp Thr Asn Phe Asn Glu Lys Phe
    50                  55                  60

Lys Asn Lys Ala Thr Leu Thr Val Asp Lys Ser Ser Thr Thr Thr Tyr
65                  70                  75                  80

Leu Gln Leu Ser Ser Leu Thr Ser Glu Asp Ser Ala Val Tyr Tyr Cys
                85                  90                  95

Thr Arg Gly Gly Tyr Thr Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

```
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 110
<211> LENGTH: 1341
<212> TYPE: PRT
<213> ORGANISM: Artificial Sequence
<220> FEATURE:
<223> OTHER INFORMATION: complete heavy chain

<400> SEQUENCE: 110

Gly Ala Gly Gly Thr Cys Cys Ala Gly Cys Thr Gly Cys Ala Gly Cys
1               5                   10                  15
Ala Gly Thr Thr Thr Gly Gly Gly Cys Thr Gly Ala Ala Cys Thr
            20                  25                  30
Gly Gly Thr Gly Ala Ala Gly Cys Cys Thr Gly Gly Gly Gly Cys Thr
        35                  40                  45
Thr Cys Ala Ala Thr Gly Ala Ala Gly Thr Thr Gly Thr Cys Cys Thr
    50                  55                  60
Gly Cys Ala Ala Gly Gly Cys Thr Thr Cys Thr Gly Gly Cys Thr Ala
65                  70                  75                  80
Cys Ala Cys Cys Thr Thr Cys Ala Cys Cys Ala Ala Cys Thr Ala Cys
                85                  90                  95
Thr Ala Thr Gly Thr Ala Thr Cys Thr Gly Gly Gly Thr Gly Ala
            100                 105                 110
Ala Ala Cys Ala Gly Ala Gly Gly Cys Cys Thr Gly Gly Ala Cys Ala
        115                 120                 125
Ala Gly Gly Cys Cys Thr Thr Gly Ala Gly Thr Gly Gly Ala Thr Thr
    130                 135                 140
Gly Gly Ala Gly Ala Cys Ala Thr Thr Ala Thr Cys Cys Thr Gly
145                 150                 155                 160
Thr Cys Ala Ala Thr Gly Gly Thr Gly Ala Thr Ala Cys Thr Ala Ala
                165                 170                 175
Cys Thr Thr Cys Ala Ala Thr Gly Ala Gly Ala Ala Ala Thr Thr Cys
            180                 185                 190
Ala Ala Gly Ala Ala Cys Ala Ala Gly Gly Cys Cys Ala Cys Ala Cys
        195                 200                 205
```

-continued

```
Thr Gly Ala Cys Thr Gly Thr Ala Gly Ala Cys Ala Ala Gly Thr Cys
    210                 215                 220

Cys Thr Cys Cys Ala Cys Cys Ala Cys Ala Ala Cys Ala Thr Ala Cys
225                 230                 235                 240

Thr Thr Gly Cys Ala Ala Cys Thr Cys Ala Gly Cys Ala Gly Cys Cys
                245                 250                 255

Thr Gly Ala Cys Ala Thr Cys Thr Gly Ala Gly Gly Ala Cys Thr Cys
            260                 265                 270

Thr Gly Cys Gly Gly Thr Cys Thr Ala Thr Thr Ala Cys Thr Gly Thr
        275                 280                 285

Ala Cys Ala Ala Gly Ala Gly Gly Gly Gly Gly Thr Thr Ala Thr Ala
    290                 295                 300

Cys Thr Ala Thr Gly Gly Ala Cys Thr Ala Cys Thr Gly Gly Gly Gly
305                 310                 315                 320

Cys Cys Ala Gly Gly Gly Ala Ala Cys Gly Cys Thr Gly Gly Thr Cys
                325                 330                 335

Ala Cys Cys Gly Thr Cys Ala Gly Cys Thr Cys Ala Gly Cys Cys Thr
            340                 345                 350

Cys Cys Ala Cys Cys Ala Ala Gly Gly Gly Cys Cys Cys Ala Thr Cys
        355                 360                 365

Gly Gly Thr Cys Thr Thr Cys Cys Cys Cys Cys Thr Gly Gly Cys Ala
    370                 375                 380

Cys Cys Cys Thr Cys Cys Thr Cys Cys Ala Ala Gly Ala Gly Cys Ala
385                 390                 395                 400

Cys Cys Thr Cys Thr Gly Gly Gly Gly Gly Cys Ala Cys Ala Gly Cys
                405                 410                 415

Gly Gly Cys Cys Cys Thr Gly Gly Gly Cys Thr Gly Cys Cys Thr Gly
            420                 425                 430

Gly Thr Cys Ala Ala Gly Gly Ala Cys Thr Ala Cys Thr Thr Cys Cys
        435                 440                 445

Cys Cys Gly Ala Ala Cys Cys Gly Gly Thr Gly Ala Cys Gly Gly Thr
    450                 455                 460

Gly Thr Cys Gly Thr Gly Gly Ala Ala Cys Thr Cys Ala Gly Gly Cys
465                 470                 475                 480

Gly Cys Cys Cys Thr Gly Ala Cys Cys Ala Gly Cys Gly Gly Cys Gly
                485                 490                 495

Thr Gly Cys Ala Cys Ala Cys Cys Thr Thr Cys Cys Cys Gly Gly Cys
            500                 505                 510

Thr Gly Thr Cys Cys Thr Ala Cys Ala Gly Thr Cys Cys Thr Cys Ala
        515                 520                 525

Gly Gly Ala Cys Thr Cys Thr Ala Cys Thr Cys Cys Cys Thr Cys Ala
    530                 535                 540

Gly Cys Ala Gly Cys Gly Thr Gly Gly Thr Gly Ala Cys Cys Gly Thr
545                 550                 555                 560

Gly Cys Cys Cys Thr Cys Cys Ala Gly Cys Ala Gly Cys Thr Thr Gly
                565                 570                 575

Gly Gly Cys Ala Cys Cys Cys Ala Gly Ala Cys Cys Thr Ala Cys Ala
            580                 585                 590

Thr Cys Thr Gly Cys Ala Ala Cys Gly Thr Gly Ala Ala Thr Cys Ala
        595                 600                 605

Cys Ala Ala Gly Cys Cys Cys Ala Gly Cys Ala Ala Cys Ala Cys Cys
    610                 615                 620

Ala Ala Gly Gly Thr Gly Gly Ala Cys Ala Ala Gly Ala Ala Ala Gly

-continued

```
625             630             635             640
Thr Thr Gly Ala Gly Cys Cys Ala Ala Ala Thr Cys Thr Thr Gly
                645             650             655
Thr Gly Ala Cys Ala Ala Ala Ala Cys Thr Cys Ala Cys Ala Cys Ala
                660             665             670
Thr Gly Cys Cys Ala Cys Cys Gly Thr Gly Cys Cys Ala Gly
                675             680             685
Cys Ala Cys Cys Thr Gly Ala Cys Thr Cys Cys Thr Gly Gly Gly
        690             695             700
Gly Gly Gly Ala Cys Cys Gly Thr Cys Ala Gly Thr Cys Thr Cys
705             710             715             720
Cys Thr Cys Thr Thr Cys Cys Cys Cys Ala Ala Ala Cys
                725             730             735
Cys Cys Ala Ala Gly Gly Ala Cys Ala Cys Cys Cys Thr Cys Ala Thr
                740             745             750
Gly Ala Thr Cys Thr Cys Cys Gly Gly Ala Cys Cys Cys Cys Thr
                755             760             765
Gly Ala Gly Gly Thr Cys Ala Cys Ala Thr Gly Cys Gly Thr Gly Gly
                770             775             780
Thr Gly Gly Thr Gly Gly Ala Cys Gly Thr Gly Ala Gly Cys Cys Ala
785             790             795             800
Cys Gly Ala Ala Gly Ala Cys Cys Cys Thr Gly Ala Gly Gly Thr Cys
                805             810             815
Ala Ala Gly Thr Thr Cys Ala Ala Cys Thr Gly Gly Thr Ala Cys Gly
                820             825             830
Thr Gly Gly Ala Cys Gly Gly Cys Gly Thr Gly Gly Ala Gly Gly Thr
                835             840             845
Gly Cys Ala Thr Ala Ala Thr Gly Cys Cys Ala Ala Gly Ala Cys Ala
        850             855             860
Ala Ala Gly Cys Cys Gly Cys Gly Gly Gly Ala Gly Gly Ala Gly Cys
865             870             875             880
Ala Gly Thr Ala Cys Ala Ala Cys Ala Gly Cys Ala Cys Gly Thr Ala
                885             890             895
Cys Cys Gly Thr Gly Thr Gly Gly Thr Cys Ala Gly Cys Gly Thr Cys
                900             905             910
Cys Thr Cys Ala Cys Cys Gly Thr Cys Thr Gly Cys Ala Cys Cys
        915             920             925
Ala Gly Gly Ala Cys Thr Gly Gly Cys Thr Gly Ala Ala Thr Gly Gly
930             935             940
Cys Ala Ala Gly Gly Ala Gly Thr Ala Cys Ala Ala Gly Thr Gly Cys
945             950             955             960
Ala Ala Gly Gly Thr Cys Ala Gly Cys Ala Ala Cys Ala Ala Ala Gly
                965             970             975
Cys Cys Cys Thr Cys Cys Ala Gly Cys Cys Cys Cys Ala Thr
                980             985             990
Cys Gly Ala Gly Ala Ala Ala Ala Cys Cys Ala Thr Cys Thr Cys Cys
        995             1000            1005
Ala Ala Ala Gly Cys Cys Ala Ala Ala Gly Gly Gly Cys Ala Gly
        1010            1015            1020
Cys Cys Cys Cys Gly Ala Gly Ala Ala Cys Cys Ala Cys Ala Gly
        1025            1030            1035
Gly Thr Gly Thr Ala Cys Ala Cys Cys Cys Thr Gly Cys Cys Cys
        1040            1045            1050
```

Cys Cys Ala Thr Cys Cys Cys Gly Gly Ala Thr Gly Ala Gly
        1055                1060                1065

Cys Thr Gly Ala Cys Cys Ala Ala Gly Ala Ala Cys Cys Ala Gly
        1070                1075                1080

Gly Thr Cys Ala Gly Cys Cys Thr Gly Ala Cys Cys Thr Gly Cys
        1085                1090                1095

Cys Thr Gly Gly Thr Cys Ala Ala Ala Gly Gly Cys Thr Thr Cys
        1100                1105                1110

Thr Ala Thr Cys Cys Cys Ala Gly Cys Gly Ala Cys Ala Thr Cys
        1115                1120                1125

Gly Cys Cys Gly Thr Gly Gly Ala Gly Thr Gly Gly Gly Ala Gly
        1130                1135                1140

Ala Gly Cys Ala Ala Thr Gly Gly Cys Ala Gly Cys Cys Gly
        1145                1150                1155

Gly Ala Gly Ala Ala Cys Ala Ala Cys Thr Ala Cys Ala Ala Gly
        1160                1165                1170

Ala Cys Cys Ala Cys Gly Cys Cys Thr Cys Cys Cys Gly Thr Gly
        1175                1180                1185

Cys Thr Gly Gly Ala Cys Thr Cys Cys Gly Ala Cys Gly Gly Cys
        1190                1195                1200

Thr Cys Cys Thr Thr Cys Thr Thr Cys Cys Thr Cys Thr Ala Cys
        1205                1210                1215

Ala Gly Cys Ala Ala Gly Cys Thr Cys Ala Cys Cys Gly Thr Gly
        1220                1225                1230

Gly Ala Cys Ala Ala Gly Ala Gly Cys Ala Gly Gly Thr Gly Gly
        1235                1240                1245

Cys Ala Gly Cys Ala Gly Gly Gly Gly Ala Ala Cys Gly Thr Cys
        1250                1255                1260

Thr Thr Cys Thr Cys Ala Thr Gly Cys Thr Cys Cys Gly Thr Gly
        1265                1270                1275

Ala Thr Gly Cys Ala Thr Gly Ala Gly Gly Cys Thr Cys Thr Gly
        1280                1285                1290

Cys Ala Cys Ala Ala Cys Cys Ala Cys Thr Ala Cys Ala Cys Gly
        1295                1300                1305

Cys Ala Gly Ala Ala Gly Ala Gly Cys Cys Thr Cys Thr Cys Cys
        1310                1315                1320

Cys Thr Gly Thr Cys Thr Cys Cys Gly Gly Thr Ala Ala Ala
        1325                1330                1335

Thr Gly Ala
        1340

<210> SEQ ID NO 111
<211> LENGTH: 354
<212> TYPE: PRT
<213> ORGANISM: Artificial Sequence
<220> FEATURE:
<223> OTHER INFORMATION: complete heavy chain

<400> SEQUENCE: 111

Glu Val Gln Leu Gln Gln Phe Gly Ala Glu Leu Val Lys Pro Gly Ala
1               5                   10                  15

Ser Met Lys Leu Ser Cys Lys Ala Ser Gly Tyr Thr Phe Thr Asn Tyr
                20                  25                  30

Tyr Val Phe Trp Val Lys Gln Arg Pro Gly Gln Gly Leu Glu Trp Ile
        35                  40                  45

```
Gly Asp Ile Asn Pro Val Asn Gly Asp Thr Asn Phe Asn Glu Lys Phe
         50                  55                  60

Lys Asn Lys Ala Thr Leu Thr Val Asp Lys Ser Thr Thr Thr Tyr
 65                  70                  75                  80

Leu Gln Leu Ser Ser Leu Thr Ser Glu Asp Ser Ala Val Tyr Tyr Cys
                 85                  90                  95

Thr Arg Gly Gly Tyr Thr Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Gln Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg

<210> SEQ ID NO 112
<211> LENGTH: 442
<212> TYPE: PRT
<213> ORGANISM: Artificial Sequence
<220> FEATURE:
<223> OTHER INFORMATION: complete heavy chain

<400> SEQUENCE: 112

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45
```

Gly Asp Ile Asn Pro Val Asn Gly Asp Thr Asn Phe Asn Glu Lys Phe
    50                  55                  60

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Thr Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Asn Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 113
<211> LENGTH: 443
<212> TYPE: PRT

<213> ORGANISM: Artificial Sequence
<220> FEATURE:
<223> OTHER INFORMATION: complete heavy chain

<400> SEQUENCE: 113

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Asn Tyr
            20                  25                  30

Tyr Val Phe Trp Val Arg Gln Ala Arg Gly Gln Arg Leu Glu Trp Ile
        35                  40                  45

Gly Asp Ile Asn Pro Val Asn Gly Asp Thr Asn Phe Asn Glu Lys Phe
50                  55                  60

Lys Asn Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gly Gly Tyr Thr Met Asp Tyr Trp Gly Gln Gly Thr Thr Val
        100                 105                 110

Thr Val Ser Ser Ala Ser Thr Lys Gly Pro Ser Val Phe Pro Leu Ala
    115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
    195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
        260                 265                 270

Trp Tyr Val Asp Gly Val Glu Val His Asn Ala Lys Thr Lys Pro Arg
    275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe

```
              385                 390                 395                 400
Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
                435                 440

<210> SEQ ID NO 114
<211> LENGTH: 1341
<212> TYPE: PRT
<213> ORGANISM: Artificial Sequence
<220> FEATURE:
<223> OTHER INFORMATION: complete heavy chain

<400> SEQUENCE: 114

Gly Ala Gly Gly Thr Cys Cys Ala Gly Cys Thr Gly Cys Ala Gly Cys
1               5                   10                  15

Ala Gly Thr Thr Thr Gly Gly Gly Cys Thr Gly Ala Ala Cys Thr
                20                  25                  30

Gly Gly Thr Gly Ala Ala Gly Cys Cys Thr Gly Gly Gly Cys Thr
            35                  40                  45

Thr Cys Ala Ala Thr Gly Ala Ala Gly Thr Thr Gly Thr Cys Cys Thr
        50                  55                  60

Gly Cys Ala Ala Gly Gly Cys Thr Thr Cys Thr Gly Gly Cys Thr Ala
65                  70                  75                  80

Cys Ala Cys Cys Thr Thr Cys Ala Cys Cys Ala Ala Cys Thr Ala Cys
                85                  90                  95

Thr Ala Thr Gly Thr Ala Thr Cys Thr Gly Gly Gly Thr Gly Ala
                100                 105                 110

Ala Ala Cys Ala Gly Ala Gly Gly Cys Cys Thr Gly Ala Cys Ala
            115                 120                 125

Ala Gly Gly Cys Cys Thr Thr Gly Ala Gly Thr Gly Ala Thr Thr
        130                 135                 140

Gly Gly Ala Gly Ala Cys Ala Thr Thr Ala Ala Thr Cys Cys Thr Gly
145                 150                 155                 160

Thr Cys Ala Ala Thr Gly Gly Thr Gly Ala Thr Ala Cys Thr Ala Ala
                165                 170                 175

Cys Thr Thr Cys Ala Ala Thr Gly Ala Gly Ala Ala Ala Thr Thr Cys
                180                 185                 190

Ala Ala Gly Ala Cys Ala Ala Gly Gly Cys Cys Ala Cys Ala Cys
            195                 200                 205

Thr Gly Ala Cys Thr Gly Thr Ala Gly Ala Cys Ala Ala Gly Thr Cys
        210                 215                 220

Cys Thr Cys Cys Ala Cys Cys Ala Cys Ala Gly Cys Ala Thr Ala Cys
225                 230                 235                 240

Thr Thr Gly Cys Ala Ala Cys Thr Cys Ala Gly Cys Ala Gly Cys Cys
                245                 250                 255

Thr Gly Ala Cys Ala Thr Cys Thr Gly Ala Gly Gly Ala Cys Thr Cys
                260                 265                 270

Thr Gly Cys Gly Gly Thr Cys Thr Ala Thr Thr Ala Cys Thr Gly Thr
            275                 280                 285

Ala Cys Ala Ala Gly Ala Gly Gly Gly Thr Thr Ala Thr Ala
        290                 295                 300

Cys Thr Ala Thr Gly Gly Ala Cys Thr Ala Cys Thr Gly Gly Gly Gly
```

```
                305                 310                 315                 320
Cys Cys Ala Gly Gly Gly Ala Ala Cys Gly Cys Thr Gly Gly Thr Cys
                    325                 330                 335
Ala Cys Cys Gly Thr Cys Ala Gly Cys Thr Cys Ala Gly Cys Cys Thr
                    340                 345                 350
Cys Cys Ala Cys Ala Ala Gly Gly Cys Cys Ala Thr Cys
                    355                 360                 365
Gly Gly Thr Cys Thr Thr Cys Cys Cys Cys Thr Gly Gly Cys Ala
370                 375                 380
Cys Cys Cys Thr Cys Thr Cys Cys Ala Ala Gly Ala Gly Cys Ala
385                 390                 395                 400
Cys Cys Thr Cys Thr Gly Gly Gly Gly Cys Ala Cys Ala Gly Cys
                    405                 410                 415
Gly Gly Cys Cys Cys Thr Gly Gly Cys Thr Gly Cys Thr Gly
                    420                 425                 430
Gly Thr Cys Ala Ala Gly Gly Ala Cys Thr Ala Cys Thr Thr Cys Cys
            435                 440                 445
Cys Cys Gly Ala Ala Cys Cys Gly Gly Thr Gly Ala Cys Gly Gly Thr
            450                 455                 460
Gly Thr Cys Gly Thr Gly Gly Ala Ala Cys Thr Cys Ala Gly Gly Cys
465                 470                 475                 480
Gly Cys Cys Cys Thr Gly Ala Cys Cys Ala Gly Cys Gly Gly Cys Gly
                    485                 490                 495
Thr Gly Cys Ala Cys Ala Cys Cys Thr Thr Cys Cys Cys Gly Gly Cys
                    500                 505                 510
Thr Gly Thr Cys Cys Thr Ala Cys Ala Gly Thr Cys Cys Thr Cys Ala
            515                 520                 525
Gly Gly Ala Cys Thr Cys Thr Ala Cys Thr Cys Cys Thr Cys Ala
            530                 535                 540
Gly Cys Ala Gly Cys Gly Thr Gly Gly Thr Gly Ala Cys Cys Gly Thr
545                 550                 555                 560
Gly Cys Cys Cys Thr Cys Cys Ala Gly Cys Ala Gly Cys Thr Thr Gly
                    565                 570                 575
Gly Gly Cys Ala Cys Cys Cys Ala Gly Ala Cys Cys Thr Ala Cys Ala
                    580                 585                 590
Thr Cys Thr Gly Cys Ala Ala Cys Gly Thr Gly Ala Ala Thr Cys Ala
            595                 600                 605
Cys Ala Ala Gly Cys Cys Ala Gly Cys Ala Ala Cys Ala Cys Cys
            610                 615                 620
Ala Ala Gly Gly Thr Gly Gly Ala Cys Ala Ala Gly Ala Ala Ala Gly
625                 630                 635                 640
Thr Thr Gly Ala Gly Cys Cys Cys Ala Ala Ala Thr Cys Thr Thr Gly
                    645                 650                 655
Thr Gly Ala Cys Ala Ala Ala Cys Thr Cys Ala Cys Ala Cys Ala
                    660                 665                 670
Thr Gly Cys Cys Cys Ala Cys Cys Gly Thr Gly Cys Cys Cys Ala Gly
            675                 680                 685
Cys Ala Cys Cys Thr Gly Ala Ala Cys Thr Cys Cys Thr Gly Gly Gly
            690                 695                 700
Gly Gly Gly Ala Cys Cys Gly Thr Cys Ala Gly Thr Cys Thr Thr Cys
705                 710                 715                 720
Cys Thr Cys Thr Thr Cys Cys Cys Cys Cys Cys Ala Ala Ala Ala Cys
                    725                 730                 735
```

```
Cys Cys Ala Ala Gly Gly Ala Cys Ala Cys Cys Thr Cys Ala Thr
            740                 745                 750

Gly Ala Thr Cys Thr Cys Cys Gly Gly Ala Cys Cys Cys Cys Thr
        755                 760                 765

Gly Ala Gly Gly Thr Cys Ala Cys Ala Thr Gly Cys Gly Thr Gly
        770                 775                 780

Thr Gly Gly Thr Gly Gly Ala Cys Gly Thr Gly Ala Gly Cys Cys Ala
785                 790                 795                 800

Cys Gly Ala Ala Gly Ala Cys Cys Thr Gly Ala Gly Gly Thr Cys
            805                 810                 815

Ala Ala Gly Thr Thr Cys Ala Ala Cys Thr Gly Gly Thr Ala Cys Gly
            820                 825                 830

Thr Gly Gly Ala Cys Gly Gly Cys Gly Thr Gly Gly Ala Gly Gly Thr
        835                 840                 845

Gly Cys Ala Thr Ala Ala Thr Gly Cys Cys Ala Ala Gly Ala Cys Ala
        850                 855                 860

Ala Ala Gly Cys Cys Gly Cys Gly Gly Gly Ala Gly Gly Ala Gly Cys
865                 870                 875                 880

Ala Gly Thr Ala Cys Cys Ala Gly Ala Cys Ala Cys Gly Thr Ala
            885                 890                 895

Cys Cys Gly Thr Gly Thr Gly Gly Thr Cys Ala Gly Cys Gly Thr Cys
        900                 905                 910

Cys Thr Cys Ala Cys Cys Gly Thr Cys Cys Thr Gly Cys Ala Cys Cys
            915                 920                 925

Ala Gly Gly Ala Cys Thr Gly Gly Cys Thr Gly Ala Ala Thr Gly Gly
        930                 935                 940

Cys Ala Ala Gly Gly Ala Gly Thr Ala Cys Ala Ala Gly Thr Gly Cys
945                 950                 955                 960

Ala Ala Gly Gly Thr Cys Ala Gly Cys Ala Ala Cys Ala Ala Ala Gly
            965                 970                 975

Cys Cys Cys Thr Cys Cys Ala Gly Cys Cys Cys Cys Cys Ala Thr
            980                 985                 990

Cys Gly Ala Gly Ala Ala Ala Cys Cys Ala Thr Cys  Thr Cys Cys
            995             1000                1005

Ala Ala Ala Gly Cys Cys Ala Ala Gly Gly Gly  Cys Ala Gly
        1010                1015               1020

Cys Cys Cys Cys Gly Ala Gly Ala Ala Cys Cys Ala Cys Ala Gly
1025                1030               1035

Gly Thr Gly Thr Ala Cys Ala Cys Cys Cys Thr Gly Cys Cys Cys
        1040                1045              1050

Cys Cys Ala Thr Cys Cys Cys Gly Gly Gly Ala Thr Gly Ala Gly
        1055                1060              1065

Cys Thr Gly Ala Cys Cys Ala Ala Gly Ala Ala Cys Cys Ala Gly
        1070                1075              1080

Gly Thr Cys Ala Gly Cys Cys Thr Gly Ala Cys Cys Thr Gly Cys
        1085                1090              1095

Cys Thr Gly Gly Thr Cys Ala Ala Ala Gly Gly Cys Thr Thr Cys
        1100                1105              1110

Thr Ala Thr Cys Cys Cys Ala Gly Cys Gly Ala Cys Ala Thr Cys
        1115                1120              1125

Gly Cys Cys Gly Thr Gly Gly Ala Gly Thr Gly Gly Gly Ala Gly
        1130                1135              1140
```

Ala Gly Cys Ala Ala Thr Gly Gly Cys Ala Gly Cys Cys Gly
1145                1150                1155

Gly Ala Gly Ala Ala Cys Ala Ala Cys Thr Ala Cys Ala Ala Gly
    1160            1165                1170

Ala Cys Cys Ala Cys Gly Cys Cys Thr Cys Cys Cys Gly Thr Gly
    1175            1180                1185

Cys Thr Gly Gly Ala Cys Thr Cys Cys Gly Ala Cys Gly Gly Cys
    1190            1195                1200

Thr Cys Cys Thr Thr Cys Thr Thr Cys Cys Thr Cys Thr Ala Cys
    1205            1210                1215

Ala Gly Cys Ala Ala Gly Cys Thr Cys Ala Cys Cys Gly Thr Gly
    1220            1225                1230

Gly Ala Cys Ala Ala Gly Ala Gly Cys Ala Gly Gly Thr Gly Gly
    1235            1240                1245

Cys Ala Gly Cys Ala Gly Gly Gly Ala Ala Cys Gly Thr Cys
    1250            1255                1260

Thr Thr Cys Thr Cys Ala Thr Gly Cys Thr Cys Cys Gly Thr Gly
    1265            1270                1275

Ala Thr Gly Cys Ala Thr Gly Ala Gly Gly Cys Thr Cys Thr Gly
    1280            1285                1290

Cys Ala Cys Ala Ala Cys Cys Ala Cys Thr Ala Cys Ala Cys Gly
    1295            1300                1305

Cys Ala Gly Ala Ala Gly Ala Gly Cys Cys Thr Cys Thr Cys Cys
    1310            1315                1320

Cys Thr Gly Thr Cys Thr Cys Cys Gly Gly Gly Thr Ala Ala Ala
    1325            1330                1335

Thr Gly Ala
    1340

<210> SEQ ID NO 115
<211> LENGTH: 1326
<212> TYPE: PRT
<213> ORGANISM: Artificial Sequence
<220> FEATURE:
<223> OTHER INFORMATION: complete heavy chain

<400> SEQUENCE: 115

Cys Ala Gly Gly Thr Gly Cys Ala Gly Cys Thr Gly Cys Ala Gly Gly
1               5                   10                  15

Ala Gly Thr Cys Gly Gly Gly Cys Cys Cys Ala Gly Gly Ala Cys Thr
                20                  25                  30

Gly Gly Thr Gly Ala Ala Gly Cys Cys Thr Thr Cys Ala Cys Ala Gly
            35                  40                  45

Ala Cys Cys Cys Thr Gly Thr Cys Cys Cys Thr Cys Ala Cys Cys Thr
        50                  55                  60

Gly Cys Ala Cys Thr Gly Thr Cys Thr Cys Thr Gly Gly Cys Thr Ala
65                  70                  75                  80

Cys Ala Cys Cys Thr Thr Cys Ala Cys Cys Ala Ala Cys Thr Ala Cys
                85                  90                  95

Thr Ala Thr Gly Thr Ala Thr Cys Thr Gly Gly Gly Thr Gly Cys
            100                 105                 110

Gly Ala Cys Ala Gly Gly Cys Thr Cys Gly Thr Gly Gly Ala Cys Ala
        115                 120                 125

Ala Cys Gly Cys Cys Thr Thr Gly Ala Gly Thr Gly Gly Ala Thr Ala
    130                 135                 140

-continued

```
Gly Gly Thr Gly Ala Cys Ala Thr Thr Ala Thr Cys Cys Thr Gly
145                 150                 155                 160

Thr Cys Ala Ala Thr Gly Gly Thr Gly Ala Thr Ala Cys Thr Ala Ala
                165                 170                 175

Cys Thr Thr Cys Ala Ala Thr Gly Ala Gly Ala Ala Thr Thr Cys
                180                 185                 190

Ala Ala Gly Ala Ala Cys Ala Gly Ala Gly Thr Cys Ala Cys Cys Ala
                195                 200                 205

Thr Cys Thr Cys Ala Gly Cys Cys Gly Ala Cys Ala Ala Gly Thr Cys
210                 215                 220

Cys Ala Thr Cys Ala Gly Cys Ala Cys Gly Cys Thr Ala Cys
225                 230                 235                 240

Cys Thr Gly Cys Ala Gly Thr Gly Gly Ala Gly Cys Ala Gly Cys Cys
                245                 250                 255

Thr Gly Ala Ala Gly Gly Cys Thr Cys Gly Gly Ala Cys Ala Cys
                260                 265                 270

Cys Gly Cys Cys Ala Thr Gly Thr Ala Thr Thr Ala Cys Thr Gly Thr
                275                 280                 285

Gly Cys Gly Ala Gly Ala Gly Gly Gly Gly Thr Thr Ala Thr Ala
290                 295                 300

Cys Thr Ala Thr Gly Gly Ala Cys Thr Ala Cys Thr Gly Gly Gly Gly
305                 310                 315                 320

Cys Cys Ala Gly Gly Gly Ala Ala Cys Cys Cys Thr Gly Gly Thr Cys
                325                 330                 335

Ala Cys Cys Gly Thr Cys Ala Gly Cys Thr Cys Ala Gly Cys Cys Thr
                340                 345                 350

Cys Cys Ala Cys Ala Ala Gly Gly Gly Cys Cys Cys Ala Thr Cys Cys
                355                 360                 365

Gly Gly Thr Cys Thr Thr Cys Cys Cys Cys Thr Gly Gly Cys Ala
                370                 375                 380

Cys Cys Cys Thr Gly Cys Thr Cys Cys Ala Gly Gly Ala Gly Cys Ala
385                 390                 395                 400

Cys Cys Thr Cys Cys Gly Ala Gly Ala Gly Cys Ala Cys Ala Gly Cys
                405                 410                 415

Gly Gly Cys Cys Cys Thr Gly Gly Gly Cys Thr Gly Cys Cys Thr Gly
                420                 425                 430

Gly Thr Cys Ala Ala Gly Gly Ala Cys Thr Ala Cys Thr Thr Cys Cys
                435                 440                 445

Cys Cys Gly Ala Ala Cys Cys Gly Gly Thr Gly Ala Cys Gly Gly Thr
450                 455                 460

Gly Thr Cys Gly Thr Gly Gly Ala Ala Cys Thr Cys Ala Gly Gly Cys
465                 470                 475                 480

Gly Cys Thr Cys Thr Gly Ala Cys Cys Ala Gly Cys Gly Gly Cys Gly
                485                 490                 495

Thr Gly Cys Ala Cys Ala Cys Cys Thr Thr Cys Cys Cys Gly Gly Cys
                500                 505                 510

Thr Gly Thr Cys Cys Thr Ala Cys Ala Gly Thr Cys Cys Thr Cys Ala
                515                 520                 525

Gly Gly Ala Cys Thr Cys Thr Ala Cys Thr Cys Cys Cys Thr Cys Ala
                530                 535                 540

Gly Cys Ala Gly Cys Gly Thr Gly Gly Thr Gly Ala Cys Cys Gly Thr
                545                 550                 555                 560

Gly Cys Cys Cys Thr Cys Cys Ala Gly Cys Ala Ala Cys Thr Thr Cys
```

```
                565                 570                 575
Gly Gly Cys Ala Cys Cys Ala Gly Ala Cys Cys Thr Ala Cys Ala
            580                 585                 590
Cys Cys Thr Gly Cys Ala Ala Cys Gly Thr Ala Gly Ala Thr Cys Ala
            595                 600                 605
Cys Ala Ala Gly Cys Cys Ala Gly Cys Ala Ala Cys Ala Cys Cys
            610                 615                 620
Ala Ala Gly Gly Thr Gly Ala Cys Ala Gly Ala Cys Ala Gly
625                 630                 635                 640
Thr Thr Gly Ala Gly Gly Cys Ala Ala Thr Gly Thr Thr Gly
                645                 650                 655
Thr Gly Thr Cys Gly Ala Gly Thr Gly Cys Cys Ala Cys Cys Gly
                660                 665                 670
Thr Gly Cys Cys Ala Gly Cys Ala Cys Cys Ala Cys Cys Thr Gly
                675                 680                 685
Thr Gly Gly Cys Ala Gly Gly Ala Cys Cys Gly Thr Cys Ala Gly Thr
            690                 695                 700
Cys Thr Thr Cys Cys Thr Cys Thr Thr Cys Cys Cys Cys Cys Ala
705                 710                 715                 720
Ala Ala Ala Cys Cys Cys Ala Ala Gly Gly Ala Cys Ala Cys Cys Cys
                725                 730                 735
Thr Cys Ala Thr Gly Ala Thr Cys Thr Cys Cys Cys Gly Gly Ala Cys
            740                 745                 750
Cys Cys Cys Thr Gly Ala Gly Gly Thr Cys Ala Cys Gly Thr Gly Cys
            755                 760                 765
Gly Thr Gly Gly Thr Gly Gly Thr Gly Gly Ala Cys Gly Thr Gly Ala
            770                 775                 780
Gly Cys Cys Ala Cys Gly Ala Ala Gly Ala Cys Cys Cys Gly Ala
785                 790                 795                 800
Gly Gly Thr Cys Cys Ala Gly Thr Thr Cys Ala Ala Cys Thr Gly Gly
                805                 810                 815
Thr Ala Cys Gly Thr Gly Gly Ala Cys Gly Gly Cys Gly Thr Gly Gly
                820                 825                 830
Ala Gly Gly Thr Gly Cys Ala Thr Ala Ala Thr Gly Cys Cys Ala Ala
            835                 840                 845
Gly Ala Cys Ala Ala Gly Cys Cys Ala Cys Gly Gly Gly Ala Gly
            850                 855                 860
Gly Ala Gly Cys Ala Gly Thr Thr Cys Ala Ala Cys Ala Gly Cys Ala
865                 870                 875                 880
Cys Gly Thr Thr Cys Cys Gly Thr Gly Thr Gly Gly Thr Cys Ala Gly
                885                 890                 895
Cys Gly Thr Cys Cys Thr Cys Ala Cys Cys Gly Thr Cys Gly Thr Gly
                900                 905                 910
Cys Ala Cys Cys Ala Gly Gly Ala Cys Thr Gly Gly Cys Thr Gly Ala
            915                 920                 925
Ala Cys Gly Gly Cys Ala Ala Gly Gly Ala Gly Thr Ala Cys Ala Ala
            930                 935                 940
Gly Thr Gly Cys Ala Ala Gly Gly Thr Gly Thr Cys Cys Ala Ala Cys
945                 950                 955                 960
Ala Ala Ala Gly Gly Cys Cys Thr Cys Cys Cys Ala Gly Cys Cys Cys
                965                 970                 975
Cys Cys Ala Thr Cys Gly Ala Gly Ala Ala Ala Ala Cys Cys Ala Thr
            980                 985                 990
```

```
Cys Thr Cys Cys Ala Ala Ala Ala  Cys Cys Ala Ala Ala  Gly Gly Gly
        995                 1000                 1005

Cys Ala  Gly Cys Cys Cys Cys  Gly Ala Gly Ala   Cys Cys Ala
    1010             1015                  1020

Cys Ala  Gly Gly Thr Gly Thr  Ala Cys Ala Cys   Cys Thr Gly
    1025             1030                  1035

Cys Cys  Cys Cys Cys Ala Thr  Cys Cys Cys Gly   Gly Ala Gly
    1040             1045                  1050

Gly Ala  Gly Ala Thr Gly Ala  Cys Cys Ala Ala   Gly Ala Cys
    1055             1060                  1065

Cys Ala  Gly Gly Thr Cys Ala  Gly Cys Cys Thr   Gly Ala Cys Cys
    1070             1075                  1080

Thr Gly  Cys Cys Thr Gly Gly  Thr Cys Ala Ala   Gly Gly Cys
    1085             1090                  1095

Thr Thr  Cys Thr Ala Cys Cys  Cys Cys Ala Gly   Cys Gly Ala Cys
    1100             1105                  1110

Ala Thr  Cys Gly Cys Cys Gly  Thr Gly Ala Gly   Thr Gly Gly
    1115             1120                  1125

Gly Ala  Gly Ala Gly Cys Ala  Ala Thr Gly Gly   Cys Ala Gly
    1130             1135                  1140

Cys Cys  Gly Gly Ala Gly Ala  Ala Cys Ala Ala   Cys Thr Ala Cys
    1145             1150                  1155

Ala Ala  Cys Ala Cys Cys Ala  Cys Ala Cys Cys   Thr Cys Cys
    1160             1165                  1170

Ala Thr  Gly Cys Thr Gly Gly  Ala Cys Thr Cys   Cys Gly Ala Cys
    1175             1180                  1185

Gly Gly  Cys Thr Cys Cys Thr  Thr Cys Thr Thr   Cys Thr Cys
    1190             1195                  1200

Thr Ala  Cys Ala Gly Cys Ala  Ala Gly Cys Thr   Ala Cys Cys
    1205             1210                  1215

Gly Thr  Gly Gly Ala Cys Ala  Ala Gly Ala Gly   Cys Ala Gly Gly
    1220             1225                  1230

Thr Gly  Gly Cys Ala Gly Cys  Ala Gly Gly Gly   Ala Ala Cys
    1235             1240                  1245

Gly Thr  Cys Thr Thr Cys Thr  Cys Ala Thr Gly   Cys Thr Cys Cys
    1250             1255                  1260

Gly Thr  Gly Ala Thr Gly Cys  Ala Thr Gly Ala   Gly Gly Cys Thr
    1265             1270                  1275

Cys Thr  Gly Cys Ala Cys Ala  Ala Cys Cys Ala   Cys Thr Ala Cys
    1280             1285                  1290

Ala Cys  Gly Cys Ala Gly Ala  Ala Gly Ala Gly   Cys Cys Thr Cys
    1295             1300                  1305

Thr Cys  Cys Cys Thr Gly Thr  Cys Thr Cys Cys   Gly Gly Gly Thr
    1310             1315                  1320

Ala Ala Ala
    1325

<210> SEQ ID NO 116
<211> LENGTH: 1329
<212> TYPE: PRT
<213> ORGANISM: Artificial Sequence
<220> FEATURE:
<223> OTHER INFORMATION: complete heavy chain

<400> SEQUENCE: 116
```

```
Cys Ala Gly Gly Thr Gly Cys Ala Gly Cys Thr Cys Ala Gly Gly
1               5                   10                  15

Ala Gly Thr Cys Gly Gly Cys Cys Ala Gly Ala Cys Thr
            20              25              30

Gly Gly Thr Gly Ala Ala Gly Cys Cys Thr Thr Cys Ala Cys Ala Gly
            35              40                  45

Ala Cys Cys Cys Thr Gly Thr Cys Cys Thr Cys Ala Cys Thr
    50              55                  60

Gly Cys Ala Cys Thr Gly Thr Cys Thr Cys Thr Gly Gly Cys Thr Ala
65              70              75              80

Cys Ala Cys Cys Thr Thr Cys Ala Cys Ala Ala Cys Thr Ala Cys
                85              90                  95

Thr Ala Thr Gly Thr Ala Thr Thr Cys Thr Gly Gly Gly Thr Gly Cys
            100             105             110

Gly Ala Cys Ala Gly Gly Cys Thr C

```
Cys Gly Cys Cys Cys Thr Gly Gly Cys Thr Gly Cys Thr Gly
            420                 425             430

Gly Thr Cys Ala Ala Gly Gly Ala Cys Thr Ala Cys Thr Cys Cys
            435             440             445

Cys Cys Gly Ala Ala Cys Cys Gly Gly Thr Gly Ala Cys Gly Gly Thr
            450             455             460

Gly Thr Cys Gly Thr Gly Gly Ala Ala Cys Thr Cys Ala Gly Gly Cys
465             470             475             480

Gly Cys Cys Cys Thr Gly Ala Cys Cys Ala Gly Gly Cys Gly
            485             490             495

Thr Gly Cys Ala Cys Ala Cys Cys Thr Thr Cys Cys Cys Gly Gly Cys
            500             505             510

Thr Gly Thr Cys Cys Thr Ala Cys Ala Gly Thr Cys Cys Thr Cys Ala
            515             520             525

Gly Gly Ala Cys Thr Cys Thr Ala Cys Thr Cys Cys Cys Thr Cys Ala
            530             535             540

Gly Cys Ala Gly Cys Gly Thr Gly Gly Thr Gly Ala Cys Cys Gly Thr
545             550             555             560

Gly Cys Cys Cys Thr Cys Cys Ala Gly Cys Ala Gly Cys Thr Thr Gly
            565             570             575

Gly Gly Cys Ala Cys Gly Ala Ala Gly Ala Cys Cys Thr Ala Cys Ala
            580             585             590

Cys Cys Thr Gly Cys Ala Ala Cys Gly Thr Ala Gly Ala Thr Cys Ala
            595             600             605

Cys Ala Ala Gly Cys Cys Cys Ala Gly Cys Ala Ala Cys Ala Cys Cys
            610             615             620

Ala Ala Gly Gly Thr Gly Gly Ala Cys Ala Ala Gly Ala Gly Ala Gly
625             630             635             640

Thr Thr Gly Ala Gly Thr Cys Cys Ala Ala Ala Thr Ala Thr Gly Gly
            645             650             655

Thr Cys Cys Cys Cys Cys Ala Thr Gly Cys Cys Cys Ala Cys Cys Gly
            660             665             670

Thr Gly Cys Cys Cys Ala Gly Cys Ala Cys Cys Thr Gly Ala Gly Thr
            675             680             685

Thr Cys Cys Thr Gly Gly Gly Gly Gly Gly Ala Cys Cys Ala Thr Cys
            690             695             700

Ala Gly Thr Cys Thr Thr Cys Cys Thr Gly Thr Thr Cys Cys Cys Cys
705             710             715             720

Cys Cys Ala Ala Ala Ala Cys Cys Cys Ala Ala Gly Gly Ala Cys Ala
            725             730             735

Cys Thr Cys Thr Cys Ala Thr Gly Ala Thr Cys Thr Cys Cys Cys Gly
            740             745             750

Gly Ala Cys Cys Cys Cys Thr Gly Ala Gly Gly Thr Cys Ala Cys Gly
            755             760             765

Thr Gly Cys Gly Thr Gly Gly Thr Gly Gly Thr Gly Gly Ala Cys Gly
            770             775             780

Thr Gly Ala Gly Cys Cys Ala Gly Gly Ala Ala Gly Ala Cys Cys Cys
785             790             795             800

Cys Gly Ala Gly Gly Thr Cys Cys Ala Gly Thr Thr Cys Ala Ala Cys
            805             810             815

Thr Gly Gly Thr Ala Cys Gly Thr Gly Gly Ala Thr Gly Gly Cys Gly
            820             825             830

Thr Gly Gly Ala Gly Gly Thr Gly Cys Ala Thr Ala Ala Thr Gly Cys
```

```
                835                 840                 845
Cys Ala Ala Gly Ala Cys Ala Ala Gly Cys Cys Gly Cys Gly Gly
    850                 855                 860
Gly Ala Gly Gly Ala Gly Cys Ala Gly Thr Thr Cys Ala Ala Cys Ala
865                 870                 875                 880
Gly Cys Ala Cys Gly Thr Ala Cys Cys Gly Thr Gly Thr
                885                 890                 895
Cys Ala Gly Cys Gly Thr Cys Cys Thr Cys Ala Cys Cys Gly Thr Cys
            900                 905                 910
Cys Thr Gly Cys Ala Cys Cys Ala Gly Ala Cys Thr Gly Gly Cys
            915                 920                 925
Thr Gly Ala Ala Cys Gly Gly Cys Ala Ala Gly Gly Ala Gly Thr Ala
    930                 935                 940
Cys Ala Ala Gly Thr Gly Cys Ala Ala Gly Gly Thr Gly Thr Cys Cys
945                 950                 955                 960
Ala Ala Cys Ala Ala Ala Gly Gly Cys Cys Thr Cys Cys Cys Gly Thr
                965                 970                 975
Cys Cys Thr Cys Cys Ala Thr Cys Gly Ala Gly Ala Ala Ala Ala Cys
            980                 985                 990
Cys Ala Thr Cys Thr Cys Cys Ala  Ala Ala Gly Cys Cys Ala Ala Ala
            995                1000                1005
Gly Gly  Gly Cys Ala Gly Cys  Cys Cys Gly Ala  Gly Ala Gly
    1010                1015                1020
Cys Cys  Ala Cys Ala Gly Gly  Thr Gly Thr Ala Cys  Ala Cys Cys
    1025                1030                1035
Cys Thr  Gly Cys Cys Cys Cys  Ala Thr Cys Cys  Cys Ala Gly
    1040                1045                1050
Gly Ala  Gly Gly Ala Gly Ala  Thr Gly Ala Cys Cys  Ala Ala Gly
    1055                1060                1065
Ala Ala  Cys Cys Ala Gly Gly  Thr Cys Ala Gly Cys  Cys Thr Gly
    1070                1075                1080
Ala Cys  Cys Thr Gly Cys Cys  Thr Gly Gly Thr Cys  Ala Ala Ala
    1085                1090                1095
Gly Gly  Cys Thr Thr Cys Thr  Ala Cys Cys Cys Ala Gly Cys
    1100                1105                1110
Gly Ala Cys  Cys Ala Thr Cys Gly  Cys Cys Gly Thr Gly  Gly Ala Gly
    1115                1120                1125
Thr Gly  Gly Gly Ala Gly Ala  Gly Cys Ala Ala Thr  Gly Gly Gly
    1130                1135                1140
Cys Ala  Gly Cys Cys Gly Gly  Ala Gly Ala Ala Cys  Ala Ala Cys
    1145                1150                1155
Thr Ala  Cys Ala Ala Gly Ala  Cys Cys Ala Cys Gly  Cys Cys Thr
    1160                1165                1170
Cys Cys  Cys Gly Thr Gly Cys  Thr Gly Gly Ala Cys  Thr Cys Cys
    1175                1180                1185
Gly Ala  Cys Gly Gly Cys Thr  Cys Cys Thr Thr Cys  Thr Thr Cys
    1190                1195                1200
Cys Thr  Cys Thr Ala Cys Ala  Gly Cys Ala Gly Gly  Cys Thr Ala
    1205                1210                1215
Ala Cys  Cys Gly Thr Gly Gly  Ala Cys Ala Ala Gly  Ala Gly Cys
    1220                1225                1230
Ala Gly  Gly Thr Gly Gly Cys  Ala Gly Gly Ala Gly  Gly Gly Gly
    1235                1240                1245
```

```
Ala Ala  Thr Gly Thr Cys  Thr Cys Thr Cys  Ala  Thr Gly Cys
    1250             1255              1260

Thr Cys  Cys Gly Thr Gly  Ala  Thr Gly Cys  Ala  Thr  Gly Ala Gly
    1265              1270              1275

Gly Cys  Thr Cys Thr Gly  Cys  Ala Cys Ala  Ala  Cys  Cys Ala Cys
    1280              1285              1290

Thr Ala  Cys Ala Cys Ala  Cys  Ala Gly Ala  Ala  Gly  Ala Gly Cys
    1295              1300              1305

Cys Thr  Cys Thr Cys Cys  Thr  Gly Thr Cys  Thr  Cys  Thr Gly
    1310              1315              1320

Gly Gly  Thr Ala Ala Ala
    1325
```

<210> SEQ ID NO 117
<211> LENGTH: 113
<212> TYPE: PRT
<213> ORGANISM: Artificial Sequence
<220> FEATURE:
<223> OTHER INFORMATION: light chain constant region

<400> SEQUENCE: 117

```
Thr Lys Val Glu Ile Lys Arg Thr Val Ala Ala Pro Ser Val Phe Ile
1               5                   10                  15

Phe Pro Pro Ser Asp Glu Gln Leu Lys Ser Gly Thr Ala Ser Val Val
            20                  25                  30

Cys Leu Leu Asn Asn Phe Tyr Pro Arg Glu Ala Lys Val Gln Trp Lys
        35                  40                  45

Val Asp Asn Ala Leu Gln Ser Gly Asn Ser Gln Glu Ser Val Thr Glu
    50                  55                  60

Gln Asp Ser Lys Asp Ser Thr Tyr Ser Leu Ser Ser Thr Leu Thr Leu
65                  70                  75                  80

Ser Lys Ala Asp Tyr Glu Lys His Lys Val Tyr Ala Cys Glu Val Thr
                85                  90                  95

His Gln Gly Leu Ser Ser Pro Val Thr Lys Ser Phe Asn Arg Gly Glu
            100                 105                 110

Cys
```

<210> SEQ ID NO 118
<211> LENGTH: 337
<212> TYPE: PRT
<213> ORGANISM: Artificial Sequence
<220> FEATURE:
<223> OTHER INFORMATION: heavy chain constant region

<400> SEQUENCE: 118

```
Thr Leu Val Thr Val Ser Ser Ala Ser Thr Lys Gly Pro Ser Val Phe
1               5                   10                  15

Pro Leu Ala Pro Ser Ser Lys Ser Thr Ser Gly Gly Thr Ala Ala Leu
            20                  25                  30

Gly Cys Leu Val Lys Asp Tyr Phe Pro Glu Pro Val Thr Val Ser Trp
        35                  40                  45

Asn Ser Gly Ala Leu Thr Ser Gly Val His Thr Phe Pro Ala Val Leu
    50                  55                  60

Gln Ser Ser Gly Leu Tyr Ser Leu Ser Ser Val Val Thr Val Pro Ser
65                  70                  75                  80

Ser Ser Leu Gly Thr Gln Thr Tyr Ile Cys Asn Val Asn His Lys Pro
                85                  90                  95
```

```
Ser Asn Thr Lys Val Asp Lys Lys Val Glu Pro Lys Ser Cys Asp Lys
            100                 105                 110

Thr His Thr Cys Pro Pro Cys Pro Ala Pro Glu Leu Leu Gly Gly Pro
            115                 120                 125

Ser Val Phe Leu Phe Pro Pro Lys Pro Lys Asp Thr Leu Met Ile Ser
130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
            195                 200                 205

Tyr Lys Cys Lys Val Ser Asn Lys Ala Leu Pro Ala Pro Ile Glu Lys
            210                 215                 220

Thr Ile Ser Lys Ala Lys Gly Gln Pro Arg Glu Pro Gln Val Tyr Thr
225                 230                 235                 240

Leu Pro Pro Ser Arg Asp Glu Leu Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
            275                 280                 285

Asp Ser Asp Gly Ser Phe Phe Leu Tyr Ser Lys Leu Thr Val Asp Lys
290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys

<210> SEQ ID NO 119
<211> LENGTH: 245
<212> TYPE: PRT
<213> ORGANISM: Artificial Sequence
<220> FEATURE:
<223> OTHER INFORMATION: heavy chain constant region

<400> SEQUENCE: 119

Thr Leu Val Thr Val Ser Ser Ala Ser Thr Lys Gly Pro Ser Val Phe
1               5                   10                  15

Pro Leu Ala Pro Ser Ser Lys Ser Thr Ser Gly Gly Thr Ala Ala Leu
            20                  25                  30

Gly Cys Leu Val Lys Asp Tyr Phe Pro Glu Pro Val Thr Val Ser Trp
        35                  40                  45

Asn Ser Gly Ala Leu Thr Ser Gly Val His Thr Phe Pro Ala Val Leu
    50                  55                  60

Gln Ser Ser Gly Leu Tyr Ser Leu Ser Ser Val Val Thr Val Pro Ser
65                  70                  75                  80

Ser Ser Leu Gly Thr Gln Thr Tyr Ile Cys Asn Val Asn His Lys Pro
                85                  90                  95

Ser Asn Thr Lys Val Asp Lys Lys Val Glu Pro Lys Ser Cys Asp Lys
            100                 105                 110
```

```
Thr His Thr Cys Pro Pro Cys Pro Ala Pro Glu Leu Leu Gly Gly Pro
        115                 120                 125

Ser Val Phe Leu Phe Pro Pro Lys Pro Lys Asp Thr Leu Met Ile Ser
130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Gln Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
    210                 215                 220

Thr Ile Ser Lys Ala Lys Gly Gln Pro Arg Glu Pro Gln Val Tyr Thr
225                 230                 235                 240

Leu Pro Pro Ser Arg
                245

<210> SEQ ID NO 120
<211> LENGTH: 337
<212> TYPE: PRT
<213> ORGANISM: Artificial Sequence
<220> FEATURE:
<223> OTHER INFORMATION: heavy chain constant region

<400> SEQUENCE: 120

Trp Gly Gln Gly Thr Leu Val Thr Val Ser Ser Ala Ser Thr Lys Gly
1               5                   10                  15

Pro Ser Val Phe Pro Leu Ala Pro Cys Ser Arg Ser Thr Ser Glu Ser
            20                  25                  30

Thr Ala Ala Leu Gly Cys Leu Val Lys Asp Tyr Phe Pro Glu Pro Val
        35                  40                  45

Thr Val Ser Trp Asn Ser Gly Ala Leu Thr Ser Gly Val His Thr Phe
    50                  55                  60

Pro Ala Val Leu Gln Ser Ser Gly Leu Tyr Ser Leu Ser Ser Val Val
65                  70                  75                  80

Thr Val Pro Ser Ser Asn Phe Gly Thr Gln Thr Tyr Thr Cys Asn Val
                85                  90                  95

Asp His Lys Pro Ser Asn Thr Lys Val Asp Lys Thr Val Glu Arg Lys
            100                 105                 110

Cys Cys Val Glu Cys Pro Pro Cys Pro Ala Pro Pro Val Ala Gly Pro
        115                 120                 125

Ser Val Phe Leu Phe Pro Pro Lys Pro Lys Asp Thr Leu Met Ile Ser
130                 135                 140

Arg Thr Pro Glu Val Thr Cys Val Val Val Asp Val Ser His Glu Asp
145                 150                 155                 160

Pro Glu Val Gln Phe Asn Trp Tyr Val Asp Gly Val Glu Val His Asn
                165                 170                 175

Ala Lys Thr Lys Pro Arg Glu Glu Gln Phe Asn Ser Thr Phe Arg Val
            180                 185                 190

Val Ser Val Leu Thr Val Val His Gln Asp Trp Leu Asn Gly Lys Glu
        195                 200                 205

Tyr Lys Cys Lys Val Ser Asn Lys Gly Leu Pro Ala Pro Ile Glu Lys
    210                 215                 220
```

```
Thr Ile Ser Lys Thr Lys Gly Gln Pro Arg Glu Pro Gln Val Tyr Thr
225                 230                 235                 240

Leu Pro Pro Ser Arg Glu Glu Met Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Asn Thr Thr Pro Pro Met Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys

<210> SEQ ID NO 121
<211> LENGTH: 334
<212> TYPE: PRT
<213> ORGANISM: Artificial Sequence
<220> FEATURE:
<223> OTHER INFORMATION: heavy chain constant region

<400> SEQUENCE: 121

Thr Thr Val Thr Val Ser Ser Ala Ser Thr Lys Gly Pro Ser Val Phe
1               5                   10                  15

Pro Leu Ala Pro Cys Ser Arg Ser Thr Ser Glu Ser Thr Ala Ala Leu
            20                  25                  30

Gly Cys Leu Val Lys Asp Tyr Phe Pro Glu Pro Val Thr Val Ser Trp
        35                  40                  45

Asn Ser Gly Ala Leu Thr Ser Gly Val His Thr Phe Pro Ala Val Leu
    50                  55                  60

Gln Ser Ser Gly Leu Tyr Ser Leu Ser Ser Val Val Thr Val Pro Ser
65                  70                  75                  80

Ser Ser Leu Gly Thr Lys Thr Tyr Thr Cys Asn Val Asp His Lys Pro
                85                  90                  95

Ser Asn Thr Lys Val Asp Lys Arg Val Glu Ser Lys Tyr Gly Pro Pro
            100                 105                 110

Cys Pro Pro Cys Pro Ala Pro Glu Phe Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser Gln Glu Asp Pro Glu Val
145                 150                 155                 160

Gln Phe Asn Trp Tyr Val Asp Gly Val Glu Val His Asn Ala Lys Thr
                165                 170                 175

Lys Pro Arg Glu Glu Gln Phe Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Gly Leu Pro Ser Ser Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Gln Glu Glu Met Thr Lys Asn Gln Val Ser Leu Thr Cys Leu Val
```

-continued

```
                245                 250                 255
Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Arg Leu Thr Val Asp Lys Ser Arg Trp
    290                 295                 300

Gln Glu Gly Asn Val Phe Ser Cys Ser Val Met His Glu Ala Leu His
305                 310                 315                 320

Asn His Tyr Thr Gln Lys Ser Leu Ser Leu Ser Leu Gly Lys
                325                 330
```

THERAPEUTIC CD47 ANTIBODIES

CROSS REFERENCE TO RELATED APPLICATIONS

This application is a Continuation of U.S. application Ser. No. 14/302,348, filed Jun. 11, 2014, which is a continuation-in-part of PCT/US2013/074766, filed Dec. 12, 2013, U.S. Provisional Application Ser. No. 61/833,691, filed Jun. 11, 2013, and U.S. Provisional Application Ser. No. 61/736,301, filed Dec. 12, 2012, the contents of each of which are herein incorporated by reference in their entirety.

BACKGROUND

The present disclosure relates to antibodies that bind CD47, including that of humans and other mammalian species, and their use in treating conditions and disorders, such as ischemia-reperfusion injury (IRI) and cancers, mediated by this receptor.

CD47 is a cell surface receptor comprised of an extracellular IgV set domain, a 5 membrane spanning transmembrane domain, and a cytoplasmic tail that is alternatively spliced. Two ligands bind CD47: thrombospondin-1 (TSP1), and signal inhibitory receptor protein alpha (SIRPalpha). TSP1 binding to CD47 activates the heterotrimeric G protein Gi, which leads to suppression of intracellular cyclic AMP (cAMP) levels. In addition, the TSP1-CD47 pathway opposes the beneficial effects of the nitric oxide pathway in all vascular cells. The nitric oxide (NO) pathway consists of any of three nitric oxide synthase enzymes (NOS I, NOS II and NOS III) that generate bioactive gas NO using arginine as a substrate. NO can act within the cell in which it is produced, or in neighboring cells, to activate the enzyme soluble guanylyl cyclase that produces the messenger molecule cyclic GMP (cGMP). The proper functioning of the NO-cGMP pathway is essential for protecting the cardiovascular system against stresses including, but not limited to, those resulting from wounding, inflammation, hypertension, metabolic syndrome, ischemia, and ischemia-reperfusion injury (IRI). In the context of these cellular stresses, the inhibition of the NO-cGMP pathway by the TSP1-CD47 system exacerbates the effects of stress. This is a particular problem in the cardiovascular system where both cGMP and cAMP play important protective roles. There are many cases in which ischemia and reperfusion injury cause or contribute to disease, trauma, and poor outcomes of surgical procedures.

SIRPalpha is expressed on hematopoietic cells, including macrophages and dendritic cells. When it engages CD47 on a potential phagocytic target cell, phagocytosis is slowed or prevented. The CD47-SIRPalpha interaction effectively sends a "don't eat me" signal to the phagocyte. Thus, blocking the SIRPalpha-CD47 interaction with a monoclonal antibody in this therapeutic context can provide an effective anti-cancer therapy by promoting, i.e., increasing, the uptake and clearance of cancer cells by the host's immune system by increasing phagocytosis, This mechanism is effective in leukemias, lymphomas and many types of solid tumors.

U.S. Pat. No. 8,236,313 contemplates antibodies that could be useful in the field of ischemia and blood flow to reverse and/or prevent tissue ischemia and related and associated tissue and cell damage, including antibodies that block CD47.

U.S. Pat. No. 8,101,719 discloses humanized antibodies that bind to CD47 for use in treating hematological disorders. Objects of the invention include humanized anti-CD47 antibodies and small antibody fragments exhibiting reduced antigenicity while retaining their CD47 binding activity and apoptosis-inducing activity. Such antibodies and small fragments are contemplated for use in treating hematological disorders such as various types of leukemias, malignant lymphoma, aplastic anemia, myeodysplastic syndromes, and polycythemia vera.

PCT International Publication WO 2011/143624 discloses chimeric and humanized anti-CD47 monoclonal antibodies for use as reagents for the diagnosis and immunotherapy of diseases associated with CD47 in humans, particularly in cancer therapy, for example to increase phagocytosis of cancer cells expressing CD47. Preferred antibodies are non-activating, i.e., block ligand binding, but do not signal. Disclosed humanized B6H12 and 5F9 antibodies bound soluble human CD47; B6H12 also bound human CD47 on the surface of human CD47-transfected YB2/0 cells. Humanized B6H12 and 5F9 antibodies enabled phagocytosis of CFSE-labeled HL-60 cells by mouse bone marrow- or peripheral blood-derived macrophages in vitro, respectively. Humanized B6H12 utilized human VH-3-7 and VK3-11 frameworks.

U.S. 2013/0142786 discloses non-activating anti-CD47 antibodies that increase the phagocytosis of CD47 expressing cells.

PCT International Publication WO 2013/119714 discloses anti-CD47 antibodies that do not cause a significant level of hemagglutination of human red blood cells.

There exists a need for antibodies to human CD47 that selectively block the binding of TSP1 to CD47 to promote the beneficial effects of nitric oxide-cGMP signaling and cAMP signaling in the cardiovascular system in settings in which IRI plays a role in pathogenesis. These situations/diseases include organ transplantation, acute kidney injury, cardiopulmonary bypass surgery, pulmonary hypertension, sickle cell disease, myocardial infarction, stroke, surgical resections and reconstructive surgery, reattachment of digits/body parts, skin grafting, and trauma. There is also a need for antibodies that block the binding of SIRPalpha to CD47, thus providing novel anti-cancer therapies.

SUMMARY

Antibody compounds disclosed herein meet these needs by exhibiting the following desirable therapeutic activities:
Binding to CD47 of multiple mammalian species;
Blocking SIRPalpha and TSP1 binding to CD47;
Promoting phagocytosis of cancer cells; and
Reversing TSP1 inhibition of nitric oxide signaling.

The present antibodies are useful in reducing, preventing, and/or treating CD47-mediated diseases or conditions (e.g., ischemia reperfusion injury and cancers).

They likely bind to epitopes in the extracellular IgV domain of CD47, inhibiting TSP1 and SIRPalpha binding to CD47 and receptor activation, while inducing little or no agonist activity and promoting tumor cell phagocytic clearance. In view of these properties, antibody compounds of the present disclosure should be therapeutically useful in treating many forms of IRI and cancers.

In addition, the present antibody compounds can possess a number of other desirable properties, including broad reactivity with CD47 of a wide variety of mammalian species, including that of human, mouse, rat, pig, cynomolgus monkey, and dog, making these antibodies useful in both human and veterinary medicine. This feature is further advantageous in that it facilitates preclinical studies including, but not limited to, safety and efficacy studies, in a variety of mammalian species, and therefore the development of such antibodies as human and veterinary therapeutics.

Accordingly, the present disclosure provides:

[1] A monoclonal antibody, or antigen-binding fragment thereof, that:
(i) specifically binds human, rat, mouse, pig, cynomolgus monkey, and dog CD47;
(ii) blocks SIRPalpha and TSP1 binding to CD47;
(iii) promotes phagocytosis of cancer cells; and
(iv) reverses TSP1 inhibition of nitric oxide signaling.

[2] The monoclonal antibody or antigen-binding fragment thereof of [1], which is chimeric or humanized.

[3] The monoclonal antibody, or antigen-binding fragment thereof, of [1] or [2], which comprises three light chain complementarity determining regions (LCDRs 1-3) and three heavy chain complementarity determining regions (HCDRs 1-3), wherein:
LCDR 1 comprises the amino acid sequence RSSQSLVHSNGNTYLH (SEQ ID NO:1) LCDR 2 comprises the amino acid sequence KVSYRFS (SEQ ID NO:2); and
LCDR 3 comprises the amino acid sequence SQNTHVPRT (SEQ ID NO:3);
HCDR1 comprises the amino acid sequence GYTFTNYYVF (SEQ ID NO:4);
HCDR 2 comprises the amino acid sequence DINPVNGDTNFNEKFKN (SEQ ID NO:5); and
HCDR 3 comprises the amino acid sequence GGYTMDY (SEQ ID NO:6).

[4] The monoclonal antibody, or antigen-binding fragment thereof, of any one of [1]-[3], which comprises a light chain variable region (LCVR) and a heavy chain variable region (HCVR), wherein said LCVR and said HCVR comprise, respectively, amino acid sequences selected from among the following combinations of LCVRs and HCVRs:
SEQ ID NO:7 and SEQ ID NO:57;
SEQ ID NO:8 and SEQ ID NO:58;
SEQ ID NO:9 and SEQ ID NO:59;
SEQ ID NO:10 and SEQ ID NO:60;
SEQ ID NO:11 and SEQ ID NO:61;
SEQ ID NO:12 and SEQ ID NO:62;
SEQ ID NO:13 and SEQ ID NO:63;
SEQ ID NO:14 and SEQ ID NO:64;
SEQ ID NO:15 and SEQ ID NO:65;
SEQ ID NO:16 and SEQ ID NO:66;
SEQ ID NO:17 and SEQ ID NO:67;
SEQ ID NO:18 and SEQ ID NO:68;
SEQ ID NO:19 and SEQ ID NO:69;
SEQ ID NO:20 and SEQ ID NO:70;
SEQ ID NO:21 and SEQ ID NO:71;
SEQ ID NO:22 and SEQ ID NO:72;
SEQ ID NO:23 and SEQ ID NO:73;
SEQ ID NO:24 and SEQ ID NO:74;
SEQ ID NO:25 and SEQ ID NO:75;
SEQ ID NO:26 and SEQ ID NO:76;
SEQ ID NO:27 and SEQ ID NO:77;
SEQ ID NO:28 and SEQ ID NO:78;
SEQ ID NO:29 and SEQ ID NO:79;
SEQ ID NO:30 and SEQ ID NO:80; and
SEQ ID NO:31 and SEQ ID NO:81,
wherein each one of LCVR SEQ ID NOs:7-31 further comprises a constant domain having the amino acid sequence shown in SEQ ID NO:117, and
wherein each one of HCVR SEQ ID NOs:57-81 comprises a constant domain selected from among SEQ ID NO:118, SEQ ID NO:119, SEQ ID NO:120, and SEQ ID NO:121.

[5] A monoclonal antibody, or antigen-binding fragment thereof, that competes with said monoclonal antibody or antigen-binding fragment thereof of any one of [1]-[4] for binding to CD47, especially human CD47.

[6] A pharmaceutical composition, comprising said monoclonal antibody or antigen-binding fragment thereof, or competing antibody or antigen binding fragment thereof, of any one of [1]-[5], and a pharmaceutically or physiologically acceptable carrier, diluent, or excipient.

[7] A monoclonal antibody or antigen-binding fragment thereof, or competing antibody or antigen binding fragment thereof, of any one of [1]-[5] for use in human therapy or therapy of companion/pet animals, working animals, sport animals, zoo animals, or therapy of other valuable animals kept in captivity.

[8] The monoclonal antibody or antigen-binding fragment thereof, or competing antibody or antigen binding fragment thereof, of any one of [1]-[5] for use in treating ischemia-reperfusion injury, or an autoimmune or inflammatory disease, in a human or companion/pet animal, working animal, sport animal, zoo animal, or other valuable animal kept in captivity.

[9] The monoclonal antibody or antigen-binding fragment thereof, or competing antibody or antigen binding fragment thereof, of [8], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, or trauma.

[10] The monoclonal antibody, or antigen-binding fragment thereof, or competing antibody or antigen binding fragment thereof, of [8], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[11] The monoclonal antibody or antigen-binding fragment thereof, or competing antibody or antigen binding fragment thereof, of any one of [1]-[5] for use in treating a susceptible cancer.

[12] The monoclonal antibody or antigen binding fragment thereof, or competing antibody or antigen binding fragment thereof, of [11], which promotes phagocytosis of cells of said susceptible cancer.

[13] The monoclonal antibody or antigen binding fragment thereof, or competing antibody or antigen binding fragment thereof, of [11] or [12], wherein said susceptible cancer is selected from the group consisting of a leukemia, a lymphoma, ovarian cancer, breast cancer, endometrial cancer, colon cancer, rectal cancer, gastric cancer, bladder cancer, lung cancer, bronchial cancer, bone cancer, prostate cancer, pancreatic cancer, liver and bile duct cancer, esophageal cancer, renal cancer, thyroid cancer, head and neck cancer, testicular cancer, glioblastoma, astrocytoma, melanoma, myelodysplastic syndrome, and a sarcoma.

[14] The monoclonal antibody or antigen binding fragment thereof, or competing antibody or antigen binding fragment thereof, of any one of [11]-[13], wherein:

said leukemia is selected from the group consisting of acute lymphocytic (lymphoblastic) leukemia, acute myeloid leukemia, myelogenous leukemia, chronic lymphocytic leukemia, multiple myeloma, plasma cell leukemia, and chronic myeloid leukemia;

said lymphoma is selected from the group consisting of Hodgkin lymphoma and Non-Hodgkin lymphoma including B cell lymphoma, diffuse large B cell lymphoma, follicular lymphoma, mantle cell lymphoma, marginal zone B cell lymphoma, T cell lymphoma, and Waldenstrom macroglobulinemia; and said sarcoma is selected from the group consisting of osteosarcoma, Ewing sarcoma, leiomyosarcoma, synovial sarcoma, alveolar soft part sarcoma, angiosarcoma, liposarcoma, fibrosarcoma, rhabdomyosarcoma, and chrondrosarcoma.

[15] Use of said monoclonal antibody or antigen-binding fragment thereof, or competing antibody or antigen binding fragment thereof, of any one of [1]-[5] to treat ischemia-reperfusion injury, or an autoimmune or inflammatory disease, in a human or companion/pet animal, working animal, sport animal, zoo animal, or other valuable animal kept in captivity.

[16] Use of said monoclonal antibody or antigen-binding fragment thereof, or competing antibody or antigen binding fragment thereof, of any one of [1]-[5] to treat a susceptible cancer.

[17] Use of said monoclonal antibody or antigen-binding fragment thereof, or competing antibody or antigen binding fragment thereof, of any one of [1]-[5] for the manufacture of a medicament to treat ischemia-reperfusion injury, or an autoimmune or inflammatory disease, in a human or companion/pet animal, working animal, sport animal, zoo animal, or other valuable animal kept in captivity.

[18] The use of [17], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, and trauma.

[19] The use of [17] or [18], wherein said autoimmune or inflammatory disease is selected from among arthritis, multiple sclerosis, psoriasis, Crohn's disease, inflammatory bowel disease, lupus, Grave's disease and Hashimoto's thyroiditis, and ankylosing spondylitis.

[20] Use of said monoclonal antibody or antigen-binding fragment thereof, or competing antibody or antigen binding fragment thereof, of any one of [1]-[5] for the manufacture of a medicament to treat a susceptible cancer.

[21] A method of treating ischemia or ischemia-reperfusion injury in a patient in need thereof, comprising administering to said patient an effective amount of said monoclonal antibody or antigen-binding fragment thereof, or competing antibody or antigen binding fragment thereof, of any one of [1]-[5].

[22] The method of [21], wherein said patient is about to be subjected to, or is experiencing, ischemia or ischemia-reperfusion injury.

[23] The method of [21] or [22], wherein said patient is a human.

[24] The method of [21] or [22], wherein said patient is a companion/pet animal, working animal, sport animal, zoo animal, or other valuable animal kept in captivity.

[25] The method of any one of [21]-[24], wherein said ischemia occurs because said patient will undergo, or is undergoing, a surgery selected from the group consisting of integument surgery, soft tissue surgery, composite tissue surgery, cosmetic surgery, surgical resections, reconstructive surgery, skin graft surgery, and limb reattachment surgery.

[26] The method of [25], wherein said skin graft is an autograft.

[27] The method of any one of [21]-[24], wherein said ischemia occurs because said patient will undergo, or is undergoing, organ transplant surgery.

[28] The method of any one of [21]-[24], wherein said ischemia-reperfusion injury occurs in organ transplantation, acute kidney injury, cardiopulmonary bypass surgery, pulmonary hypertension, sickle cell disease, myocardial infarction, stroke, surgical resection, reconstructive surgery, reattachment of an appendage or other body part, or skin grafting.

[29] The method of any one of [21]-[28], wherein said monoclonal antibody or antigen-binding fragment thereof, or competing monoclonal antibody or antigen binding fragment thereof, is administered before, during, or after said subject undergoes ischemia or surgery, or a combination of any of these time periods.

[30] The method of any one of [21]-[29], further comprising administering to said patient an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

[31] The method of [30], wherein:
said nitric oxide donor or precursor is selected from the group consisting of NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine; and
said agent that inhibits cyclic nucleotide phosphodiesterases is selected from the group consisting of sildenafil, tadalafil, vardenafil udenafil, and avanafil.

[32] A method of increasing tissue perfusion in a subject in need thereof, comprising administering to said subject an effective amount of a monoclonal antibody, or antigen-binding fragment thereof, or competing antibody or antigen binding fragment thereof, of any one of [1]-[5].

[33] The method of [32], wherein said subject has, or is at risk of developing, at least one disease or condition selected from the group consisting of ischemia-reperfusion injury, myocardial infarction, myocardial ischemia, stroke, cerebral ischemia, sickle cell anemia, and pulmonary hypertension.

[34] The method of [32], wherein said subject has, or is at risk of developing, at least one disease or condition selected from the group consisting of hypertension, atherosclerosis, vasculopathy, ischemia secondary to diabetes, and peripheral vascular disease.

[35] The method of [32], wherein the need for increased tissue perfusion arises because said subject has had, is having, or will have, a surgery selected from the group consisting of integument surgery, soft tissue surgery, composite tissue surgery, skin graft surgery, resection of a solid organ, and reattachment or an appendage or other body part.

[36] The method of [35], wherein said skin graft is an autograft.

[37] The method of [32], wherein the need for increased tissue perfusion arises because said subject has had, is having, or will have, organ transplant surgery.

[38] The method of any one of [32]-[37], further comprising administering to said subject an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

[39] The method of [38], wherein:
said nitric oxide donor or precursor is selected from the group consisting of NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine; and
said agent that inhibits cyclic nucleotide phosphodiesterases is selected from the group consisting of sildenafil, tadalafil, vardenafil udenafil, and avanafil.

[40] A method of transplanting a donor organ from an organ donor to an organ recipient, comprising any single step, any combination of steps, or all steps selected from the group consisting of steps i)-iii):
  i) administering to said organ donor prior to, during, both prior to and during, after, or any combination thereof, donation of said donor organ an effective amount of said monoclonal antibody or antigen-binding fragment thereof of any one of [1]-[5], and/or a monoclonal antibody, or antigen-binding fragment thereof, that competes with said monoclonal antibody or antigen-binding fragment thereof of any one of [1]-[5] for binding to CD47;
  ii) contacting said donor organ prior to, during, both prior to and during, after, or any combination thereof, transplantation to said organ recipient, and an effective amount of said monoclonal antibody or antigen-binding fragment thereof of any one of [1]-[5], and/or a monoclonal antibody, or antigen-binding fragment thereof, that competes with said monoclonal antibody or antigen-binding fragment thereof of any one of [1]-[5] for binding to CD47; and
  iii) administering to said organ recipient prior to, during, both prior to and during, after, or any combination thereof, transplantation of said donor organ to said organ recipient, an effective amount of said monoclonal antibody or antigen-binding fragment thereof of any one of [1]-[5], and/or a monoclonal antibody, or antigen-binding fragment thereof, that competes with said monoclonal antibody or antigen-binding fragment thereof of any one of [1]-[5] for binding to CD47.

[41] The method of any one of [1]-[5], or monoclonal antibody, or antigen-binding fragment thereof, that competes with said monoclonal antibody or antigen-binding fragment thereof of any one of [1]-[5] for binding to CD47, reduces ischemia reperfusion injury in said donor organ.

[42] The method of [40] or [41], further comprising administering to said organ donor, said donor organ, said organ recipient, or any combination thereof, an effective amount of a nitric oxide donor, precursor, or both; a nitric oxide generating topical agent; an agent that activates soluble guanylyl cyclase; or an agent that inhibits cyclic nucleotide phosphodiesterases; or any combination of any of the foregoing.

[43] The method of [42], wherein:
said nitric oxide donor or precursor is selected from the group consisting of NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine; and
said agent that inhibits cyclic nucleotide phosphodiesterases is selected from the group consisting of sildenafil, tadalafil, vardenafil, udenafil, and avanafil.

[44] A method of treating an autoimmune or inflammatory disease in a patient in need thereof, comprising administering to said patient an effective amount of said monoclonal antibody, or antigen-binding fragment thereof, or competing antibody or antigen binding fragment thereof, of any one of [1]-[5].

[45] The method of [44], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[46] The method of [44] or [45], wherein said patient is a human.

[47] The method of [44] or [45], wherein said patient is a companion/pet animal, working animal, sport animal, zoo animal, or other valuable animal kept in captivity.

[48] The method of any one of [44]-[47], further comprising administering to said patient an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

[49] The method of [48], wherein:
said nitric oxide donor or precursor is selected from the group consisting of NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine; and
said agent that inhibits cyclic nucleotide phosphodiesterases is selected from the group consisting of sildenafil, tadalafil, vardenafil, udenafil, and avanafil.

[50] A method of treating a susceptible cancer in a human or companion/pet animal, working animal, sport animal, zoo animal, or other valuable animal kept in captivity in need thereof, comprising administering thereto an effective amount of a monoclonal antibody or antigen binding fragment thereof, or competing antibody or antigen binding fragment thereof, of any one of [1]-[5].

[51] The method of [50], wherein said susceptible cancer is selected from the group consisting of a leukemia, a lymphoma, ovarian cancer, breast cancer, endometrial cancer, colon cancer, rectal cancer, gastric cancer, bladder cancer, lung cancer, bronchial cancer, bone cancer, prostate cancer, pancreatic cancer, liver and bile duct cancer, esophageal cancer, renal cancer, thyroid cancer, head and neck cancer, testicular cancer, glioblastoma, astrocytoma, melanoma, myelodysplastic syndrome, and a sarcoma.

[52] The method of [51], wherein:
said leukemia is selected from the group consisting of acute lymphocytic (lymphoblastic) leukemia, acute myeloid leukemia, myelogenous leukemia, chronic lymphocytic leukemia, multiple myeloma, plasma cell leukemia, and chronic myeloid leukemia;
said lymphoma is selected from the group consisting of Hodgkin lymphoma and Non-Hodgkin lymphoma including B cell lymphoma, diffuse large B cell lymphoma, follicular lymphoma, mantle cell lymphoma, marginal zone B cell lymphoma, T cell lymphoma, and Waldenstrom macroglobulinemia; and
said sarcoma is selected from the group consisting of osteosarcoma, Ewing sarcoma, leiomyosarcoma, synovial sarcoma, alveolar soft part sarcoma, angiosarcoma, liposarcoma, fibrosarcoma, rhabdomyosarcoma, and chondrosarcoma.

[53] The method of any one of [50]-[52], wherein said monoclonal antibody or antigen-binding fragment thereof, or competing antibody or antigen binding fragment thereof, of any one of [1]-[5] increases phagocytosis of cells of said susceptible cancer.

[54] The method of [53], wherein said monoclonal antibody or antigen-binding fragment thereof, or competing antibody or antigen binding fragment thereof, of any one of [1]-[5], increases phagocytosis of cells of said susceptible cancer and inhibits SIRPalpha binding to CD47.

[55] A humanized monoclonal antibody, or antigen-binding fragment thereof, that specifically binds human CD47.

[56] The use or method of any one of [7], [11]-[14], [16], [20], or [50]-[54], further comprising administering to said patient an anti-tumor therapeutic treatment selected from the group consisting of surgery, radiation, an anti-tumor or anti-neoplastic agent, and combinations of any of the foregoing.

[57] The use or method of [56], wherein said an anti-tumor or anti-neoplastic agent is a small chemical molecule or a biologic therapeutic.

[58] The use or method of [57], wherein said small chemical molecule or biologic therapeutic is selected from the group consisting of an alkylating agent; an antimetabolite; a natural product; a miscellaneous agent used in cancer therapy; a hormone; an antagonist; a monoclonal antibody or antigen-binding fragment thereof; a cytokine; an antisense oligonucleotide; an siRNA; or a miRNA.

[59] A method of enhancing the therapeutic effect of a soluble guanylyl cyclase activator, comprising administering to a patient in need thereof:
  i) an effective amount of a soluble guanylyl cyclase activator, and
  ii) a monoclonal antibody or antigen-binding fragment thereof, or competing antibody or antigen-binding fragment thereof, of any one of [1]-[5] in an amount effective to enhance said therapeutic effect of said soluble guanylyl cyclase activator.

[60] The method of [59], wherein said therapeutic effect comprises treatment of ischemia-reperfusion injury, or an autoimmune or inflammatory disease, in a human or companion/pet animal, working animal, sport animal, zoo animal, or other valuable animal kept in captivity.

[61] The method of [60], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, or trauma.

[62] The method of [60], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[63] Use of said monoclonal antibody or antigen-binding fragment thereof, or competing antibody or antigen-binding fragment thereof, of any one of [1]-[5] for the manufacture of a medicament to enhance the therapeutic effect of a soluble guanylyl cyclase activator.

[64] The use of [63], wherein said therapeutic effect comprises treatment of ischemia-reperfusion injury, or an autoimmune or inflammatory disease, in a human or companion/pet animal, working animal, sport animal, zoo animal, or other valuable animal kept in captivity.

[65] The use of [64], wherein said ischemia-reperfusion injury occurs in organ transplantation, acute kidney injury, cardiopulmonary bypass surgery, pulmonary hypertension, sickle cell disease, myocardial infarction, stroke, surgical resections and reconstructive surgery, reattachment of an appendage or other body part, skin grafting, and trauma.

[66] The use of [64], wherein said autoimmune or inflammatory disease is selected from the group consisting of arthritis, multiple sclerosis, psoriasis, Crohn's disease, inflammatory bowel disease, lupus, Grave's disease and Hashimoto's thyroiditis, and ankylosing spondylitis.

[67] A method of increasing the level of cGMP in vascular cells, comprising administering to said cells:
  i) an effective amount of a soluble guanylyl cyclase activator, and
  ii) a monoclonal antibody or antigen-binding fragment thereof, or competing antibody or antigen-binding fragment thereof, of any one of [1]-[5] in an amount effective to increase the level of cGMP in said vascular cells.

[68] The monoclonal antibody or antigen-binding fragment thereof, or competing antibody or antigen-binding fragment thereof, of any one of [1]-[5], which is an IgG isotype selected from among IgG1 isotype, IgG2 isotype, IgG3 isotype, and IgG4 isotype.

[69] A pharmaceutical composition, comprising said monoclonal antibody or antigen-binding fragment thereof, or competing antibody or antigen-binding fragment thereof, of [68], and a pharmaceutically or physiologically acceptable carrier, diluent, or excipient.

[70] The monoclonal antibody or antigen-binding fragment thereof, or competing antibody or antigen-binding fragment thereof, of [68] for use in human therapy or therapy of companion/pet animals, working animals, sport animals, zoo animals, or therapy of other valuable animals kept in captivity.

[71] The monoclonal antibody or antigen-binding fragment thereof, or competing antibody or antigen-binding fragment thereof, of [68] for use in treating ischemia-reperfusion injury, or an autoimmune or inflammatory disease, in a human or companion/pet animal, working animal, sport animal, zoo animal, or other valuable animal kept in captivity.

[72] The monoclonal antibody or antigen-binding fragment thereof, or competing antibody or antigen-binding fragment thereof, of [68] for use in treating a susceptible cancer.

[73] Use of said monoclonal antibody or antigen-binding fragment thereof, or competing antibody or antigen-binding fragment thereof, of [68] to treat ischemia-reperfusion injury, or an autoimmune or inflammatory disease, in a human or companion/pet animal, working animal, sport animal, zoo animal, or other valuable animal kept in captivity.

[74] Use of said monoclonal antibody or antigen-binding fragment thereof, or competing antibody or antigen-binding fragment thereof, of [68] to treat a susceptible cancer.

[75] Use of said monoclonal antibody or antigen-binding fragment thereof, or competing antibody or antigen-binding fragment thereof, of [68] for the manufacture of a medicament to treat ischemia-reperfusion injury, or an autoimmune or inflammatory disease, in a human or companion/pet animal, working animal, sport animal, zoo animal, or other valuable animal kept in captivity.

[76] Use of said monoclonal antibody or antigen-binding fragment thereof, or competing antibody or antigen-binding fragment thereof, of [68] for the manufacture of a medicament to treat a susceptible cancer.

Expressly encompassed herein is the use of the monoclonal antibodies or antigen-binding fragments thereof of [68]-[76] in any of the methods, uses, compositions, or any other embodiments disclosed herein.

[77] The monoclonal antibody or antigen-binding fragment thereof, or competing antibody or antigen-binding fragment thereof, of any one of [1]-[5], wherein:
i) when said monoclonal antibody or antigen-binding fragment thereof, or competing antibody or antigen-binding fragment thereof, is human IgG1 isotype, the human IgG1 constant region is modified at amino acid Asn297 to prevent to glycosylation; and/or at amino acid Leu 234 and/or Leu235 to alter Fc receptor interactions; and/or to enhance FcRn binding; and/or to alter antibody-dependent cellular cytotoxicity and/or complement-dependent cytotoxicity; and/or to induce heterodimerization, optionally further by introduction of a disulfide bond;
ii) when said monoclonal antibody or antigen-binding fragment thereof, or competing antibody or antigen-binding fragment thereof, is human IgG2 isotype, the human IgG2 constant region is modified at amino acid Asn297 to prevent to glycosylation; and/or to enhance FcRn binding; and/or to alter antibody-dependent cellular cytotoxicity and/or complement-dependent cytotoxicity; and/or to induce heterodimerization, optionally further by introduction of a disulfide bond;
iii) when said monoclonal antibody or antigen-binding fragment thereof, or competing antibody or antigen-binding fragment thereof, is human IgG3 isotype, the human IgG3 constant region is modified at amino acid Asn297 to prevent to glycosylation; and/or at amino acid 435 to extend half-life; and/or to enhance FcRn binding; and/or to alter antibody-dependent cellular cytotoxicity and/or complement-dependent cytotoxicity; and/or to induce heterodimerization, optionally further by introduction of a disulfide bond;
iv) when said monoclonal antibody or antigen-binding fragment thereof, or competing antibody or antigen-binding fragment thereof, is human IgG4 isotype, the human IgG4 constant region is modified within the hinge region to prevent or reduce strand exchange; and/or at amino acid 235 to alter Fc receptor interactions; and/or at amino acid Asn297 to prevent glycosylation; and/or to enhance FcRn binding; and/or to alter antibody-dependent cellular cytotoxicity; and/or complement-dependent cytotoxicity; and/or to induce heterodimerization, optionally further by introduction of a disulfide bond.

[78] The monoclonal antibody or antigen-binding fragment thereof, or competing antibody or antigen-binding fragment thereof, of [77], wherein:
i) when said monoclonal antibody or antigen-binding fragment thereof, or competing antibody or antigen-binding fragment thereof, is human IgG1 isotype, the human IgG1 constant region is modified at amino acid Asn297 to prevent to glycosylation by modification of Asn297→Ala (N297A) or Asn297→Gln (N297Q); and/or at amino acid Leu 234 by modification of Leu234→Ala (L234A) and/or Leu235 by modification of Leu235→Glu (L235E) or Leu235→Ala (L235A) or at both amino acid 234 and 235 by modification of Leu234→Ala and Leu235→Ala to alter Fc receptor interactions; and/or to enhance FcRn binding by modification of Met252→Tyr, Ser254→Thr, Thr256→Glu, Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains;
ii) when said monoclonal antibody or antigen-binding fragment thereof, or competing antibody or antigen-binding fragment thereof, is human IgG2 isotype, the human IgG2 constant region is modified at amino acid Asn297 to prevent to glycosylation by modification of Asn297→Ala or Asn297→Gln; and/or to enhance FcRn binding by modification of Met252→Tyr, Ser254→Thr, Thr256→Glu, Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains;
iii) when said monoclonal antibody or antigen-binding fragment thereof, or competing antibody or antigen-binding fragment thereof, is human IgG3 isotype, the human IgG3 constant region is modified at amino acid Asn297 to prevent to glycosylation by modification of Asn297→Ala or Asn297→Gln; and/or at amino acid 435 to extend half-life by modification of Arg435→His; and/or to enhance FcRn binding by modification of Met252→Tyr, Ser254→Thr, Thr256 Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains;
iv) when said monoclonal antibody or antigen-binding fragment thereof, or competing antibody or antigen-binding fragment thereof, is human IgG4 isotype, the human IgG4 constant region is modified within the hinge region to prevent or reduce strand exchange by modification of Ser228→Pro; and/or at amino acid 235 to alter Fc receptor interactions by modification of Leu235→Glu, or by modification within the hinge and at amino acid 235 by modifying Ser228→Pro and Leu235→Glu; and/or at amino acid Asn297 to prevent glycosylation by modification of Asn297→Ala; and/or to enhance FcRn binding by modification of Met252→Tyr, Ser254→Thr, Thr256→Glu, Met428→Leu, or Asn434→Ser; and/or to alter antibody-dependent cellular cytotoxicity and/or complement-dependent cytotoxicity; and/or to induce heterodimerization by modification of Thr366→Trp, and optionally further by introduction of a disulfide bond by modification of Ser354→Cys and Tyr349→Cys on opposite CH3 domains.

Expressly encompassed herein is the use of the monoclonal antibodies or antigen binding fragments thereof of [77]-[78] in any of the methods, uses, compositions, or any other embodiments disclosed herein.

Further scope of the applicability of the present antibody compounds and methods will become apparent from the detailed description provided below. However, it should be understood that the detailed description and specific examples, while indicating particular embodiments of the disclosure, are given by way of illustration only since various changes and modifications within the spirit and scope of the disclosure will become apparent to those skilled in the art from this detailed description.

BRIEF DESCRIPTION OF THE DRAWINGS

The above and other aspects, features, and advantages of the present disclosure will be better understood from the following detailed descriptions taken in conjunction with the accompanying drawing(s), all of which are given by way of illustration only, and are not limitative of the present disclosure, in which.

RBCs are incubated for 60 minutes on ice with various concentrations of purified antibodies from clones C1 1, C1 1.1, C1 13, and C1 13.1. Cells are then washed with cold PBS containing EDTA, incubated for an additional hour on ice with FITC labeled donkey anti-human antibody, washed, and antibody binding is analyzed using a BD FACS Aria Cell Sorter (Becton Dickinson) or a C6 Accuri Flow Cytometer (Becton Dickinson).

Figure 1A:
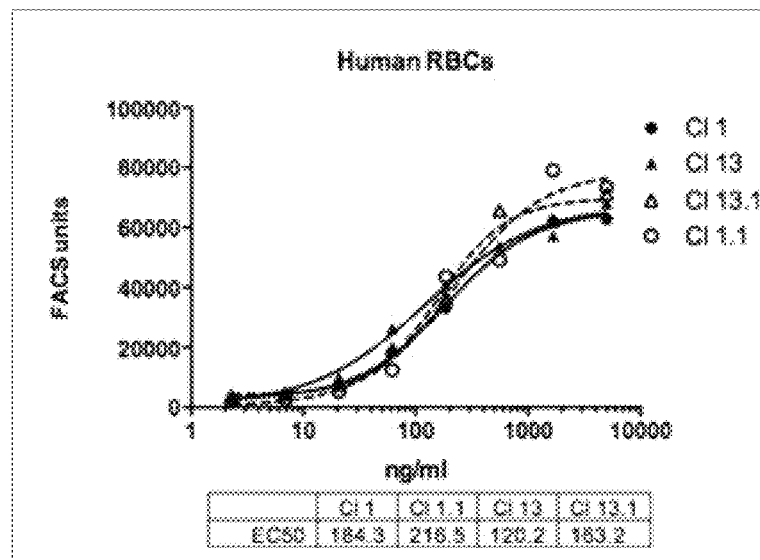
FIGS. 1A, 1B, 1C, and 1D show cross species binding curves to human, mouse, rat, and porcine RBCs, respectively, generated using various concentrations of purified antibodies from clones C1 1, C1 1.1, C1 13, and C1 13.1 as described in Example 3. Clones C1 1 and C1 13 are as described in Table 3. Clones C1 1.1 and C1 13.1 are Fc mutants of clones C1 1 and C1 13, respectively, modified to reduce effector function. Each has an Asn297→Gln(N297Q) mutation in the Fc domain (Sazinsky et al. (2008) *PNAS* 105(51):20167-20172). All of these clones exhibit concentration-dependent binding to all of the species of RBCs tested.
Figure 1B:
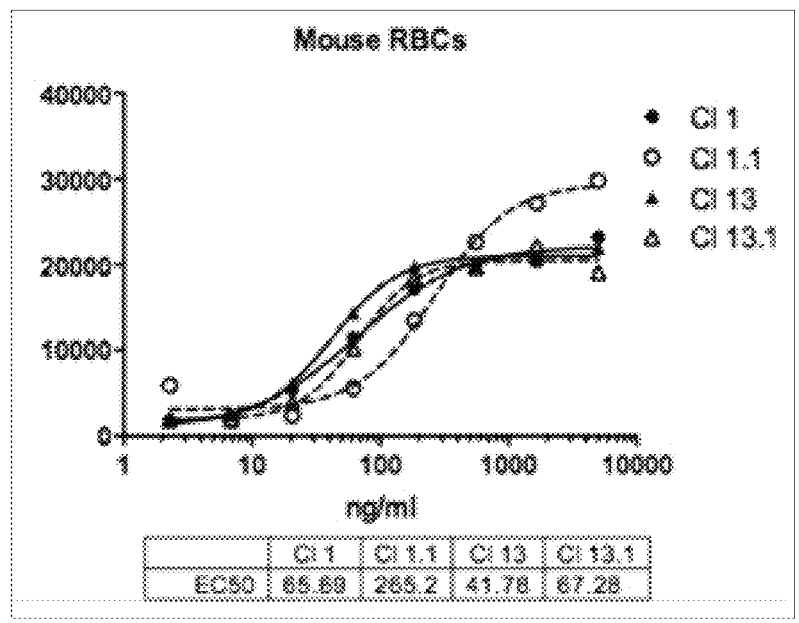
Figure 1C:
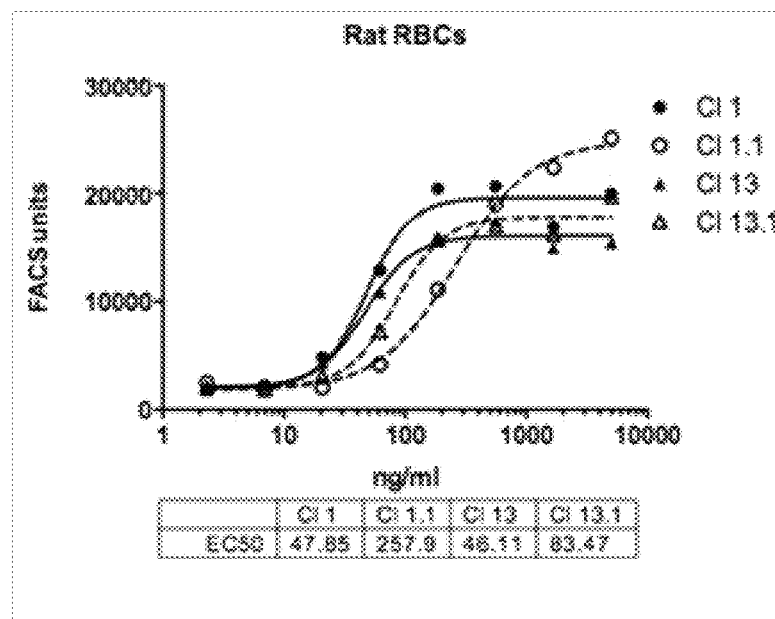
Figure 1D:
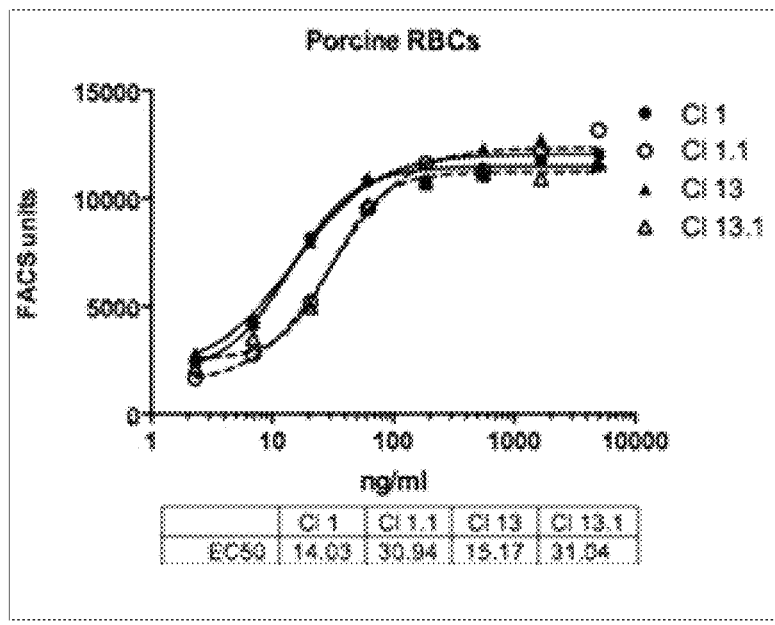
Figure 2:
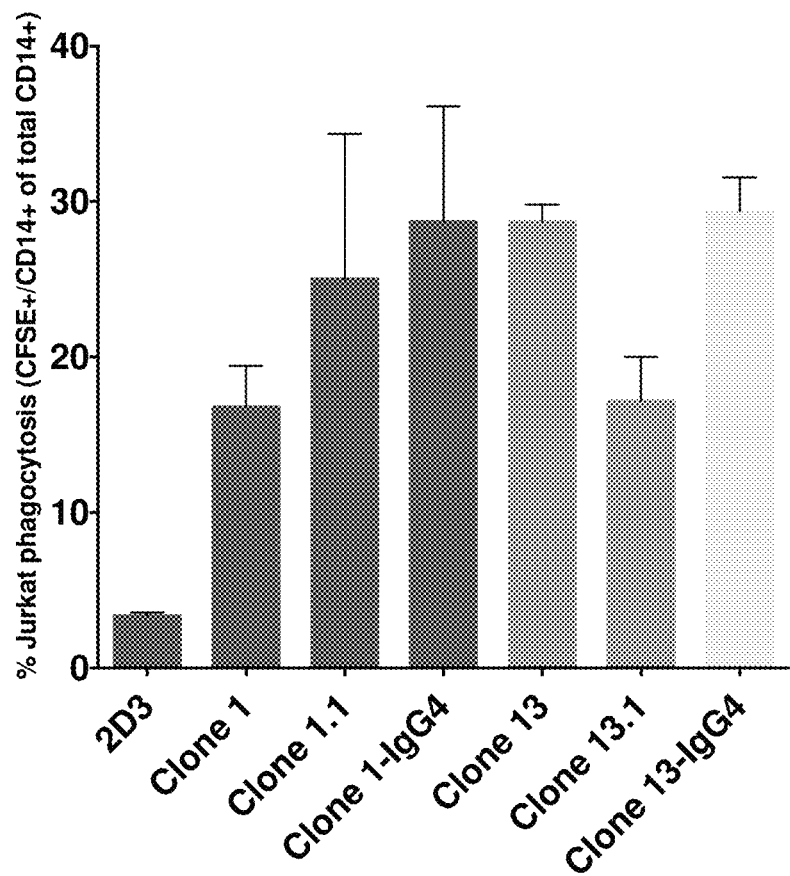

FIG. 2 shows CD47 mAb-mediated phagocytosis of Jurkat cells. Target (Jurkat) and effector (human macrophages) are combined at a target effector ratio of 4:1, 10 µg/ml of the CD47 mAbs added and incubated for 2 hours at 37 C. Percent phagocytosis is determined by flow cytometry as the percentage of $CFSE^+/CD14^+$ cells from the total $CD14^+$ population. All of the clones, except the negative control mAb 2D3, increase phagocytosis of the Jurkat cells by the macrophages irrespective of their affinity to activate Fc receptors.

Figure 3:
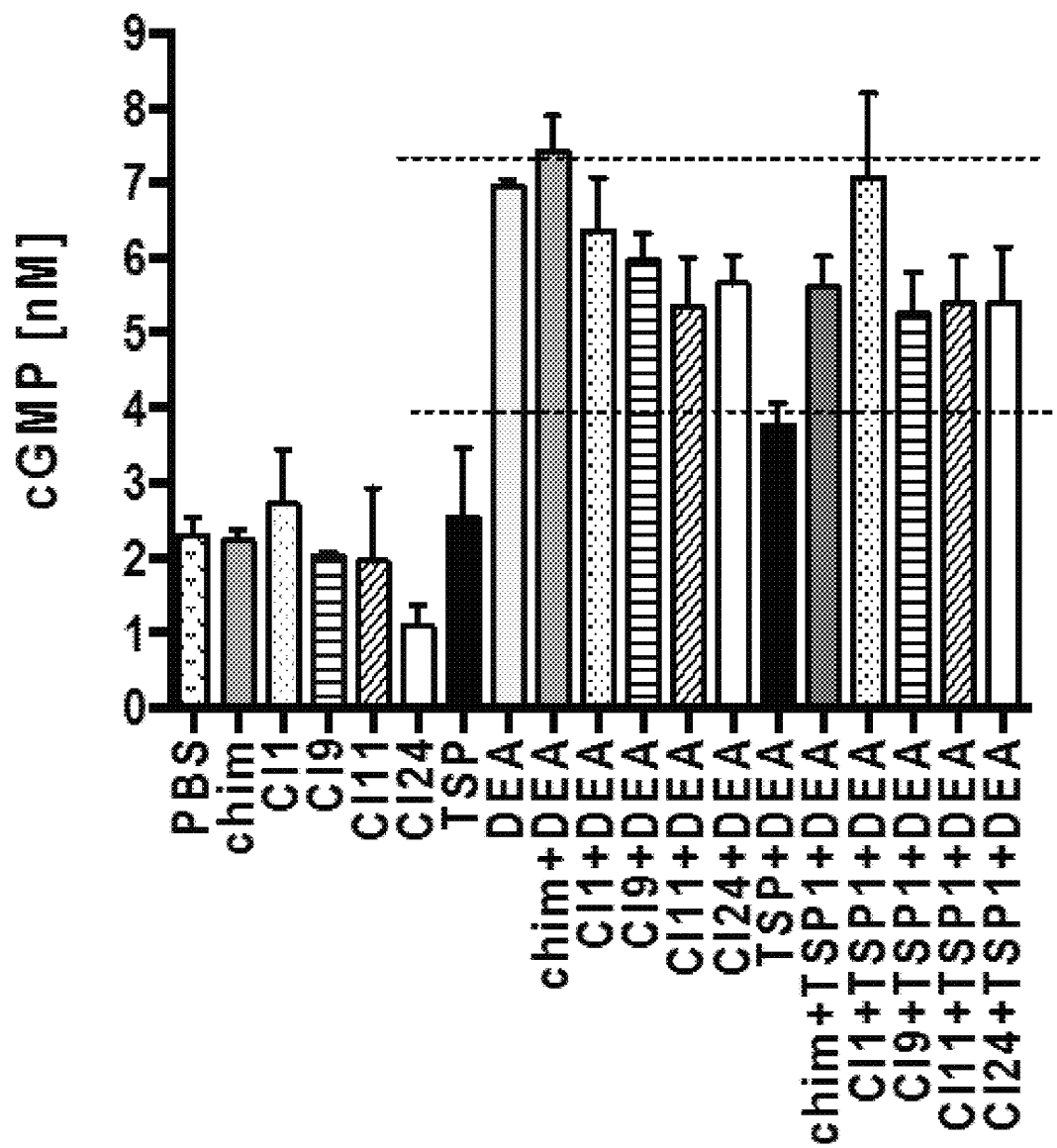

FIG. 3 shows reversal of TSP1 inhibition of NO-stimulated cGMP production by humanized antibodies of the present disclosure. As described in Example 5, Jurkat JE6.1 cells are incubated overnight in serum-free medium and then incubated with humanized antibodies of the present disclosure or the control chimeric mAb, and with or without TSP1, followed by treatment with or without a NO donor. Cells are lysed 5 minutes later and cGMP is measured. None of the present humanized antibody clones tested, or the control chimeric mAb, has an effect on basal cGMP levels. The control chimeric antibody reverses the TSP1 inhibition, as do humanized clones 1, 9, 11, and 24 disclosed herein (C1 1; C1 9; C1 11; C1 24, respectively). PBS: phosphate buffered saline; TSP or TSP1: thrombospondin-1; DEA: diethylamine NONOate; chim: chimeric antibody >VxP037-01LC (SEQ ID NO:7))/>VxP037-01HC (SEQ ID NO:57).

Figure 4:
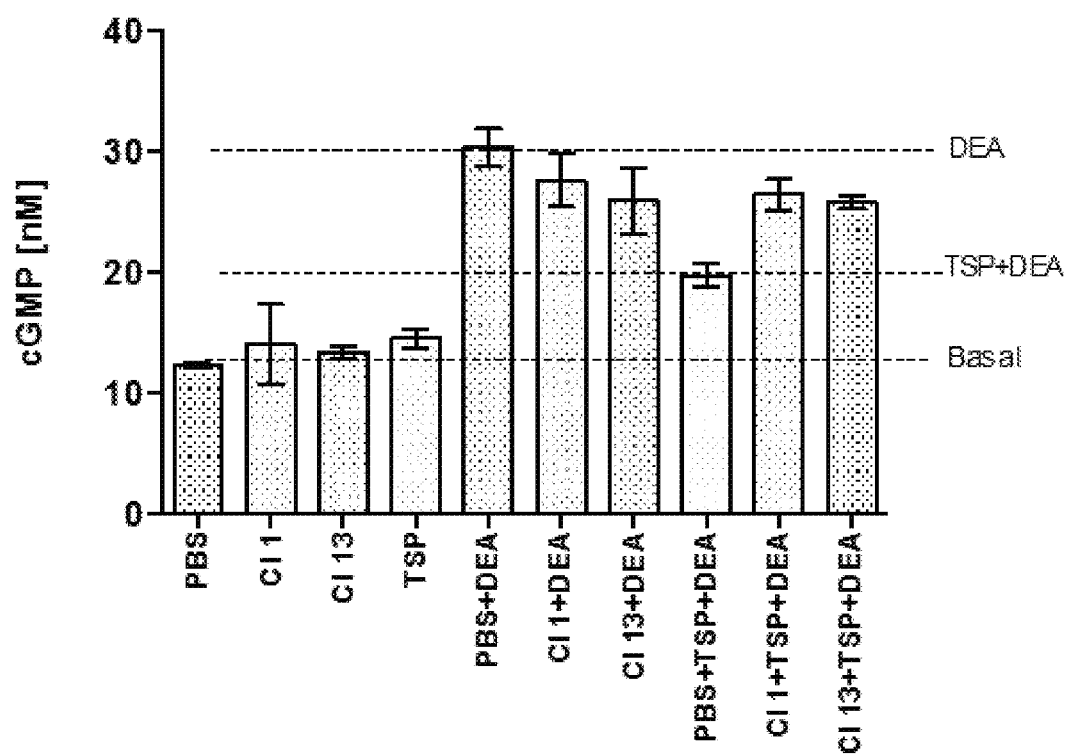

FIG. 4 shows reversal of TSP1 inhibition of NO-stimulated cGMP production by humanized antibodies of the present disclosure. As described in Example 5, Jurkat JE6.1 cells are incubated overnight in serum-free medium and then incubated with purified humanized Clone 1 and 13 antibodies, or PBS as the control, and with or without TSP1, followed by treatment with or without a NO donor. Cells are lysed 5 minutes later and cGMP is measured. The humanized antibody clones or PBS have no effect on basal cGMP levels. The humanized clones 1 and 13 reverse the TSP1 inhibition, while PBS has no effect. PBS: phosphate buffered saline; TSP or TSP1: thrombospondin-1; DEA: diethylamine NONOate.

Figure 5:
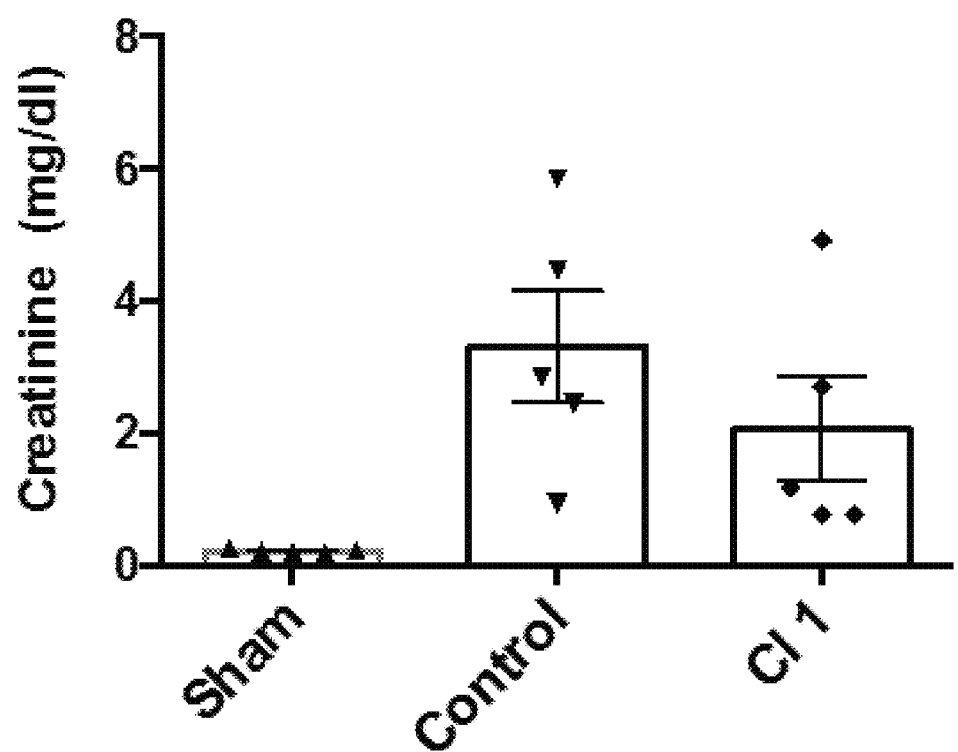

FIG. 5 shows that treatment of a donor kidney with Clone 1 (C1 1) at the time of organ harvest is effective in reducing IRI and kidney damage in vivo in a rat kidney transplantation model as assessed by measuring serum creatinine. A syngeneic rat renal transplantation model of IRI with bilaterally nephrectomized recipients is used to evaluate the effect of the anti-CD47 monoclonal antibody Clone 1 on graft function following transplantation. Male Lewis rats weighing 275-300 g are used as both donor and recipient animals. Donor kidneys are flushed with 50 µg of purified Clone 1 or vehicle (phosphate buffered saline, pH 7.2), stored at 4° C. in University of Wisconsin preservation (WU) solution for 6 hours, and then transplanted. Two days following transplantation, kidney function is assessed by measuring circulating serum creatinine. Treatment of donor kidneys with Clone 1 results in improved kidney function compared to controls as measured by a reduction in serum creatinine.

Figure 6:
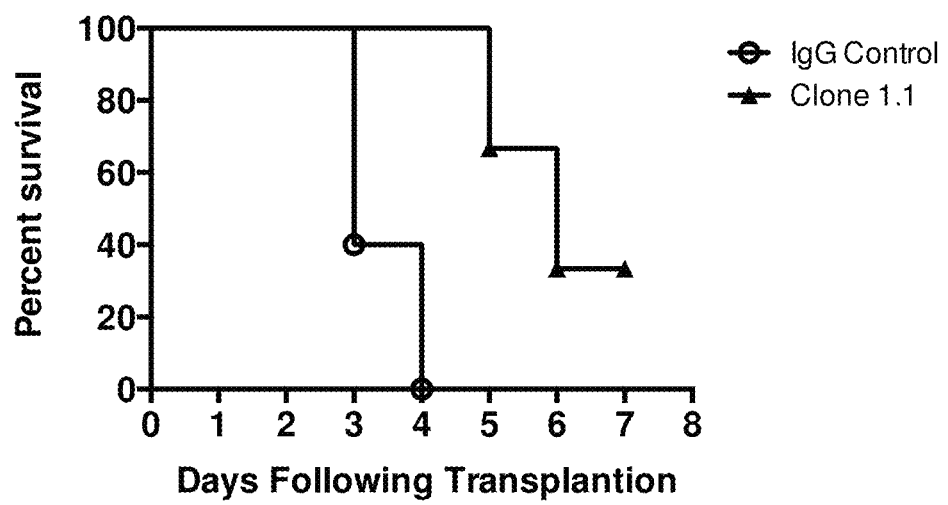

FIG. 6 shows the survival in a DCD (donation after cardiac death) rat transplant model. Male Lewis rats weighing 275-300 g underwent 60 minutes of warm ischemia, prior to flushing the donor kidneys with 50 µg of purified Clone 1.1 or an IgG control mAb. Kidneys are then stored at 4° C. in University of Wisconsin preservation solution (UW) for 6 hours prior to transplantation. In this experiment, survival is monitored over a 7 day time period. All animals that received the IgG control mAb-treated kidney died within 4 days. In contrast, survival is significantly prolonged in the animals that received the Clone1.1 treated kidney, with 30% of the animals surviving for the 7 day duration of the experiment. This shows that with extended periods of warm ischemia, treatment of donor kidneys with Clone 1.1 reduces IRI and increases survival of the recipient.

Figure 7:
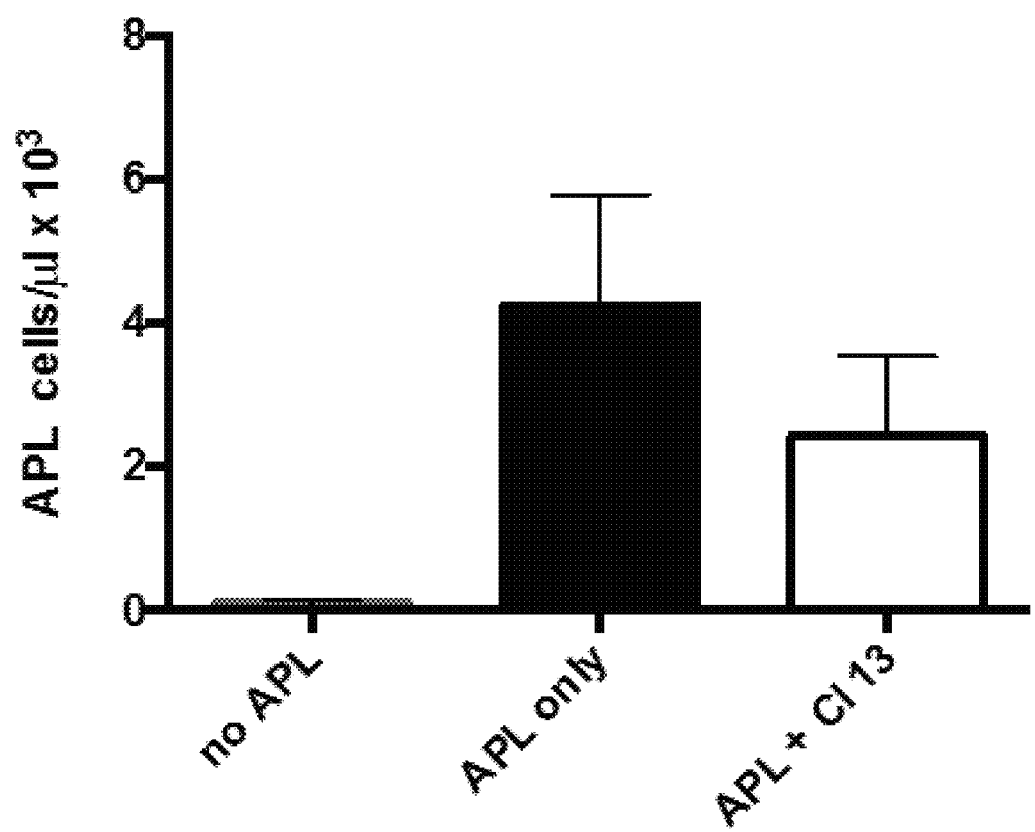

FIG. 7 shows that purified, humanized antibody Clone 13 (C1 13) reduces tumor burden in vivo in a syngeneic mouse Acute Promyelocytic Leukemia (APL) model. Murine APL cells (B6APL1) are injected intravenously into C57BL/6 mice randomized into three groups (5-10 mice per group):

Group 1: no APL; Group 2: APL with no treatment; Group 3: APL treated with anti-CD47mAb C1 13. Antibody treatment is initiated on the day of tumor inoculation (day 0), and given in single doses of 10 µg/dose (0.4 mg/kg) by intraperitoneal injection on days 0, 3, and 6. Circulating APL cells (representing the tumor burden) are evaluated at day 25 following tumor inoculation by flow cytometry ($CD34^+$/$CD117^+$ cells). Mice treated with C1 13 have reduced tumor burden compared to untreated mice at 25 days after tumor inoculation, demonstrating anti-tumor activity of this humanized clone.

Figure 8:
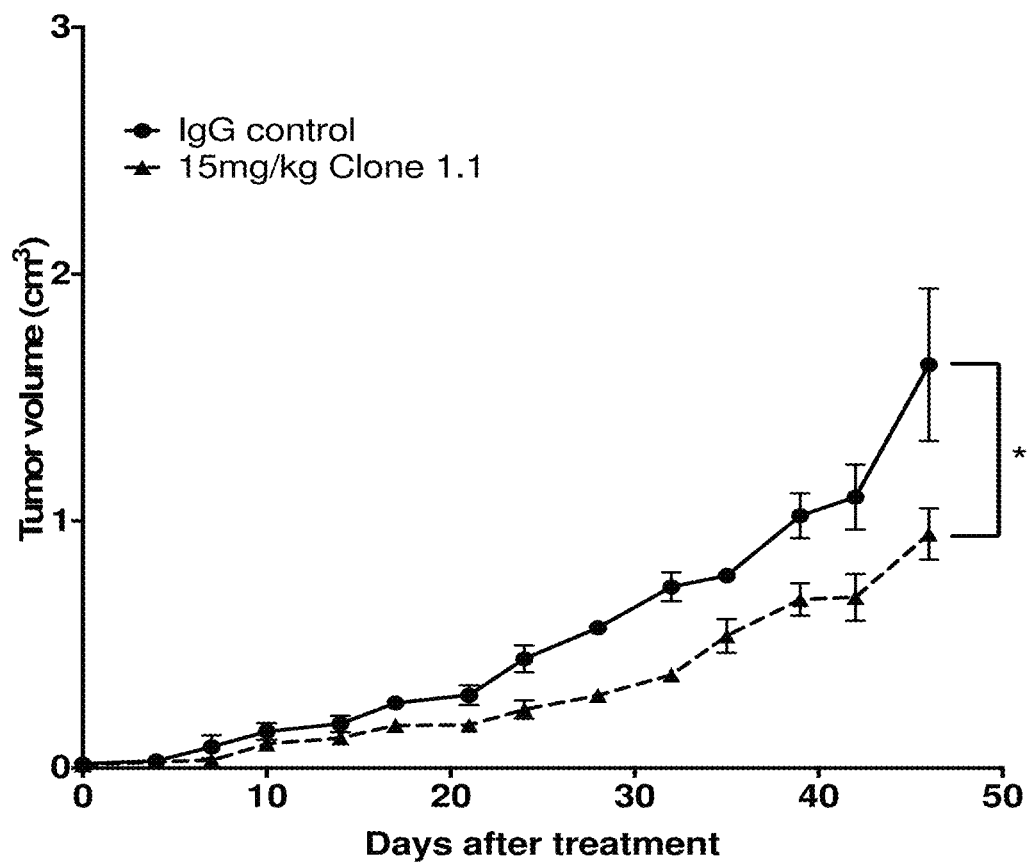

FIG. 8 shows that treatment with the CD47 mAb Clone 1.1 significantly reduced tumor growth of the HepG2 tumors. Male NSG mice are obtained from The Jackson Laboratory (Bar Harbor, Me.) and housed in cages in temperature and light-controlled environments with access to water and food ad libitum. For the heterotopic xenograft model, HepG2-luc2 cells (Perkin Elmer, Waltham, Mass. #134280) are suspended in DMEM containing 25% (v/v), and 1,000,000 cells implanted subcutaneously into the dorsal subcutaneous space of 4- to 8-wk-old NSG mice. After 2 weeks of growth, antibody treatment is begun with twice-weekly intraperitoneal injections of 15 mg/kg of either anti-CD47 antibody Clone 1.1 or an IgG control for 6 weeks. Tumor volumes are calculated twice weekly using (length× width)/0.6. After 6 weeks of treatment, animals are euthanized and tumors were resected, weighed, and fixed in 10% formalin.

DETAILED DESCRIPTION

The following detailed description is provided to aid those skilled in the art in practicing the various embodiments of the present disclosure described herein, including all the methods, uses, compositions, etc., described herein. Even so, the following detailed description should not be construed to unduly limit the present disclosure, as modifications and variations in the embodiments herein discussed may be made by those of ordinary skill in the art without departing from the spirit or scope of the present discoveries.

Any feature, or combination of features, described herein is(are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

The contents of all publications, patent applications, patents, and other references mentioned herein are incorporated by reference herein in their entirety. In case of conflict, the present specification, including explanations of terms, will control.

Antibody compounds of the present disclosure can bind to epitopes in the extracellular IgV domain of CD47, inhibiting TSP1 and SIRPalpha binding to CD47 and receptor activation, while inducing little or no agonist activity, and promoting tumor cell phagocytic clearance. In view of these properties, antibody compounds of the present disclosure should be therapeutically useful in treating many forms of IRI and cancers.

The present antibody compounds can also possess a number of other desirable properties, including broad reactivity with CD47 of a wide variety of mammalian species, including that of human, mouse, rat, pig, cynomolgus monkey, and/or dog, i.e., any individual one of these mammalian species, or various combinations thereof, making these antibodies useful in both human and veterinary medicine. This broad reactivity is further advantageous in that it facilitates preclinical studies including, but not limited to, safety and efficacy studies, in a variety of mammalian species, and therefore the development of such antibodies as human and veterinary therapeutics.

Thus, antibody compounds of the present disclosure exhibit the following desirable therapeutic activities:
Binding to CD47 of multiple mammalian species;
Blocking SIRPalpha and TSP1 binding to CD47;
Promoting phagocytosis of cancer cells; and
Reversing TSP1 inhibition of nitric oxide signaling
and are therefore useful in treating ischemia reperfusion injury and cancers.

Definitions

The following definitions are provided to aid the reader in understanding the various aspects of the present disclosure. Unless defined otherwise, all technical and scientific terms used herein have the same meaning as commonly understood by those of ordinary skill in the art to which this disclosure pertains.

A full-length antibody as it exists naturally is an immunoglobulin molecule comprising two heavy (H) chains and two light (L) chains interconnected by disulfide bonds. The amino terminal portion of each chain includes a variable region of about 100-110 or more amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: 1-R1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions are in accordance with the well-known Kabat numbering convention. While the light chain CDRs and heavy chain CDRs disclosed herein are numbered 1, 2, and 3, respectively, it is not necessary that they be employed in the corresponding antibody compound light and heavy chain variable regions in that numerical order, i.e., they can be present in any numerical order in a light or heavy chain variable region, respectively.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

The monoclonal antibodies and other antibody compounds useful in the methods and compositions described herein can be any of these isotypes. Furthermore, any of these isotypes can comprise amino acid modifications as follows.

In some embodiments, the antibody constant region is of human IgG1 isotype.

In some embodiments, the human IgG1 constant region is modified at amino acid Asn297 (Kabat Numbering) to prevent to glycosylation of the antibody. For example, this modification can be Asn297→Ala (N297A) or Asn297→Gln(N297Q) (Sazinsky et al. (2008) *PNAS* 105 (51):20167-20172).

In some embodiments, the constant region of the antibody is modified at amino acid Leu234 (Kabat Numbering) to alter Fc receptor interactions. For example, this modification can be Leu234→Ala (L234A).

In some embodiments, the constant region of the antibody is modified at amino acid Leu235 (Kabat Numbering) to alter Fc receptor interactions. For example, this modification can be Leu235→Glu (L235E) or Leu235→Ala (L235A).

In some embodiments, the constant region of the antibody is altered at both amino acid 234 and 235. For example, these modifications can be Leu234→Ala and Leu235→Ala (L234A/L235A) (EU index of Kabat et al. (1991) *Sequences of Proteins of Immunological Interest*).

In some embodiments, the constant region of the antibody is of human IgG2 isotype.

In some embodiments, the human IgG2 constant region is modified at amino acid Asn297 (Kabat Numbering) to prevent to glycosylation of the antibody. For example, this modification can be Asn297→Ala (N297A) or Asn297→Gln(N297Q).

In some embodiments, the constant region of the antibody is of human IgG3 isotype.

In some embodiments, the human IgG3 constant region is modified at amino acid Asn297 (Kabat Numbering) to prevent to glycosylation of the antibody. For example, this modification can be Asn297→Ala (N297A) or Asn297→Gln(N297Q).

In some embodiments, the human IgG3 constant region is modified at amino acid 435 to extend the half-life. For example, this modification can be Arg435→His (R435H) (EU index of Kabat et al. (1991) *Sequences of Proteins of Immunological Interest*).

In some embodiments, the constant region of the antibody is of human IgG4 isotype.

In some embodiments, the human IgG4 constant region is modified within the hinge region to prevent or reduce strand exchange. For example, this modification can be Ser228→Pro (S228P) (Angal et al. (1993) *Molecular Immunology* 30(1):105-108).

In other embodiments, the human IgG4 constant region is modified at amino acid 235 to alter Fc receptor interactions. For example, this can be Leu235→Glu (L235E).

In some embodiments, the human IgG4 constant region is modified within the hinge and at amino acid 235. For example, this can be Ser228→Pro and Leu235→Glu (S228P/L235E).

In some embodiments, the human IgG4 constant region is modified at amino acid Asn297 (Kabat Numbering) to prevent to glycosylation of the antibody. For example, this can be Asn297→Ala (N297A). (EU index of Kabat et al. (1991) *Sequences of Proteins of Immunological Interest*).

In some embodiments, the human IgG constant region is modified to enhance FcRn binding. Examples of Fc mutations that enhance binding to FcRn are Met252→Tyr, Ser254→Thr, Thr256→Glu (M252Y, S254T, and T256E, respectively) (Kabat numbering, Dall'Acqua et al. (2006) *J. Biol. Chem.* 281(33) 23514-23524), or Met428→Leu and Asn434→Ser (M428L, N434S) (Zalevsky et al. (2010) *Nature Biotech.* 28(2):157-159). (EU index of Kabat et al. (1991) *Sequences of Proteins of Immunological Interest*). In some embodiments, the human IgG constant region is modified to alter antibody-dependent cellular cytotoxicity (ADCC) and/or complement-dependent cytotoxicity (CDC), e.g., the amino acid modifications described in Natsume et al. (2008) *Cancer Res.* 68(10):3863-72; Idusogie et al. (2001) *J. Immunol.* 166(4):2571-5; Moore et al. (2010) *mAbs* 2(2):181-189; Lazar et al. (2006) *PNAS* 103(11):4005-4010; Shields et al. (2001) *J. Biol. Chem.* 276(9):6591-6604; Stavenhagen et al. (2007) *Cancer Res.* 67(18):8882-8890; Stavenhagen et al. (2008) *Advan. Enzyme Regul.* 48:152-164; Alegre et al. (1992) *J. Immunol.* 148:3461-3468; reviewed in Kaneko and Niwa (2011) *Biodrugs* 25(1):1-11.

In some embodiments, the human IgG constant region is modified to induce heterodimerization. For example, having an amino acid modification within the CH3 domain at Thr366, which when replaced with a more bulky amino acid, such as Trp (T366W), is able to preferentially pair with a second CH3 domain having amino acid modifications to less bulky amino acids at positions Thr366, Leu368, and Tyr407, e.g., Ser, Ala, and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (reviewed in Carter (2001) *Journal of Immunological Methods* 248:7-15).

As used herein, the term "monoclonal antibody" (mAb) as applied to the present antibody compounds refers to an antibody that is derived from a single copy or clone including, for example, any eukaryotic, prokaryotic, or phage clone, and not the method by which it is produced. mAbs of the present disclosure preferably exist in a homogeneous or substantially homogeneous population, and can be chimeric or humanized. Complete mAbs contain two heavy chains and two light chains.

"Antigen binding fragments" of such monoclonal antibodies may be desirable for certain applications due to their small size and consequent superior tissue distribution, and include, for example, Fab fragments, Fab' fragments, F(ab')$_2$ fragments, Fd fragments, single chain Fv fragments (ScFv), and one-armed antibodies comprising a light chain and a heavy chain. Preferred antigen binding fragments are those that bind to the antigen recognized by the intact antibody. Fc fragments can also be obtained. Monoclonal antibodies and antigen-binding fragments thereof of the present disclosure can be produced, for example, by recombinant technologies, phage display technologies, synthetic technologies, e.g., CDR-grafting, or combinations of such technologies, or other technologies known in the art, including proteolytic digestion of intact antibodies.

"Antibody compounds" refers to mAbs, antigen-binding fragments thereof such as Fabs, etc., and competing antibodies, disclosed herein that specifically bind CD47 of various species, including human, rat, mouse, pig, cynomolgus monkey, and dog CD47, and that exhibit the properties disclosed herein. Thus, the term "mAb" as used herein with respect to antibodies encompassed by the present disclosure includes Fabs and competing antibodies. Additional antibody compounds exhibiting similar functional properties according to the present disclosure can be generated by conventional methods. For example, mice can be immunized with human CD47 or fragments thereof, the resulting antibodies can be recovered and purified, and determination of whether they possess binding and functional properties similar to or the same as the antibody compounds disclosed herein can be assessed by the methods disclosed in Examples 3, 4, and 5, below. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

The phrase "humanized antibodies" refers to monoclonal antibodies and antigen binding fragments thereof, including the antibody compounds disclosed herein, that have binding and functional properties according to the disclosure similar to those disclosed herein, and that have framework and constant regions that are substantially human or fully human surrounding CDRs derived from a non-human antibody. "Framework region" or "framework sequence" refers to any one of framework regions 1 to 4. Humanized antibodies and antigen binding fragments encompassed by the present disclosure include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least 80% sequence identity to a known human germline framework sequence. Preferably, the substantially human frameworks have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, to a framework sequence disclosed herein, or to a known human germline framework sequence.

CDRs encompassed by the present disclosure include not only those specifically disclosed herein, but also CDR sequences having sequence identities of at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a CDR sequence disclosed herein. Alternatively, CDRs encompassed by the present disclosure include not only those specifically disclosed herein, but also CDR sequences having 1, 2, 3, 4, 5, or 6 amino acid changes at corresponding positions compared to CDR sequences disclosed herein. Such sequence identical, or amino acid modified, CDRs preferably bind to the antigen recognized by the intact antibody.

As used herein, the phrase "sequence identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., *J. Mol. Biol.* 215: 403-410 (1990) and Altschul et al. *Nucl. Acids Res.* 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

Fully human frameworks are those that are identical to a known human germline framework sequence. Human framework germline sequences can be obtained from ImMunoGeneTics (IMGT) via their website or from *The Immunoglobulin FactsBook* by Marie-Paule Lefranc and Gerard Lefranc, Academic Press, 2001, ISBN 012441351. For example, germline light chain frameworks can be selected from the group consisting of: A11, A17, A18, A19, A20, A27, A30, L1, L11, L12, L2, L5, L15, L6, L8, O12, O2, and O8, and germline heavy chain framework regions can be selected from the group consisting of: VH2-5, VH2-26, VH2-70, VH3-20, VH3-72, VH1-46, VH3-9, VH3-66, VH3-74, VH4-31, VH1-18, VH1-69, VI-13-7, VH3-11, VH3-15, VH3-21, VH3-23, VH3-30, VH3-48, VH4-39, VH4-59, and VH5-5I.

Humanized antibodies in addition to those disclosed herein exhibiting similar functional properties according to the present disclosure can be generated using several different methods. In one approach, the parent antibody compound CDRs are grafted into a human framework that has a high sequence identity with the parent antibody compound framework. The sequence identity of the new framework will generally be at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identical to the sequence of the corresponding framework in the parent antibody compound. In the case of frameworks having fewer than 100 amino acid residues, one, two, three, four, five, six, seven, eight, nine, or ten amino acid residues can be changed. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816,397; 5,225,539; and 5,693,761; computer programs ABMOD and ENCAD as described in Levitt (1983) *J. Mol. Biol.* 168:595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as follows.

When an amino acid falls under the following category, the framework amino acid of the human germ-line sequence that is being used (the "acceptor framework") is replaced by a framework amino acid from a framework of the parent antibody compound (the "donor framework"): (a) the amino acid in the human framework region of the acceptor framework is unusual for human frameworks at that position, whereas the corresponding amino acid in the donor immunoglobulin is typical for human frameworks at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) *J. Mol. Biol.* 294:151-162.

The method described in Example 1 below can also be employed.

Applying the teachings of the present disclosure, a person skilled in the art can use common techniques, e.g., site-directed mutagenesis, to substitute amino acids within the presently disclosed CDR and framework sequences and thereby generate further variable region amino acid sequences derived from the present sequences. Up to all naturally occurring amino acids can be introduced at a specific substitution site, including conservative amino acid substitutions as are well known to those of ordinary skill in the art. The methods disclosed herein can then be used to screen these additional variable region amino acid sequences to identify sequences having the indicated in vitro and/or in vivo functions. In this way, further sequences suitable for preparing human engineered antibodies and antigen-binding portions thereof in accordance with the present disclosure can be identified. In some embodiments, amino acid substitution within the frameworks can include one, two, three, four, five, six, seven, eight, nine, or ten positions within any one or more of the 4 light chain and/or heavy chain framework regions disclosed herein. In some embodiments, amino acid substitution within the CDRs is restricted to one, two, three, four, or five positions within any one or more of the 3 light chain and/or heavy chain CDRs. Combinations of the various changes within these framework regions and CDRs described above are also possible.

That the functional properties of the antibody compounds generated by introducing the amino acid modifications discussed above conform to, and are comparable to, those exhibited by the specific molecules disclosed herein can be confirmed by the methods disclosed in the Examples below.

The terms "specifically binds", "bind specifically", "specific binding", and the like as applied to the present antibody compounds refer to the ability of a specific binding agent (such as an antibody) to bind to a target molecular species in preference to binding to other molecular species with which the specific binding agent and target molecular species are admixed. A specific binding agent is said specifically to recognize a target molecular species when it can bind specifically to that target.

"Binding affinity" is a term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

The term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous in the linear sequence.

Monoclonal antibodies or antigen-binding fragments thereof encompassed by the present disclosure that "compete" with the molecules disclosed herein are those that bind human CD47 at site(s) that are identical to, or overlapping with, the site(s) at which the present molecules bind. Competing monoclonal antibodies or antigen-binding fragments thereof can be identified, for example, via an antibody competition assay. For example, a sample of purified or partially purified human CD47 extracellular domain can be bound to a solid support. Then, an antibody compound, or antigen binding fragment thereof, of the present disclosure and a monoclonal antibody or antigen-binding fragment thereof suspected of being able to compete with such disclosure antibody compound are added. One of the two molecules is labeled. If the labeled compound and the unlabeled compound bind to separate and discrete sites on CD47, the labeled compound will bind to the same level whether or not the suspected competing compound is present. However, if the sites of interaction are identical or overlapping, the unlabeled compound will compete, and the amount of labeled compound bound to the antigen will be lowered. If the unlabeled compound is present in excess, very little, if any, labeled compound will bind. For purposes of the present disclosure, competing monoclonal antibodies or antigen-binding fragments thereof are those that decrease the binding of the present antibody compounds to CD47 by about 50%, about 60%, about 70%, about 80%, about 85%, about 86%, about 87%, about 88%, about 89%, about 90%, about 91%, about 92%, about 93%, about 94%, about 95%, about 96%, about 97%, about 98%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared.

Whether monoclonal antibodies or antigen-binding fragments thereof that compete with antibody compounds of the present disclosure in such competition assays possess the same or similar functional properties of the present antibody compounds can be determined via these methods in conjunction with the methods described in Examples 3-5, below. In various embodiments, competing antibodies for use in the therapeutic methods encompassed herein possess biological activities as described herein in the range of from about 50% to about 100% or about 125%, or more, compared to that of the antibody compounds disclosed herein. In some embodiments, competing antibodies possess about 50%, about 60%, about 70%, about 80%, about 85%, about 90%, about 91%, about 92%, about 93%, about 94%, about 95%, about 96%, about 97%, about 98%, about 99%, or identical biological activity compared to that of the antibody compounds disclosed herein as determined by the methods disclosed in the Examples presented below.

The term "treating" (or "treat" or "treatment") means slowing, interrupting, arresting, controlling, stopping, reducing, or reversing the progression or severity of a sign, symptom, disorder, condition, or disease, but does not necessarily involve a total elimination of all disease-related signs, symptoms, conditions, or disorders. The term "treating" and the like refer to a therapeutic intervention that ameliorates a sign, symptom, etc., of a disease or pathological condition after it has begun to develop.

Acute events and chronic conditions can be treated. In an acute event, an antibody or antigen binding fragment thereof is administered at the onset of a symptom, disorder, condition, disease, or procedure, and is discontinued when the acute event ends, or in the case of organ transplantation to the organ, at the time of organ harvest and/or to the transplant recipient at the time of organ transplantation. In contrast, a chronic symptom, disorder, condition, or disease is treated over a more protracted time frame.

The term "effective amount" refers to the amount or dose of an antibody compound of the present disclosure which, upon single or multiple dose administration to a patient or organ, provides the desired treatment or prevention.

The precise effective amount for any particular subject will depend upon their size and health, the nature and extent of their condition, and the therapeutics or combination of therapeutics selected for administration. The effective amount for a given patient is determined by routine experimentation and is within the judgment of a clinician. In some embodiments, an effective dose will generally be from about 0.01 mg/kg to about 50 mg/kg, or about 0.05 mg/kg to about 10 mg/kg of the compositions of the present disclosure in the individual to which it is administered. Therapeutically effective amounts of the present antibody compounds can also comprise an amount in the range of from about 0.1 mg/kg to about 150 mg/kg, from about 0.1 mg/kg to about 100 mg/kg, or from about 0.1 mg/kg to about 50 mg/kg per single dose administered to a harvested organ or to a patient. Known antibody-based pharmaceuticals provide guidance in this respect. For example, Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

A therapeutically effective amount for any individual patient can be determined by the health care provider by monitoring the effect of the antibody compounds on a biomarker, such as serum biomarkers of injury of the treated organ, including but not limited to liver, kidney, lung, intestine, pancreas and heart, changes in pulmonary artery pressures, cell surface CD47 expression in tumor or non-tumor tissues, tumor regression, circulating tumor cells or tumor stem cells, etc. Analysis of the data obtained by these methods permits modification of the treatment regimen during therapy so that optimal amounts of antibody compounds of the present disclosure, whether employed alone or in combination with one another, or in combination with another therapeutic agent, or both, are administered, and so that the duration of treatment can be determined as well. In this way, the dosing/treatment regimen can be modified over the course of therapy so that the lowest amounts of antibody compounds used alone or in combination that exhibit satisfactory efficacy are administered, and so that administration of such compounds is continued only so long as is necessary to successfully treat the patient. Known antibody-based pharmaceuticals provide guidance relating to frequency of administration e.g., whether a pharmaceutical should be delivered daily, weekly, monthly, etc. Frequency and dosage may also depend on the severity of symptoms.

The antibody compounds of the present disclosure can be used as medicaments in human and veterinary medicine, administered by a variety of routes. Veterinary applications include the treatment of companion/pet animals, such as cats and dogs; working animals, such as guide or service dogs, and horses; sport animals, such as horses and dogs; zoo animals, such as primates, cats such as lions and tigers, bears, etc.; and other valuable animals kept in captivity.

Antibody compounds can be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions. Typically, the therapeutic compositions can be prepared as injectables, either as liquid solutions or suspensions. Solid forms suitable for solution in, or suspension in, liquid vehicles prior to injection can also be prepared.

Direct delivery of the compositions can generally be accomplished by injection, subcutaneously, intraperitoneally, intravenously, or intramuscularly, or delivered to the interstitial space of a tissue. The compositions can also be administered into a lesion such as a tumor. Dosage treatment may be a single dose schedule or a multiple dose schedule.

In some embodiments, such compositions are formulated for parenteral administration by, for example, intravenous, intramuscular, subcutaneous, etc., administration by infusion, injection, implantation, etc., as is well known in the art. Examples include bolus injection or continuous infusion. Intratumoral administration, for example by injection, is also contemplated.

Such pharmaceutical compositions can be prepared by methods well known in the art. See, e.g., *Remington: The Science and Practice of Pharmacy,* 21$^{st}$ Edition (2005), Lippincott Williams & Wilkins, Philadelphia, Pa., and comprise one or more antibody compounds disclosed herein, and a pharmaceutically or veterinarily acceptable, e.g., physiologically acceptable, carrier, diluent, or excipient.

Combination Therapies

The therapeutic methods encompassed herein include the use of the antibodies disclosed herein alone, and/or in combinations with one another, and/or with antigen-binding fragments thereof, and/or with competing antibodies exhibiting appropriate biological/therapeutic activity, as well, i.e., all possible combinations of these antibody compounds.

In addition, the present therapeutic methods also encompass the use of these antibodies, antigen-binding fragments thereof, competing antibodies, etc., and combinations thereof further in combination with: (1) any one or more of the nitric oxide donor, precursor, or nitric oxide generating topical agents, and/or agents that activate soluble guanylyl cyclase, and/or agents that inhibit cyclic nucleotide phosphodiesterases disclosed herein, or (2) any one or more anti-tumor therapeutic treatments selected from surgery, radiation, anti-tumor or anti-neoplastic agents, and combinations of any of these, or (3) equivalents of any of the foregoing of (1) or (2) as would be apparent to one of ordinary skill in the art, in appropriate combination(s) to achieve the desired therapeutic treatment effect for the particular indication.

Combinations of Antibody Compounds

It should be noted that in all of the therapeutic methods disclosed and claimed herein, the monoclonal antibodies or antigen binding fragments thereof, and monoclonal antibodies or antigen binding fragments thereof that compete with these monoclonal antibodies or antigen binding fragments thereof of the present disclosure that bind to CD47, can be used alone, or in any appropriate combinations with one another, to achieve the greatest treatment efficacy.

Further Therapeutic Combinations to Treat IRI-Related Indications

In addition to administering the combinations of antibody compounds as described immediately above, the methods of the present disclosure, for example those related to treatment of IRI-related indications, can further comprise administering to a patient in need thereof an effective amount of a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

In these methods, the nitric oxide donor or precursor can be selected from NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine.

The agent that activates soluble guanylyl cyclase can be a non-NO (nitric oxide)-based chemical activator of soluble guanylyl cyclase that increases cGMP levels in vascular cells. Such agents bind soluble guanylyl cyclase in a region other than the NO binding motif, and activate the enzyme regardless of local NO or reactive oxygen stress (ROS). Non-limiting examples of chemical activators of soluble guanylyl cyclase include organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marietta (2012) *Ann. Rev. Biochem.* 81:533-559, and Nossaman et al. (2012) *Critical Care Research and Practice,* Volume 2012, Article ID 290805, pages 1-12.

The agent that inhibits cyclic nucleotide phosphodiesterases can be selected from sildenafil, tadalafil, vardenafil, udenafil, and avanafil.

Further Therapeutic Combinations to Treat Cancer Indications

In addition to the foregoing, the methods of the present disclosure, for example those related to treatment of cancer indications, can further comprise treating the patient via surgery, radiation, and/or administering to a patient in need thereof an effective amount of a chemical small molecule or biologic drug including, but not limited to, a peptide, polypeptide, protein, nucleic acid therapeutic, etc., conventionally used, or currently being developed, to treat tumorous conditions. This includes antibodies and antigen-binding fragments other than those disclosed herein, cytokines, antisense oligonucleotides, siRNAs, miRNAs, etc.

As is well known to those of ordinary skill in the art, combination therapies are often employed in cancer treatment as single-agent therapies or procedures may not be sufficient to treat or cure the disease or condition. Conventional cancer treatments often involve surgery, radiation treatment, the administration of a combination of cytotoxic drugs to achieve additive or synergistic effects, and combinations of any or all of these approaches. Especially useful chemotherapeutic and biologic therapy combinations employ drugs that work via different mechanisms of action, increasing cancer cell control or killing, increasing the ability of the immune system to control cancer cell growth, reducing the likelihood of drug resistance during therapy, and minimizing possible overlapping toxicities by permitting the use of reduced doses of individual drugs.

Classes of conventional anti-tumor/anti-neoplastic agents useful in the combination therapies encompassed by the present methods are disclosed, for example, in *Goodman & Gilman's The Pharmacological Basis of Therapeutics*, Twelfth Edition (2010) L. L. Brunton, B. A. Chabner, and B. C. Knollmann Eds., Section VIII, "Chemotherapy of Neoplastic Diseases", Chapters 60-63, pp. 1665-1770, McGraw-Hill, NY, and include, for example, alkylating agents; antimetabolites; natural products; a variety of miscellaneous agents; hormones and antagonists; and monoclonal antibodies.

Antibody and small molecule drugs that increase the immune response to cancer by modulating co-stimulatory or inhibitory interactions that influence the T cell response to tumor antigens, including inhibitors of immune checkpoints and modulators of co-stimulatory molecules, are also of particular interest in the context of the combination therapeutic methods encompassed herein and include, but are not limited to, other anti-CD47 antibodies. Combinations of the present, and other, anti-CD47 antibodies with inhibitors of PD1, PD-L1, PD-L2, CTLA-4, BTLA, indoleamine 2,3-dioxygenase, TIM3, A2A adenosine receptor, CD37 (ecto-nucleoside triphosphate diphosphohydrolase-1), and CD73 (ecto-5'-nucleotidase), including antibodies and small molecules, and agonists of CD27, ICOS, CD137, OX40, 4-1BB, and TNFSF25, including small molecules and antibodies, are also specifically contemplated herein.

YERVOY® (ipilimumab; Bristol-Meyers Squibb) is an example of an approved anti-CTLA-4 antibody.

Another useful class of compounds for the combination therapies contemplated herein includes modulators of SIRPalpha/CD47 binding such as antibodies to SIRPalpha, as well as soluble protein fragments of this ligand, or CD47 itself, acting as "decoy" molecules inhibiting binding of, or interfering with binding of, SIRPalpha to CD47.

The present disclosure encompasses therapeutic methods comprising not only the administration of any of the individual monoclonal antibodies, antigen binding fragments thereof, or competing antibodies disclosed herein with any one or more of the molecules discussed immediately above, but also combinations of the disclosed monoclonal antibodies, antigen-binding fragments thereof, and competing antibodies in combinations with any one or more of the molecules discussed immediately above, i.e., all possible permutations and combinations of the presently disclosed molecules.

The term "tumor" refers to all neoplastic cell growth and proliferation, whether malignant or benign, and all pre-cancerous and cancerous cells and tissues. The terms "cancer", "cancerous", and "tumor" are not mutually exclusive as used herein.

The terms "cancer" and "cancerous" refer to or describe the physiological condition in mammals that is typically characterized by aberrant cell growth/proliferation. Examples of cancers include, but are not limited to, carcinomas, lymphomas, blastomas, sarcomas, and leukemias.

The term "susceptible cancer" as used herein refers to a cancer, cells of which express CD47 and that are responsive to treatment with an antibody or antigen binding fragment thereof, or competing antibody or antigen binding fragment thereof, of the present disclosure. Exemplary susceptible cancers include, but are not limited to, leukemias, including acute lymphocytic (lymphoblastic) leukemia, acute myeloid leukemia, myelogenous leukemia, chronic lymphocytic leukemia, multiple myeloma, chronic myeloid leukemia, and plasma cell leukemia; lymphomas, including Hodgkin lymphoma and Non-Hodgkin lymphoma, including B cell lymphoma, diffuse large B cell lymphoma, follicular lymphoma, mantle cell lymphoma, marginal zone B cell lymphoma, T cell lymphoma, and Waldenstrom macroglobulinemia; ovarian cancer; breast cancer; endometrial cancer; colon cancer; rectal cancer; bladder cancer; lung cancer; bronchial cancer; bone cancer; prostate cancer; pancreatic cancer; gastric cancer; liver and bile duct cancer; esophageal cancer; renal cancer; thyroid cancer; head and neck cancer; testicular cancer; glioblastoma; astrocytoma; melanoma; myelodysplastic syndrome; and sarcomas including, but not limited to, osteosarcoma, Ewing sarcoma, leiomyosarcoma, synovial sarcoma, alveolar soft part sarcoma, angiosarcoma, liposarcoma, fibrosarcoma, rhabdomyosarcoma, and chrondrosarcoma.

"Phagocytosis" of cancer cells refers to the engulfment and digestion of such cells by macrophages, and the eventual digestion or degradation of these cancer cells and their release extracellularly, or intracellularly, to undergo further processing. Anti-CD47 monoclonal antibodies that block SIRPalpha binding to CD47, the "don't eat me" signal which is highly expressed on cancer cells as compared with normal cells, induce macrophage phagocytosis of cancer cells. SIRPalpha binding to CD47 on cancer cells would otherwise allow these cells to escape macrophage phagocytosis.

The terms "promote", "promoting", and the like are used herein synonymously with "increase", "increasing", etc.

"Ischemia" refers to a vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply. Ischemia can occur acutely, as during surgery, or from trauma to tissue incurred in accidents, injuries and war settings, or following harvest of organs intended for subsequent transplantation, for example. It can also occur sub-acutely, as found in atherosclerotic peripheral vascular disease, where progressive narrowing of blood vessels leads to inadequate blood flow to tissues and organs.

When a tissue is subjected to ischemia, a sequence of chemical events is initiated that may ultimately lead to cellular dysfunction and necrosis. If ischemia is ended by the restoration of blood flow, a second series of injurious events ensue, producing additional injury. Thus, whenever there is a transient decrease or interruption of blood flow in a subject, the resultant injury involves two components—the direct injury occurring during the ischemic interval, and the indirect or reperfusion injury that follows.

"Ischemic stroke" can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism). Cerebral stroke can occur when atherosclerotic plaque separates away partially from the vessel wall and occludes the flow of blood through the blood vessel.

"Reperfusion" refers to restoration of blood flow to tissue that is ischemic, due to decrease in blood flow. Reperfusion is a procedure for treating infarction or other ischemia, by enabling viable ischemic tissue to recover, thus limiting further necrosis. However, reperfusion can itself further damage the ischemic tissue, causing reperfusion injury.

In addition to the immediate injury that occurs during deprivation of blood flow, "ischemic/reperfusion injury" involves tissue injury that occurs after blood flow is restored. Current understanding is that much of this injury is caused by chemical products, free radicals, and active biological agents released by the ischemic tissues.

"Nitric oxide donor, precursor, or nitric oxide generating topical agent" refers to a compound or agent that either delivers NO, or that can be converted to NO through enzymatic or non-enzymatic processes. Examples include, but are not limited to, NO gas, isosorbide dinitrite, nitrite, nitroprusside, nitroglycerin, 3-Morpholinosydnonimine (SIN-1), S-nitroso-N-acetyl-penicillamine (SNAP), Diethylenetriamine/NO (DETA/NO), S-nitrosothiols, Bidil®, and arginine.

"Soluble guanylyl cyclase (sGC)" is the receptor for nitric oxide in vascular smooth muscle. In the cardiovascular system, nitric oxide is endogenously generated by endothelial nitric oxide synthase from L-arginine, and activates soluble guanylyl cyclase in adjacent vascular smooth muscle cells to increase cGMP levels, inducing vascular relaxation. Nitric oxide binds to the normally reduced heme moiety of soluble guanylyl cyclase, and increases the formation of cGMP from GTP, leading to a decrease in intracellular calcium, vasodilation, and anti-inflammatory effects. Oxidation of the heme iron on sGC decreases responsiveness of the enzyme to nitric oxide, and promotes vasoconstriction. The nitric oxide-sGC-cGMP pathway therefore plays an important role in cardiovascular diseases. Nitrogen-containing compounds such as sodium azide, sodium nitrite, hydroxylamine, nitroglycerin, and sodium nitroprusside have been shown to stimulate sGC, causing an increase in cGMP, and vascular relaxation. In contrast to stimulators of sGC, which bind to reduced sGC, activators of sGC activate the oxidized or heme-deficient sGC enzyme that is not responsive to nitric oxide, i.e., they stimulate sGC independent of redox state. While stimulators of of sGC can enhance the sensitivity of reduced sGC to nitric oxide, activators of sGC can increase sGC enzyme activity even when the enzyme is oxidized and is therefore less, or unresponsive, to nitric oxide. Thus, sGC activators are non-nitric oxide based. Note the reviews of Nossaman et al. (2012) *Critical Care Research and Practice*, Volume 2012, article 290805, and Derbyshire and Marietta (2012) *Ann. Rev. Biochem.* 81:533-559.

"An agent that activates soluble guanylyl cyclase" refers, for example, to organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marietta (2012) *Ann. Rev. Biochem.* 81:533-559, and Nossaman et al. (2012) *Critical Care Research and Practice*, Volume 2012, Article ID 290805, pages 1-12.

Examples of "an agent that inhibits cyclic nucleotide phosphodiesterases" include sildenafil, tadalafil, vardenafil, udenafil, and avanafil.

The singular terms "a", "an", and "the" include plural referents unless context clearly indicates otherwise. Similarly, the word "or" is intended to include "and" unless the context clearly indicates otherwise. Hence, comprising A or B means including A, or B, or A and B.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 9%, up to 8%, up to 7%, up to 6%, up to 5%, up to 4%, up to 3%, up to 2%, or up to 1% compared to the specifically recited value.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary.

Furthermore, the use of the term "including", as well as other related forms, such as "includes" and "included", is not limiting.

CD47 and Ischemia-Reperfusion Injury (IRI)

Following periods of tissue ischemia, the initiation of blood flow causes damage referred to as "ischemia-reperfusion injury" or IRI. IRI contributes to poor outcomes in many surgical procedures where IRI occurs due to the necessity to stop blood flow for a period of time, in many forms/causes of trauma in which blood flow is interrupted and later restored by therapeutic intervention and in procedures required for organ transplantation, cardio/pulmonary bypass procedures, reattachment of severed body parts, reconstructive and cosmetic surgeries and other situations involving stopping and restarting blood flow. Ischemia itself causes many physiological changes that, by themselves would eventually lead to cell and tissue necrosis and death. Reperfusion poses its own set of damaging events including generation of reactive oxygen species, thrombosis, inflammation and cytokine mediated damage. The pathways that are limited by the TSP1-CD47 system are precisely those that would be of most benefit in combating the damage of IRI. Thus, blocking the TSP1-CD47 pathway, as with the antibody compounds disclosed herein, will provide more robust functioning of these endogenous protective pathways.

The humanized anti-CD47 antibodies, antigen binding fragments thereof, and competing antibodies and antigen binding fragments thereof, of the present disclosure can be used in the methods disclosed in U.S. Pat. No. 8,236,313, the contents of which are herein incorporated by reference in their entirety.

CD47 and Cancer

CD47 has been identified as a novel therapeutic target in hematologic cancers (Majeti et al. (2009) *Cell* 138(2):286-99), as well as in solid tumors such as colon, prostate, breast, and brain cancers (Willingham et al. (2012) *Proc Natl Acad Sci USA* 109(17):6662-7). Many human cancers up-regulate cell surface expression of CD47, and those expressing the highest levels of CD47 are the most aggressive and the most lethal for patients. Increased CD47 expression is thought to protect cancer cells from phagocytic clearance by sending a "don't eat me" signal to macrophages via SIRPalpha, an inhibitory receptor that prevents phagocytosis of CD47-bearing cells (Jaiswal et al. (2009) *Cell* 138(2):271-851; Chao et al. (2010) *Science Translational Medicine* 2(63): 63ra94). Thus, the increase of CD47 expression by many cancers provides them with a cloak of "selfness" that slows their phagocytic clearance by macrophages and dendritic cells. Anti-CD47 mAbs (CD47mAbs) that block the CD47/SIRPalpha interaction enhance phagocytosis of cancer cells in vitro and contribute to control of tumor burden in published human to mouse xenograft tumor models.

Antibodies that block CD47 and prevent its binding to SIRPalpha ("blocking mAbs") have shown efficacy in human tumor in mouse (xenograft) tumor models. Such blocking CD47mAbs exhibiting this property promote (increase) the phagocytosis of cancer cells by macrophages, which can reduce tumor burden (Majeti et al. (2009) *Cell* 138(2):286-99) and may ultimately lead to generation of an adaptive immune response to the tumor (Tseng et al. (2013) *Proc Natl Acad Sci* USA. 110(27):11103-8).

Therapeutic Indications

IRI-Related and Autoimmune/Inflammatory Conditions

Administration of a CD47 mAb or antigen binding fragment thereof disclosed herein can be used to treat a number of diseases and conditions in which IRI is a contributing feature, and to treat various autoimmune and inflammatory diseases. These include: organ transplantation in which a mAb or antigen binding fragment thereof of the present disclosure is administered to the donor prior to organ harvest, to the harvested donor organ, to the organ preservation solution, to the recipient patient, or to any combination thereof; skin grafting; surgical resections or tissue reconstruction in which such mAb or fragment is administered either locally by injection to the affected tissue or parenterally to the patient; reattachment of body parts; treatment of traumatic injury; pulmonary hypertension; sickle cell disease (crisis); myocardial infarction; stroke; surgically-induced ischemia; acute kidney disease/kidney failure; any other condition in which IRI occurs and contributes to the pathogenesis of disease; and autoimmune/inflammatory diseases, including arthritis, multiple sclerosis, psoriasis, Crohn's disease, inflammatory bowel disease, lupus, Grave's disease and Hashimoto's thyroiditis, and ankylosing spondylitis.

CD47 mAbs and antigen binding fragments thereof of the present disclosure can also be used to increase tissue perfusion in a subject in need of such treatment. Such subjects can be identified by diagnostic procedures indicating a need for increased tissue perfusion. In addition, the need for increased tissue perfusion may arise because the subject has had, is having, or will have, a surgery selected from integument surgery, soft tissue surgery, composite tissue surgery, skin graft surgery, resection of a solid organ, organ transplant surgery, or reattachment or an appendage or other body part.

Susceptible Cancers

Presently disclosed mAbs and antigen binding fragments thereof effective as cancer therapeutics can be administered to patients, preferably parenterally, with susceptible hematologic cancers and solid tumors including, but not limited to, leukemias, including acute lymphocytic (lymphoblastic) leukemia, acute myeloid leukemia, myelogenous leukemia, chronic lymphocytic leukemia, multiple myeloma, chronic myeloid leukemia, and plasma cell leukemia; lymphomas, including Hodgkin lymphoma and Non-Hodgkin lymphoma, including B cell lymphoma, diffuse large B cell lymphoma, follicular lymphoma, mantle cell lymphoma, marginal zone B cell lymphoma, T cell lymphoma, and Waldenstrom macroglobulinemia; ovarian cancer; breast cancer; endometrial cancer; colon cancer; rectal cancer; bladder cancer; lung cancer; bronchial cancer; bone cancer; prostate cancer; pancreatic cancer; gastric cancer; liver and bile duct cancer; esophageal cancer; renal cancer; thyroid cancer; head and neck cancer; testicular cancer; glioblastoma; astrocytoma; melanoma; myelodysplastic syndrome; and sarcomas including, but not limited to, osteosarcoma, Ewing sarcoma, leiomyosarcoma, synovial sarcoma, alveolar soft part sarcoma, angiosarcoma, liposarcoma, fibrosarcoma, rhabdomyosarcoma, and chrondrosarcoma.

In certain cases, it may be advantageous to administer the mAb directly to the cancer by injection into the tumor.

Since CD47 expression is up-regulated on many cancers, it may also be desirable to use one or more of the disclosed mAbs as imaging and diagnostic agents when labeled with radioactive or other tracers known to those skilled in the art of in vivo imaging of cancers/tumors.

The following examples describe various aspects of the present disclosure, but should not be considered as limiting the disclosure only to these particularly disclosed embodiments. The materials and methods employed in these examples are for illustrative purposes, and are not intended to limit the practice of the present disclosure thereto. Any materials and methods similar or equivalent to those described herein as would be apparent to one of ordinary skill in the art can be used in the practice or testing of the present compounds and methods.

Example 1

Production of CD47 Antibodies

The humanized antibodies disclosed herein comprise frameworks derived from the human genome. The collection covers the diversity found in the human germ line sequences, yielding functionally expressed antibodies in vivo. The complementarity determining regions (CDRs) in the light and heavy chain variable regions of the target chimeric, non-human antibody VxP037-01LC/VxP037-01HC (SEQ ID NO:7/SEQ ID NO:57) are determined following commonly accepted rules disclosed, for example, in "Protein Sequence and Structure Analysis of Antibody Variable Domains", In: *Antibody Engineering Lab Manual*, Eds. S. Duebel and R. Kontermann, Springer-Verlag, Heidelberg (2001)). The CDR fragments are synthesized and combined with pools of frameworks to generate full length variable domains. The humanized variable domains are then combined with a secretion signal and human kappa and human IgG1 constant domains, and cloned into a mammalian expression system (e.g., OptiCHO System, Lifetechnologies, Carlsbad, Calif.) to generate a library of humanized IgG1, IgG2, and IgG4 variants. An aliquot of the library is sequenced to ensure high diversity and integrity of the reading frames of the individual clones. Aliquots of the humanized variant library are then re-arrayed as single clones into 96 well plates, mini-prepped (e.g., 96 well Miniprep Kit, Qiagen Hilden, Germany), and transfected into CHO cells (Lipofectamine transfection protocol as recommended by Lifetechnologies, Carlsbad, Calif.). Transfected CHO cells are grown in DMEM medium with 10% FBS (both from Lifetechnologies, Carlsbad, Calif.) at 37° C. under 5% $CO_2$. The humanized variants are expressed as full length IgG1 molecules, and secreted into the medium.

The cell culture supernatant containing the humanized IgG variants is then screened for binding to the target antigen, CD47. In parallel, the concentration of each variant is determined in order to calculate specific activity for each clone. The specific activity of each clone is compared to the specific activity of chimeric clone VxP037-01LC-Pro/VxP037-01HC-Pro (SEQ ID NO:107/SEQ ID NO:109) expressed on the same plate, and normalized. Top hits from each plate are re-arrayed and re-screened for confirmation. The final candidates are selected by specific activity, functional activity, expression level, and sequence diversity, as well as other criteria, as described below.

A non-glycosylated version (IgG1-N297Q) was created by site directed mutagenesis of heavy chain position 297 to change the asparagine to glutamine (pVxP037-01-HC-IgG1 N297Q-Pro; SEQ ID NO:111). IgG2 and IgG4-S228P isotypes were constructed by cloning the heavy chain variable domain in frame with the human IgG2 and IgG4-S228P constant domains (pVxK7b-037-hum01-HC-IgG2-Pro, SEQ ID NO:112 or pVxK7b-037-hum01-HC_IgG4 S228P-Pro, SEQ ID NO:113).

Example 2

CD47 Antibody Sequences

The amino acid sequences of the light chain and heavy chain variable regions, the complete light and heavy chains, and the respective encoding nucleotide sequences of the foregoing, of the present human engineered antibodies are listed below in the section entitled "Amino Acid and Nucleic Acid Sequences."

Also included in this list are complete light chain sequences (SEQ ID NO:107/SEQ ID NO:108), complete heavy chain amino acid and respectively encoding nucleotide sequences of humanized IgG1 (SEQ ID NO:109/SEQ ID NO:110), complete heavy chain amino acid and respectively encoding nucleotide sequences of humanized IgG1 with a N→Q mutation at amino acid position 297 (SEQ ID NO:111/SEQ ID NO:114), IgG2 (SEQ ID NO:112/SEQ ID NO:115), and IgG4 (SEQ ID NO:113/SEQ ID NO:116) antibodies.

SEQ ID NO:117 shows the amino acid sequence of framework 4+the light chain constant domain amino acid sequence of chimeric complete light chain amino acid sequence SEQ ID NO:107.

SEQ ID NOs:118, 119, 120, and 121 show the amino acid sequences of framework 4+the heavy chain constant domain amino acid sequences of complete heavy chain amino acid sequences SEQ ID NOs:109, 111, 112, and 113, respectively.

All the light chain variable regions SEQ ID NOs:7-31 can further comprise SEQ ID NO:117, and all the heavy chain amino acid sequences SEQ ID NOs:57-81 can further comprise any of SEQ ID NOs:118, 119, 120, and 121, thereby describing complete antibody sequences encompassed by this disclosure.

The light chain and heavy chain CDR amino acid sequences are shown in Tables 1 and 2, respectively.

TABLE 1

Light Chain CDRs

| CDR1 | CDR2 | CDR3 |
|---|---|---|
| RSSQSLVHSNGNTYLH (SEQ ID NO: 1) | KVSYRFS (SEQ ID NO: 2) | SQNTHVPRT (SEQ ID NO: 3) |

TABLE 2

Heavy Chain CDRs

| CDR1 | CDR2 | CDR3 |
|---|---|---|
| GYTFTNYYVF (SEQ ID NO: 4) | DINPVNGDTNFNEKFKN (SEQ ID NO: 5) | GGYTMDY (SEQ ID NO: 6) |

Example 3

Binding of Antibodies to CD47 of Different Species

Cross species reactivity of humanized antibodies of the present disclosure is determined using freshly isolated red blood cells (RBCs), which display CD47 on their surface, from human, mouse, rat, pig, cynomolgus monkey, and dog according to the methods disclosed in Kamel et al. (2010) *Blood. Transfus.* 8(4):260-266.

Supernatants containing secreted antibodies are collected from CHO cells transiently transfected with plasmids encoding antibody clones and used as collected, or antibodies are further purified from the supernatants using standard methods. Transfected CHO cells are grown in F-12 medium containing 10% heat inactivated fetal bovine serum (BioWest; S01520). Antibody concentration in the supernatants is determined utilizing a quantitative ELISA. ELISA plates are coated with a donkey anti-human FC antibody (Sigma; Catalog #12136) at 10 μg/ml overnight at 4° C. (Promega; Catalog # W4031). Plates are washed with PBS, and then blocked with casein blocking solution (ThermoScientific; Catalog #37532) for 60 minutes at room temperature. Plates are again washed with PBS, tissue culture supernatants are added, and the plates are incubated for 60 minutes at room temperature. Plates are then washed three times with PBS and incubated with peroxidase-conjugated goat anti-human IgG (Jackson Immunoresearch Labs; Catalog #109-035-003) for 60 minutes at room temperature. Plates are washed three times with PBS, and the peroxidase substrate 3,3',5, 5'-tetramethylbenzidine is added (Sigma; Catalog # T4444). Reactions are terminated by the addition of HCl to 0.7N, and absorbance at 450 nM is determined using a Tecan model Infinite M200 plate reader.

RBCs are incubated for 60 minutes on ice with tissue culture supernatants containing the secreted humanized antibodies at a concentration of 10 ng/ml in a solution of phosphate buffered saline, pH 7.2, 2.5 mM EDTA (PBS+E), or with various concentrations of purified antibodies. Cells are then washed with cold PBS+E, and incubated for an additional hour on ice with FITC labeled donkey anti-human antibody (Jackson Immuno Research Labs, West Grove, Pa.; Catalogue #709-096-149) in PBS+E. Cells are then washed with PBS+E, and antibody binding is analyzed using a BD FACSAria Cell Sorter (Becton Dickinson) or a C6 Accuri Flow Cytometer (Becton Dickinson). Antibody binding is quantitated by comparison of mean fluorescence values relative to that of chimeric antibody >VxP037-01LC (SEQ ID NO:7))/>VxP037-01HC (SEQ ID NO:57). The mean fluorescence value for each antibody is divided by the mean fluorescence value for the chimeric antibody.

The results obtained from the supernatants are shown in Table 3, where "Chimera" represents chimeric antibody >VxP037-01LC (SEQ ID NO:7))/>VxP037-01HC (SEQ ID NO:57; complete sequences VxP037-01LC-Pro/VxP037-01HC-Pro (SEQ ID NO:107/SEQ ID NO:109)), Clone 1 represents >pVxK7b-037-hum01-LC (SEQ ID NO:8)/>pVxK7b-037-hum01-HC (SEQ ID NO:58), Clone 2 represents >pVxK7b-037-hum02-LC (SEQ ID NO:9)/>pVxK7b-037-hum02-HC (SEQ ID NO:59), and so on similarly for remaining clones 3-24. Each antibody also contains a light chain constant domain (SEQ ID:117) and a heavy chain constant domain selected from among SEQ ID NO:118, SEQ ID NO:119, SEQ ID NO:120, and SEQ ID NO:121.

TABLE 3

Binding of Humanized Antibodies to CD47 on the Surface of Red Blood Cells of Different Mammalian Species

| Clone No. | Human | Mouse | Rat | Pig | Dog |
|---|---|---|---|---|---|
| Chimera | 1.0 | 1.0 | 1.0 | 1.0 | 1.0 |
| 1 | 1.1 | 1.7 | 2.7 | 1.3 | 1.0 |
| 2 | 1.0 | 1.2 | 2.6 | 1.2 | 1.0 |
| 3 | 0.7 | 0.9 | 1.7 | 0.9 | 0.9 |
| 4 | 0.6 | 0.6 | 1.0 | 0.6 | 0.6 |
| 5 | 1.0 | 1.0 | 2.2 | 1.2 | 1.1 |
| 6 | 0.9 | 1.2 | 2.1 | 1.1 | 1.1 |
| 7 | 0.5 | 0.4 | 0.8 | 0.9 | 0.8 |
| 8 | 0.7 | 0.7 | 1.2 | 0.8 | 0.8 |
| 9 | 1.2 | 1.4 | 3.7 | 1.6 | 1.0 |
| 10 | 1.1 | 1.2 | 2.9 | 1.5 | 1.1 |
| 11 | 0.8 | 0.7 | 1.2 | 1.2 | 0.8 |
| 12 | 0.8 | 0.6 | 1.3 | 1.4 | 0.9 |
| 13 | 1.2 | 1.3 | 3.1 | 1.4 | 1.0 |
| 14 | 1.1 | 1.5 | 3.2 | 1.4 | 1.3 |
| 15 | 1.0 | 1.3 | 2.4 | 1.2 | 1.1 |
| 16 | 0.9 | 1.0 | 2.1 | 1.1 | 1.1 |
| 17 | 0.8 | 0.9 | 2.1 | 1.3 | 1.3 |
| 18 | 1.0 | 1.3 | 2.2 | 1.2 | 1.5 |
| 19 | 0.7 | 1.0 | 2.6 | 1.3 | 1.2 |
| 20 | 1.3 | 1.5 | 1.9 | 1.7 | 1.1 |
| 21 | 1.2 | 1.2 | 2.8 | 1.4 | 1.1 |
| 22 | 1.1 | 1.2 | 2.8 | 1.4 | 1.0 |
| 23 | 1.2 | 1.4 | 3.3 | 1.7 | 1.1 |
| 24 | 0.8 | 0.7 | 1.2 | 1.1 | 1.0 |

FIG. 1 shows cross species binding curves to human, mouse, rat, and porcine RBCs (panels A, B, C, and D, respectively, generated using various concentrations of purified antibodies from clones Cl 1, Cl 1.1, Cl 13, and Cl 13.1. Clones Cl 1 and Cl 13 are as described above in Table 3. Clones Cl 1.1 and Cl 13.1 are Fc mutants of clones Cl 1 and Cl 13, respectively, modified to reduce effector function. Each has an Asn297→Gln(N297Q) mutation in the Fc domain (Sazinsky et al. (2008) PNAS 105(51):20167-20172). All of these clones exhibit concentration-dependent binding to all of the species of RBCs tested. These clones also bind to cynomolgus monkey RBCs (data not shown).

Table 4 shows the apparent affinities of these clones to human RBCs determined by non-linear fits (Prism Graphpad software) of the median fluorescence intensities at various antibody concentrations. Clones 1, 1.1, 13, and 13.1 all have apparent Kd values in the low nanomolar range.

TABLE 4

Binding Affinity of Humanized Antibodies to CD47 on Human RBCs

|  | Clone 1 | Clone 1.1 | Clone 13 | Clone 13.1 |
|---|---|---|---|---|
| Kd (ng/ml) | 226.2 | 307.1 | 86.4 | 182.9 |
| Kd (apparent) nM | 1.51 | 2.04 | 0.58 | 1.21 |

These data demonstrate that all of the humanized CD47 mAb clones disclosed herein bind well to CD47 of a variety of different mammalian species, confirming the useful cross-species reactivity of these antibodies.

Example 4

Antibodies to CD47 Enhance Phagocytosis

To assess the effect of humanized CD47 mAbs on phagocytosis of tumor cells by marcrophages in vitro the following method is employed using flow cytometry, essentially as described by Willingham et al. (2012) Proc Natl Acad Sci USA 109(17):6662-7 and Tseng et al. (2013) Proc Natl Acad Sci USA 110(27):11103-8.

Human derived macrophages are derived from leukapheresis of healthy human peripheral blood incubated in human AB serum (Sigma Aldrich) for 24 hours in culture. After 24 hours, all non-adherent cells are removed and the remaining adherent macrophages are incubated in RPMI medium (10% fetal bovine serum (FBS; Hyclone) and antibiotics) for two weeks. For the in vitro phagocytosis assay, macrophages are re-plated at a concentration of $5 \times 10^4$ cells per well in 1 ml of RPMI media in a 24 well plate and allowed to adhere for 24 hours. Once the effector macrophages have adhered to the culture dish, the target cancer cells (Jurkat) are labeled with 1 μM 5(6)-Carboxyfluorescein diacetate N-succinimidyl ester (CFSE; Sigma Aldrich) and added to the macrophage cultures at a concentration of $2 \times 10^5$ cells in 1 ml of RPMI media (4:1 target to effector ratio). CD47mAbs (10 μg/ml) are added immediately upon mixture of target and effector cells and allowed to incubate at 37° C. for 2 hours. After 2 hours, all non-phagocytosed cells are removed and the remaining cells are washed three times with phosphate buffered saline (PBS; Sigma Aldrich). Cells are trypsinized, collected into microcentrifuge tubes and incubated in 100 ng of allophycocyanin (APC) labeled CD14 antibodies (BD biosciences) for 30 minutes. Cells are washed once and analyzed by flow cytometry (Accuri C6; BD biosciences) for the percentage of CD14 positive cells that are also CFSE positive indicating complete phagocytosis.

As shown in FIG. 2, both Clone 1 and Clone 13 humanized mAbs increase phagocytosis of Jurkat cells. Clones 1.1 and Clone 13.1 are identical to Clones 1 and 13 except for a mutation of residue N297 to Q which reduces the affinity of the IgG1 molecule to the Fc receptor. The IgG4 versions of Clone 1 and Clone 13 also increase phagocytosis of Jurkat cells. The IgG4 isotype also has reduced affinity for activating Fc receptors.

Therefore, all isotypes/mutants of Clone 1 and 13 enhance phagocytosis via blocking the CD47/SIRPalpha interaction.

Example 5

Antibodies to CD47 Regulate Nitric Oxide Signaling

The purpose of this experiment is to demonstrate that humanized antibody clones of the present disclosure exhibit the ability to reverse TSP1-mediated inhibition of NO-stimulated cGMP synthesis as, for example, described previously using mouse monoclonal antibodies to CD47 as disclosed by Isenberg et al. (2006) *J. Biol. Chem.* 281: 26069-80.

The method employed to measure cGMP is as described by the manufacturer (CatchPoint Cyclic-GMP Fluorescent Assay Kit, Molecular Devices, Sunnyvale, Calif.). Jurkat JE6.1 cells (ATCC, Manassas, Va.; Catalog # TIB-152) are used as these cells retain the NO-cGMP signaling pathway when grown in culture and exhibit a robust and reproducible inhibitory response to TSP1 ligation of CD47. Cells are grown in Iscove's modified Dulbeccco's medium containing 5% (v/v) heat inactivated fetal bovine serum (BioWest; Catalogue # S01520), 100 units/mL penicillin, 100 μg mL streptomycin (Sigma; Catalogue # P4222) at densities less than $1 \times 10^6$ cells/mL. For the cGMP assay, cells are plated in 96 well tissue culture plates at a density of $1 \times 10^5$ cells/ml in Iscoves modified Dulbecco's medium containing 5% (v/v) heat inactivated fetal bovine serum (BioWest; Catalog # S01520), 100 units/mL penicillin, 100 μg/mL streptomycin (Sigma; # P4222) for 24 hours and then transferred to serum free medium overnight.

The humanized antibodies as disclosed herein, purified from transient transfections in CHO cells as described above in Example 3, as well as the control chimeric antibody, are then added at a final concentration of 20 ng/ml, followed 15 minutes later by 0 or 1 μg/ml human TSP1 (Athens Research and Technology, Athens, Ga., Catalogue #16-20-201319). After an additional 15 minutes, the NO donor, diethylamine (DEA) NONOate (Cayman Chemical, Ann Arbor, Mich., Catalog #82100), is added to half the wells at a final concentration of 1 μM. Five minutes later, the cells are lysed with buffer supplied in the cGMP kit, and aliquots of each well are assayed for cGMP content.

As shown in FIGS. 3 and 4, none of the present humanized antibody clones tested, or the chimeric control mAb, has an effect on basal cGMP levels. As expected, the chimeric antibody VxP037-01LC-Pro/VxP037-01HC-Pro (SEQ ID NO:107/SEQ ID NO:109)) reverses the TSP1 inhibition.

Humanized clones 1, 9, 11, 13, and 24 of the present disclosure also significantly reverse TSP1 inhibition, demonstrating that they have the ability to increase NO signaling (FIGS. 3 and 4), suggesting their utility in protecting the cardiovascular system against stresses including, but not limited to, those resulting from wounding, inflammation, hypertension, metabolic syndrome, ischemia, and ischemia-reperfusion injury (IRI).

Example 6

Reduction of Ischemia-Reperfusion Injury In Vivo

The purpose of this experiment is to demonstrate that a humanized antibody clone disclosed herein, i.e., Clone 1, that is shown to regulate nitric oxide signaling in vitro in Example 5, is effective in reducing IRI and kidney damage in vivo in a rat kidney transplant model under standard conditions, i.e., with no warm ischemic time but with cold ischemic time. IRI significantly contributes to delayed graft function and inflammation leading to graft loss, and is exacerbated by the thrombospondin-1/CD47 system through inhibition of nitric oxide signaling.

A syngeneic rat renal transplantation model of IRI with bilaterally nephrectomized recipients is used to evaluate the effect of the anti-CD47 monoclonal antibody Clone 1 on graft function following transplantation as described in Schumacher et al. (2003) *Microsurg.* 23:389-394 and Karatzas et al. (2007) *Microsug.* 27:668-672.

Male Lewis rats weighing 275-300 g are obtained from Charles River Laboratories (Wilmington, Mass.). Donor kidneys are flushed with 50 μg of purified Clone 1 or vehicle (phosphate buffered saline, pH 7.2), and stored at 4° C. in University of Wisconsin preservation solution (UW) for 6 hours prior to transplantation. Two days following transplantation, kidney function is assessed by measuring serum creatinine by standard methodology.

As shown in FIG. 5, CD47mAb Clone 1 perfusion of donor kidneys results in improved kidney function compared to controls as measured by a reduction in serum creatinine.

An additional experiment is shown that also demonstrates the ability of CD47mAbs of the present disclosure to improve kidney function of extended criteria organs that have also undergone a 60 minute period of warm ischemic time in addition to a 6 hour cold ischemic time. Male Lewis rats weighing 275-300 g underwent 60 minutes of warm ischemia, prior to flushing the donor kidneys with 50 μg of purified Clone 1.1 or an IgG control mAb. Kidneys are stored at 4° C. in University of Wisconsin preservation solution (UW) for 6 hours prior to transplantation. In this experiment, survival is monitored over a 7 day time period.

As shown in FIG. 6, all animals that received the IgG control mAb-treated kidney die within 4 days. In contrast, survival is significantly increased in the animals that received the Clone1.1 treated kidney, with 30% of the animals surviving for the 7 day duration of the experiment.

Together, these experiments show that with both standard and extended criteria donor kidneys, Clone 1 and Clone 1.1 reduce IRI and increase kidney function and survival outcomes, respectively.

Example 7

Acute Promyelocytic Leukemia (APL) Anti-Tumor Activity In Vivo

The purpose of this experiment is to demonstrate that a humanized antibody clone disclosed herein, i.e., Clone 13, reduces tumor burden in vivo in a mouse leukemia model.

The anti-tumor activity of the anti-CD47mAb Clone13 (Cl 13; clone number as described above in Examples 2 and 3) is determined in a syngeneic murine model of Acute Promyelocytic Leukemia (APL) as described in Ramirez et al. (2009) *Blood* 113:6206-6214.

Murine APL cells (B6APL1) are injected intravenously into C57BL/6 mice that are randomized into three groups (5-10 mice per group): Group 1: no APL; Group 2: APL with no treatment; Group 3: APL with anti-CD47mAb Cl 13 treatment. Antibody treatment is initiated on the day of tumor inoculation (day 0), and given in single doses of 10 μg/dose (0.4 mg/kg) in phosphate buffered saline, pH 7.2, by intraperitoneal injection on days 0, 3, and 6.

Tumor burden is evaluated at day 25 following tumor cell inoculation. Blood samples from each mouse are analyzed for white blood cell count using an automated hemocytometer, and circulating APL cells (representing the tumor burden) are quantified by flow cytometry (CD34+/CD117+ cells).

As shown in FIG. 7, mice treated with C1 13 have reduced tumor burden compared to untreated mice at 25 days after tumor inoculation, thus demonstrating anti-tumor activity of this humanized clone.

Example 8

HepG2 Anti-Tumor Activity In Vivo

The purpose of this experiment is to demonstrate that a humanized antibody clone disclosed herein, i.e., Clone 1.1, reduces tumor burden in vivo in a mouse xenograft model of human hepatocellular carcinoma (HCC).

Male NSG mice are obtained from The Jackson Laboratory (Bar Harbor, Me.) and housed in cages in temperature and light-controlled environments with access to water and food ad libitum. For the heterotopic xenograft model, HepG2-luc2 cells (Perkin Elmer, Waltham, Mass. #134280) are suspended in DMEM containing 25% (v/v), and 1,000,000 cells implanted subcutaneously into the dorsal subcutaneous space of 4- to 8-wk-old NSG mice. After 2 weeks of growth, antibody treatment is begun with twice-weekly intraperitoneal injections of 15 mg/kg of either anti-CD47 antibody Clone 1.1 or an IgG control for 6 weeks. Tumor volumes are calculated twice weekly using (length×width)/0.6. After 6 weeks of treatment, animals are euthanized and tumors were resected, weighed, and fixed in 10% formalin.

As shown in FIG. 8, treatment with the CD47 mAb Clone 1.1 significantly reduced tumor growth of the HepG2 tumors ($p<0.01$), demonstrating anti-tumor efficacy on solid tumors.

Embodiments of the disclosure being thus described, it will be obvious that the same may be varied in many ways. Such variations are not to be regarded as a departure from the spirit and scope of the disclosure, and all such modifications as would be obvious to one skilled in the art are intended to be included within the scope of the following claims.

Amino Acid and Nucleic Acid Sequences

Light Chain Variable Region Amino Acid Sequences
Murine Sequence

```
>VxP037-01LC: Underlined amino acid sequences
represent CDRs
                                        (SEQ ID NO: 7)
DVVMTQTPLSLSVSLGDQASISCRSSQSLVHSNGNTYLHWYLQKPGQS

PKLLIYKVSYRFSGVPDRFSGSGSGTDFTLKISRVEAEDLGVYFCSQN

THVPRTFGQG
```

Humanized Light Chain Sequences

```
>pVxK7b-037-hum01-LC
                                        (SEQ ID NO: 8)
DIVMTQTPLSLPVTPGEPASISCRSSQSLVHSNGNTYLHWYQQKPGKA

PKLLIYKVSYRFSGVPDRFSGSGSGTDFTLKISRVEAEDVGVYYCSQN

THVPRTFGQG
```

-continued

```
>pVxK7b-037-hum02-LC
                                        (SEQ ID NO: 9)
DVVMTQSPLSLPVTLGQPASISCRSSQSLVHSNGNTYLHWYQQKPGQA

PRLLIYKVSYRFSGVPSRFSGSGSGTEFTLTISSLQPDDFATYYCSQN

THVPRTFGQG

>pVxK7b-037-hum03-LC
                                        (SEQ ID NO: 10)
DVVMTQSPLSLPVTLGQPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum04-LC
                                        (SEQ ID NO: 11)
DIQMTQSPSSLSASVGDRVTITCRSSQSLVHSNGNTYLHWYLQKPGQS

PQLLIYKVSYRFSGIPARFSGSGSGTEFTLTISSLQSEDFAVYYCSQN

THVPRTFGQG

>pVxK7b-037-hum05-LC
                                        (SEQ ID NO: 12)
DIVMTQTPLSLPVTPGEPASISCRSSQSLVHSNGNTYLHWYLQKPGQS

PQLLIYKVSYRFSGVPDRFSGSGSGTDFTLKISRVEAEDVGVYYCSQN

THVPRTFGQG

>pVxK7b-037-hum06-LC
                                        (SEQ ID NO: 13)
DIQMTQSPSSLSASVGDRVTITCRSSQSLVHSNGNTYLHWYLQKPGQS

PQLLIYKVSYRFSGIPARFSGSGSGTEFTLTISSLQSEDFAVYYCSQN

THVPRTFGQG

>pVxK7b-037-hum07-LC
                                        (SEQ ID NO: 14)
DIVMTQTPLSLPVTPGEPASISCRSSQSLVHSNGNTYLHWYLQKPGQS

PQLLIYKVSYRFSGVPDRFSGSGSGTDFTLKISRVEAEDVGVYYCSQN

THVPRTFGQG

>pVxK7b-037-hum08-LC
                                        (SEQ ID NO: 15)
DIVMTQTPLSLPVTPGEPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum09-LC
                                        (SEQ ID NO: 16)
DVVMTQSPLSLPVTLGQPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum10-LC
                                        (SEQ ID NO: 17)
DIVMTQTPLSLPVTPGEPASISCRSSQSLVHSNGNTYLHWYLQKPGQS

PQLLIYKVSYRFSGVPDRFSGSGSGTDFTLKISRVEAEDVGVYYCSQN

THVPRTFGQG

>pVxK7b-037-hum11-LC
                                        (SEQ ID NO: 18)
EIVLTQSPATLSVSPGERATLSCRSSQSLVHSNGNTYLHWYQQKPGQA

PRLLIYKVSYRFSGVPSRFSGSGSGTDFTFTISSLEAEDAATYYCSQN

THVPRTFGQG
```

>pVxK7b-037-hum12-LC
(SEQ ID NO: 19)
DIVMTQTPLSLPVTPGEPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum13-LC
(SEQ ID NO: 20)
DIVMTQTPLSLPVTPGEPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum14-LC
(SEQ ID NO: 21)
DVVMTQSPLSLPVTLGQPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum15-LC
(SEQ ID NO: 22)
AIQLTQSPSSLSASVGDRVTITCRSSQSLVHSNGNTYLHWYQQKPGQA

PRLLIYKVSYRFSGVPSRFSGSGSGTEFTLTISSLQPDDFATYYCSQN

THVPRTFGQG

>pVxK7b-037-hum16-LC
(SEQ ID NO: 23)
AIQLTQSPSSLSASVGDRVTITCRSSQSLVHSNGNTYLHWYQQKPGQA

PRLLIYKVSYRFSGVPDRFSGSGSGTDFTLKISRVEAEDVGVYYCSQN

THVPRTFGQG

>pVxK7b-037-hum17-LC
(SEQ ID NO: 24)
AIQLTQSPSSLSASVGDRVTITCRSSQSLVHSNGNTYLHWYQQKPGQA

PRLLIYKVSYRFSGVPDRFSGSGSGTDFTLKISRVEAEDVGVYYCSQN

THVPRTFGQG

>pVxK7b-037-hum18-LC
(SEQ ID NO: 25)
EIVLTQSPATLSVSPGERATLSCRSSQSLVHSNGNTYLHWYQQKPGQA

PRLLIYKVSYRFSGVPSRFSGSGSGTDFTFTISSLEAEDAATYYCSQN

THVPRTFGQG

>pVxK7b-037-hum19-LC
(SEQ ID NO: 26)
DVVMTQSPLSLPVTLGQPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum20-LC
(SEQ ID NO: 27)
DIVMTQTPLSLPVTPGEPASISCRSSQSLVHSNGNTYLHWYLQKPGQS

PQLLIYKVSYRFSGVPDRFSGSGSGTDFTLKISRVEAEDVGVYYCSQN

THVPRTFGQG

>pVxK7b-037-hum21-LC
(SEQ ID NO: 28)
AIQLTQSPSSLSASVGDRVTITCRSSQSLVHSNGNTYLHWYQQKPGQA

PRLLIYKVSYRFSGVPDRFSGSGSGTDFTLKISRVEAEDVGVYYCSQN

THVPRTFGQG

>pVxK7b-037-hum22-LC
(SEQ ID NO: 29)
EIVLTQSPATLSVSPGERATLSCRSSQSLVHSNGNTYLHWYQQKPGQA

PRLLIYKVSYRFSGVPSRFSGSGSGTDFTFTISSLEAEDAATYYCSQN

THVPRTFGQG

>pVxK7b-037-hum23-LC
(SEQ ID NO: 30)
DIVMTQTPLSLPVTPGEPASISCRSSQSLVHSNGNTYLHWYQQKPGKA

PKLLIYKVSYRFSGVPDRFSGSGSGTDFTLKISRVEAEDVGVYYCSQN

THVPRTFGQG

>pVxK7b-037-hum24-LC
(SEQ ID NO: 31)
AIQLTQSPSSLSASVGDRVTITCRSSQSLVHSNGNTYLHWYQQKPGQA

PRLLIYKVSYRFSGVPSRFSGSGSGTEFTLTISSLQPDDFATYYCSQN

THVPRTFGQG

Murine Light Chain Variable Region Nucleic Acid Sequence

>VxP037-01LC
(SEQ ID NO: 32)
GATGTTGTTATGACCCAAACTCCACTCTCCCTGTCTGTCAGTCTTGGA

GATCAAGCCTCCATCTCTTGCAGATCTAGTCAGAGCCTTGTACACAGT

AATGGAAACACCTATTTACATTGGTACCTGCAGAAGCCAGGCCAGTCT

CCAAAGCTCCTGATCTACAAAGTTTCCTACCGATTTTCTGGGGTCCCA

GACAGGTTCAGTGGCAGTGGATCAGGGACAGATTTCACACTCAAGATC

AGCAGAGTGGAGGCTGAGGATCTGGGAGTTTATTTCTGCTCTCAAAAT

ACACATGTTCCTCGGACGTTCGGCCAAGGAG

Humanized Light Chain Variable Region Nucleic Acid Sequences

>pVxK7b-037-hum01-LC
(SEQ ID NO: 33)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

-continued

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum02-LC (SEQ ID NO: 34)
GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCATCAAGGTTCAGCGGCAGTGGATCTGGGACAGAATTCACTCTCACCATC

AGCAGCCTGCAGCCTGATGATTTTGCAACTTATTACTGTTCTCAAAATACACATGTTCCT

CGGACGTTCGGCCAAGGG

>pVxK7b-037-hum03-LC (SEQ ID NO: 35)
GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum04-LC (SEQ ID NO: 36)
GACATCCAGATGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGATCCCAGCCAGGTTCAGTGGCAGTGGGTCTGGGACAGAGTTCACTCTCACCATC

AGCAGCCTGCAGTCTGAAGATTTTGCAGTTTATTACTGTTCTCAAAATACACATGTTCCT

CGGACGTTCGGCCAAGGG

>pVxK7b-037-hum05-LC (SEQ ID NO: 37)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum06-LC (SEQ ID NO: 38)
GACATCCAGATGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGATCCCAGCCAGGTTCAGTGGCAGTGGGTCTGGGACAGAGTTCACTCTCACCATC

AGCAGCCTGCAGTCTGAAGATTTTGCAGTTTATTACTGTTCTCAAAATACACATGTTCCT

CGGACGTTCGGCCAAGGG

>pVxK7b-037-hum07-LC (SEQ ID NO: 39)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

-continued

```
TACCTGCAGAAGCCAGGGCAGTCTCCACAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG
```

>pVxK7b-037-hum08-LC (SEQ ID NO: 40)
```
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG
```

>pVxK7b-037-hum09-LC (SEQ ID NO: 41)
```
GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG
```

>pVxK7b-037-hum10-LC (SEQ ID NO: 42)
```
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG
```

>pVxK7b-037-hum11-LC (SEQ ID NO: 43)
```
GAAATTGTGTTGACACAGTCTCCAGCCACCCTGTCTGTGTCTCCAGGGGAAAGAGCCACC

CTCTCCTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCCTCGAGGTTCAGTGGCAGTGGATCTGGGACAGATTTCACCTTTACCATC

AGTAGCCTGGAAGCTGAAGATGCTGCAACATATTACTGTTCTCAAAATACACATGTTCCT

CGGACGTTCGGCCAAGGG
```

>pVxK7b-037-hum12-LC (SEQ ID NO: 44)
```
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG
```

>pVxK7b-037-hum13-LC (SEQ ID NO: 45)

GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum14-LC (SEQ ID NO: 46)

GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum15-LC (SEQ ID NO: 47)

GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCATCAAGGTTCAGCGGCAGTGGATCTGGGACAGAATTCACTCTCACCATC

AGCAGCCTGCAGCCTGATGATTTTGCAACTTATTACTGTTCTCAAAATACACATGTTCCT

CGGACGTTCGGCCAAGGG

>pVxK7b-037-hum16-LC (SEQ ID NO: 48)

GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum17-LC (SEQ ID NO: 49)

GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum18-LC (SEQ ID NO: 50)

GAAATTGTGTTGACACAGTCTCCAGCCACCCTGTCTGTGTCTCCAGGGGAAAGAGCCACC

CTCTCCTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCCTCGAGGTTCAGTGGCAGTGGATCTGGGACAGATTTCACCTTTACCATC

```
-continued
AGTAGCCTGGAAGCTGAAGATGCTGCAACATATTACTGTTCTCAAAATACACATGTTCCT

CGGACGTTCGGCCAAGGG

>pVxK7b-037-hum19-LC
                                                    (SEQ ID NO: 51)
GATGTTGTGATGACTCAGTCTCCACTCTCCCTGCCCGTCACCCTTGGACAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum20-LC
                                                    (SEQ ID NO: 52)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TACCTGCAGAAGCCAGGGCAGTCTCCACAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum21-LC
                                                    (SEQ ID NO: 53)
GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum22-LC
                                                    (SEQ ID NO: 54)
GAAATTGTGTTGACACAGTCTCCAGCCACCCTGTCTGTGTCTCCAGGGGAAAGAGCCACC

CTCTCCTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT

TCTGGGGTCCCCTCGAGGTTCAGTGGCAGTGGATCTGGGACAGATTTCACCTTTACCATC

AGTAGCCTGGAAGCTGAAGATGCTGCAACATATTACTGTTCTCAAAATACACATGTTCCT

CGGACGTTCGGCCAAGGG

>pVxK7b-037-hum23-LC
                                                    (SEQ ID NO: 55)
GATATTGTGATGACCCAGACTCCACTCTCCCTGCCCGTCACCCCTGGAGAGCCGGCCTCC

ATCTCCTGCAGATCTAGTCAGAGCCTTGTACACAGTAATGGAAACACCTATTTACATTGG

TATCAGCAGAAACCAGGGAAAGCTCCTAAGCTCCTGATCTATAAAGTTTCCTACCGATTT

TCTGGGGTCCCAGACAGGTTCAGTGGCAGTGGGTCAGGCACTGATTTCACACTGAAAATC

AGCAGGGTGGAGGCTGAGGATGTTGGAGTTTATTACTGTTCTCAAAATACACATGTTCCT

CGGACGTTCGGCCAAGGG

>pVxK7b-037-hum24-LC
                                                    (SEQ ID NO: 56)
GCCATCCAGTTGACCCAGTCTCCATCCTCCCTGTCTGCATCTGTAGGAGACAGAGTCACC

ATCACTTGCAGATCTAGTCAGAGCCTTGTACACAGTAATGGAAACACCTATTTACATTGG

TACCAGCAGAAACCTGGCCAGGCTCCCAGGCTCCTCATCTATAAAGTTTCCTACCGATTT
```

-continued

```
TCTGGGGTCCCATCAAGGTTCAGCGGCAGTGGATCTGGGACAGAATTCACTCTCACCATC

AGCAGCCTGCAGCCTGATGATTTTGCAACTTATTACTGTTCTCAAAATACACATGTTCCT

CGGACGTTCGGCCAAGGG
```

Heavy Chain Variable Region Amino Acid Sequences

Murine Heavy Chain Variable Region Amino Acid Sequence: Underlined Amino Acid Sequences Indicate CDRs VxP037-01HC (SEQ ID NO: 57)

EVQLQQFGAELVKPGASMKLSCKAS<u>GYTFTNYYVF</u>WVKQRPGQGLEWI

G<u>DINPVNGDTNFNEKFKN</u>KATLTVDKSSTTTYLQLSSLTSEDSAVYYC

TR<u>GGYTMDY</u>WGQG

Humanized Heavy Chain Variable Region Amino Acid Sequences

>pVxK7b-037-hum01-HC (SEQ ID NO: 58)

QVQLQESGPGLVKPSQTLSLTCTVSGYTFTNYYVFWVRQARGQRLEWI

GDINPVNGDTNFNEKFKNRVTISADKSISTAYLQWSSLKASDTAMYYC

ARGGYTMDYWGQG

>pVxK7b-037-hum02-HC (SEQ ID NO: 59)

QVQLQESGPGLVKPSQTLSLTCTVSGYTFTNYYVFWVRQARGQRLEWI

GDINPVNGDTNFNEKFKNRVTISADKSISTAYLQWSSLKASDTAMYYC

ARGGYTMDYWGQG

>pVxK7b-037-hum03-HC (SEQ ID NO: 60)

EVQLVQSGAEVKKPGESLRISCKGSGYTFTNYYVFWVRQARGQRLEWI

GDINPVNGDTNFNEKFKNRVTITADKSTSTAYMELSSLRSEDTAVYYC

ARGGYTMDYWGQG

>pVxK7b-037-hum04-HC (SEQ ID NO: 61)

QVQLQESGPGLVKPSQTLSLTCTVSGYTFTNYYVFWVRQAPGKGLEWV

SDINPVNGDTNFNEKFKNRVTISVDTSKNQFSLKLSSVTAADTAVYYC

ARGGYTMDYWGQG

>pVxK7b-037-hum05-HC (SEQ ID NO: 62)

QVQLQESGPGLVKPSQTLSLTCTVSGYTFTNYYVFWVRQAPGKGLEWV

SDINPVNGDTNFNEKFKNRVTISVDTSKNQFSLKLSSVTAADTAVYYC

ARGGYTMDYWGQG

>pVxK7b-037-hum06-HC (SEQ ID NO: 63)

QVQLQESGPGLVKPSQTLSLTCTVSGYTFTNYYVFWVRQARGQRLEWI

GDINPVNGDTNFNEKFKNRLTISKDTSKNQVVLTMTNMDPVDTATYYC

ARGGYTMDYWGQG

>pVxK7b-037-hum07-HC (SEQ ID NO: 64)

QVQLQESGPGLVKPGATVKISCKVSGYTFTNYYVFWVRQARGQRLEWI

GDINPVNGDTNFNEKFKNRVTITADKSTSTAYMELSSLRSEDTAVYYC

ARGGYTMDYWGQG

>pVxK7b-037-hum08-HC (SEQ ID NO: 65)

QITLKESGPTLVKPTQTLTLTCTFSGYTFTNYYVFWIRQSPSRGLEWL

GDINPVNGDTNFNEKFKNRFTISRDNAKNSLYLQMNSLRAEDTAVYYC

ARGGYTMDYWGQG

>pVxK7b-037-hum09-HC (SEQ ID NO: 66)

QVQLQESGPGLVKPSQTLSLTCTVSGYTFTNYYVFWVRQARGQRLEWI

GDINPVNGDTNFNEKFKNRLTISKDTSKNQVVLTMTNMDPVDTATYYC

ARGGYTMDYWGQG

>pVxK7b-037-hum10-HC (SEQ ID NO: 67)

QVQLQESGPGLVKPSQTLSLTCTVSGYTFTNYYVFWVRQARGQRLEWI

GDINPVNGDTNFNEKFKNRLTISKDTSKNQVVLTMTNMDPVDTATYYC

ARGGYTMDYWGQG

>pVxK7b-037-hum11-HC (SEQ ID NO: 68)

QVQLQESGPGLVKPGATVKISCKVSGYTFTNYYVFWVRQARGQRLEWI

GDINPVNGDTNFNEKFKNRVTITADKSTSTAYMELSSLRSEDTAVYYC

ARGGYTMDYWGQG

>pVxK7b-037-hum12-HC (SEQ ID NO: 69)

QVQLQESGPGLVKPGATVKISCKVSGYTFTNYYVFWVRQARGQRLEWI

GDINPVNGDTNFNEKFKNRVTITADKSTSTAYMELSSLRSEDTAVYYC

ARGGYTMDYWGQG

>pVxK7b-037-hum13-HC (SEQ ID NO: 70)

EVQLVQSGAEVKKPGESLRISCKGSGYTFTNYYVFWIRQSPSRGLEWL

GDINPVNGDTNFNEKFKNRVTITADKSTSTAYMELSSLRSEDTAVYYC

ARGGYTMDYWGQG

>pVxK7b-037-hum14-HC (SEQ ID NO: 71)

QVQLQESGPGLVKPSQTLSLTCTVSGYTFTNYYVFWVRQARGQRLEWI

GDINPVNGDTNFNEKFKNRVTISADKSISTAYLQWSSLKASDTAMYYC

ARGGYTMDYWGQG

-continued

>pVxK7b-037-hum15-HC
(SEQ ID NO: 72)
QVQLQESGPGLVKPSQTLSLTCTVSGYTFTNYYVFWVRQARGQRLEWI

GDINPVNGDTNFNEKFKNRLTISKDTSKNQVVLTMTNMDPVDTATYYC

ARGGYTMDYWGQG

>pVxK7b-037-hum16-HC
(SEQ ID NO: 73)
QVQLQESGPGLVKPSQTLSLTCTVSGYTFTNYYVFWVRQARGQRLEWI

GDINPVNGDTNFNEKFKNRVTISADKSISTAYLQWSSLKASDTAMYYC

ARGGYTMDYWGQG

>pVxK7b-037-hum17-HC
(SEQ ID NO: 74)
EVQLVQSGAEVKKPGATVKISCKVSGYTFTNYYVFWIRQPPGKGLEWI

GDINPVNGDTNFNEKFKNRVTITADKSTSTAYMELSSLRSEDTAVYYC

ARGGYTMDYWGQG

>pVxK7b-037-hum18-HC
(SEQ ID NO: 75)
EVQLVQSGAEVKKPGESLRISCKGSGYTFTNYYVFWIRQSPSRGLEWL

GDINPVNGDTNFNEKFKNRVTITADKSTSTAYMELSSLRSEDTAVYYC

ARGGYTMDYWGQG

>pVxK7b-037-hum19-HC
(SEQ ID NO: 76)
EVQLVQSGAEVKKPGESLRISCKGSGYTFTNYYVFWIRQSPSRGLEWL

GDINPVNGDTNFNEKFKNRVTITADKSTSTAYMELSSLRSEDTAVYYC

ARGGYTMDYWGQG

>pVxK7b-037-hum20-HC
(SEQ ID NO: 77)
QITLKESGPTLVKPTQTLTLTCTFSGYTFTNYYVFWVRQAPGQGLEWM

GDINPVNGDTNFNEKFKNRVTITADKSTSTAYMELSSLRSEDTAVYYC

ARGGYTMDYWGQG

>pVxK7b-037-hum21-HC
(SEQ ID NO: 78)
QVQLQESGPGLVKPSQTLSLTCTVSGYTFTNYYVFWVRQARGQRLEWI

GDINPVNGDTNFNEKFKNRLTISKDTSKNQVVLTMTNMDPVDTATYYC

ARGGYTMDYWGQG

>pVxK7b-037-hum22-HC
(SEQ ID NO: 79)
QVQLQESGPGLVKPSQTLSLTCTVSGYTFTNYYVFWVRQARGQRLEWI

GDINPVNGDTNFNEKFKNRLTISKDTSKNQVVLTMTNMDPVDTATYYC

ARGGYTMDYWGQG

>pVxK7b-037-hum23-HC
(SEQ ID NO: 80)
QVQLQESGPGLVKPSQTLSLTCTVSGYTFTNYYVFWVRQARGQRLEWI

GDINPVNGDTNFNEKFKNRLTISKDTSKNQVVLTMTNMDPVDTATYYC

ARGGYTMDYWGQG

>pVxK7b-037-hum24-HC
(SEQ ID NO: 81)
QVQLQESGPGLVKPGATVKISCKVSGYTFTNYYVFWVRQARGQRLEWI

GDINPVNGDTNFNEKFKNRVTITADKSTSTAYMELSSLRSEDTAVYYC

ARGGYTMDYWGQG

Murine Heavy Chain Variable Region Nucleic Acid Sequence

>VxP037-01HC
(SEQ ID NO: 82)
GAGGTCCAGCTGCAGCAGTTTGGGGCTGAACTGGTGAAGCCTGGGGCT

TCAATGAAGTTGTCCTGCAAGGCTTCTGGCTACACCTTCACCAACTAC

TATGTATTCTGGGTGAAACAGAGGCCTGGACAAGGCCTTGAGTGGATT

GGAGACATTAATCCTGTCAATGGTGATACTAACTTCAATGAGAAATTC

AAGAACAAGGCCACACTGACTGTAGACAAGTCCTCCACCACAACATAC

TTGCAACTCAGCAGCCTGACATCTGAGGACTCTGCGGTCTATTACTGT

ACAAGAGGGGGTTATACTATGGACTACTGGGGTCAAGGA

Humanized Heavy Chain Variable Region Nucleic Acid Sequences

>pVxK7b-037-hum01-HC
(SEQ ID NO: 83)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum02-HC
(SEQ ID NO: 84)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

-continued

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum03-HC
(SEQ ID NO: 85)
GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum04-HC
(SEQ ID NO: 86)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTCCGCCAGGCT

CCAGGGAAGGGGCTGGAGTGGGTCAGTGACATTAATCCTGTCAATGGTGATACTAACTTC

AATGAGAAATTCAAGAACAGAGTCACCATATCAGTAGACACGTCCAAGAACCAGTTCTCC

CTGAAGCTGAGCTCTGTGACCGCCGCGGACACGGCTGTGTATTACTGTGCGAGAGGGGGT

TATACTATGGACTACTGGGGCCAGGGA

>pVxK7b-037-hum05-HC
(SEQ ID NO: 87)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTCCGCCAGGCT

CCAGGGAAGGGGCTGGAGTGGGTCAGTGACATTAATCCTGTCAATGGTGATACTAACTTC

AATGAGAAATTCAAGAACAGAGTCACCATATCAGTAGACACGTCCAAGAACCAGTTCTCC

CTGAAGCTGAGCTCTGTGACCGCCGCGGACACGGCTGTGTATTACTGTGCGAGAGGGGGT

TATACTATGGACTACTGGGGCCAGGGA

>pVxK7b-037-hum06-HC
(SEQ ID NO: 88)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum07-HC
(SEQ ID NO: 89)
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum08-HC
(SEQ ID NO: 90)
CAGATCACCTTGAAGGAGTCTGGTCCTACGCTGGTGAAACCCACACAGACCCTCACGCTG

ACCTGCACCTTCTCTGGCTACACCTTCACCAACTACTATGTATTCTGGATCAGGCAGTCC

-continued

CCATCGAGAGGCCTTGAGTGGCTGGGTGACATTAATCCTGTCAATGGTGATACTAACTTC

AATGAGAAATTCAAGAACAGATTCACCATCTCCAGAGACAACGCCAAGAACTCACTGTAT

CTGCAAATGAACAGCCTGAGAGCCGAGGACACGGCTGTGTATTACTGTGCGAGAGGGGGT

TATACTATGGACTACTGGGGCCAGGGA

>pVxK7b-037-hum09-HC  
(SEQ ID NO: 91)  
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum10-HC  
(SEQ ID NO: 92)  
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum11-HC  
(SEQ ID NO: 93)  
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum12-HC  
(SEQ ID NO: 94)  
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGT

TATACTATGGACTACTGGGGCCAGGGA

>pVxK7b-037-hum13-HC  
(SEQ ID NO: 95)  
GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGATCAGGCAGTCC

CCATCGAGAGGCCTTGAGTGGCTGGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum14-HC (SEQ ID NO: 96)

CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum15-HC (SEQ ID NO: 97)

CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum16-HC (SEQ ID NO: 98)

CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACCATCTCAGCCGACAAGTCCATCAGCACCGCCTAC

CTGCAGTGGAGCAGCCTGAAGGCCTCGGACACCGCCATGTATTACTGTGCGAGAGGGGGT

TATACTATGGACTACTGGGGCCAGGGA

>pVxK7b-037-hum17-HC (SEQ ID NO: 99)

GAGGTCCAGCTGGTACAGTCTGGGGCTGAGGTGAAGAAGCCTGGGGCTACAGTGAAAATC

TCCTGCAAGGTTTCTGGCTACACCTTCACCAACTACTATGTATTCTGGATCCGCCAGCCC

CCAGGGAAGGGGCTGGAGTGGATTGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGGT

TATACTATGGACTACTGGGGCCAGGGA

>pVxK7b-037-hum18-HC (SEQ ID NO: 100)

GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGATCAGGCAGTCC

CCATCGAGAGGCCTTGAGTGGCTGGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGT

TATACTATGGACTACTGGGGCCAGGGA

>pVxK7b-037-hum19-HC (SEQ ID NO: 101)

GAAGTGCAGCTGGTGCAGTCTGGAGCAGAGGTGAAAAAGCCCGGGGAGTCTCTGAGGATC

TCCTGTAAGGGTTCTGGCTACACCTTCACCAACTACTATGTATTCTGGATCAGGCAGTCC

CCATCGAGAGGCCTTGAGTGGCTGGGTGACATTAATCCTGTCAATGGTGATACTAACTTC

AATGAGAAATTCAAGAACAGAGTCACGATTACCGCGGACAAATCCACGAGCACAGCCTAC

```
ATGGAGCTGAGCAGCCTGAGATCTGAGGACACGGCCGTGTATTACTGTGCGAGAGGGGT

TATACTATGGACTACTGGGGCCAGGGA

>pVxK7b-037-hum20-HC
                                                   (SEQ ID NO: 102)
CAGATCACCTTGAAGGAGTCTGGTCCTACGCTGGTGAAACCCACACAGACCCTCACGCTG

ACCTGCACCTTCTCTGGCTACACCTTCACCAACTACTATGTATTCTGGGTGCGACAGGCC

CCTGGACAAGGGCTTGAGTGGATGGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGT

TATACTATGGACTACTGGGGCCAGGGA

>pVxK7b-037-hum21-HC
                                                   (SEQ ID NO: 103)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum22-HC
                                                   (SEQ ID NO: 104)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum23-HC
                                                   (SEQ ID NO: 105)
CAGGTGCAGCTGCAGGAGTCGGGCCCAGGACTGGTGAAGCCTTCACAGACCCTGTCCCTC

ACCTGCACTGTCTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGACTCACCATCTCCAAGGACACCTCCAAAAACCAGGTGGTC

CTTACAATGACCAACATGGACCCTGTGGACACAGCCACGTATTACTGTGCAAGAGGGGGT

TATACTATGGACTACTGGGGCCAGGGA

>pVxK7b-037-hum24-HC
                                                   (SEQ ID NO: 106)
CAGGTGCAGCTGCAGGAGTCGGGCCCAGGACTGGTGAAGCCTGGGGCTACAGTGAAAATC

TCCTGCAAGGTTTCTGGCTACACCTTCACCAACTACTATGTATTCTGGGTGCGACAGGCT

CGTGGACAACGCCTTGAGTGGATAGGTGACATTAATCCTGTCAATGGTGATACTAACTTC

AATGAGAAATTCAAGAACAGAGTCACGATTACCGCGGACAAATCCACGAGCACAGCCTAC

ATGGAGCTGAGCAGCCTGAGATCTGAGGACACGGCCGTGTATTACTGTGCGAGAGGGGT

TATACTATGGACTACTGGGGCCAGGGA
```

Chimeric Complete Light Chain Amino Acid Sequence

>VxP037-01-LC-Pro, below, represents a full length chimeric light chain variable domain (SEQ ID NO:7)+a constant domain amino acid sequence. The underlined amino acid sequence=framework 4+the constant domain. All full length humanized light chain sequences can contain a light chain variable region sequence selected from SEQ ID NOs: 7-31 in combination with framework 4+the same constant domain as VxP037-01-LC-Pro. However, while present, this constant domain is not shown for all the complete humanized light chain amino acid sequences.

>VxP037-01-LC-Pro
(SEQ ID NO: 107)
DVVMTQTPLSLSVSLGDQASISCRSSQSLVHSNGNTYLHWYLQKPGQSP

KLLIYKVSYRFSGVPDRFSGSGSGTDFTLKISRVEAEDLGVYFCSQNTH

VPRTFGQGTKVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

Chimeric Complete Light Chain Nucleic Acid Sequence

The underlined nucleic acid sequence encodes the underlined protein sequence in >VxP037-01-LC-Pro, above.

>VxP037-01-LC-DNA
(SEQ ID NO: 108)
GATGTTGTTATGACCCAAACTCCACTCTCCCTGTCTGTCAGTCTTGGAG

ATCAAGCCTCCATCTCTTGCAGATCTAGTCAGAGCCTTGTACACAGTAA

TGGAAACACCTATTTACATTGGTACCTGCAGAAGCCAGGCCAGTCTCCA

AAGCTCCTGATCTACAAAGTTTCCTACCGATTTTCTGGGGTCCCAGACA

GGTTCAGTGGCAGTGGATCAGGGACAGATTTCACACTCAAGATCAGCAG

AGTGGAGGCTGAGGATCTGGGAGTTTATTTCTGCTCTCAAAATACACAT

GTTCCTCGGACGTTCGGCCAAGGGACCAAGGTGGAAATCAAACGTACGG

TGGCTGCACCATCTGTCTTCATCTTCCCGCCATCTGATGAGCAGTTGAA

ATCTGGAACTGCCTCTGTTGTGTGCCTGCTGAATAACTTCTATCCCAGA

GAGGCCAAAGTACAGTGGAAGGTGGATAACGCCCTCCAATCGGGTAACT

CCCAGGAGAGTGTCACAGAGCAGGACAGCAAGGACAGCACCTACAGCCT

CAGCAGCACCCTGACGCTGAGCAAAGCAGACTACGAGAAACACAAAGTC

TACGCCTGCGAAGTCACCCATCAGGGCCTGAGCTCGCCCGTCACAAAGA

GCTTCAACAGGGGAGAGTGTTGA

Chimeric and Humanized Complete Heavy Chain Amino Acid Sequences

>VxP037-01-HC-Pro, below, represents a full length chimeric heavy chain variable domain (SEQ ID NO:57)+a constant domain amino acid sequence. The underlined amino acid sequence=framework 4+the constant IgG1 domain. All full length humanized heavy chain sequences can contain a heavy chain variable region sequence selected from SEQ ID NOs:57-81 in combination with framework 4+the same constant domain as VxP037-01-HC-Pro. However, while present, this constant domain is not shown for all the complete humanized heavy chain amino acid sequences.

Chimeric Complete Heavy Chain Amino Acid Sequence

>VxP037-01-HC-Pro
(SEQ ID NO: 109)
EVQLQQFGAELVKPGASMKLSCKASGYTFTNYYVFWVKQRPGQGLEWIG

DINPVNGDTNFNEKFKNKATLTVDKSSTTTYLQLSSLTSEDSAVYYCTR

GGYTMDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK

Chimeric Complete Heavy Chain Nucleic Acid Sequence

The underlined nucleic acid sequence encodes the underlined protein sequence in >VxP037-01-HC-Pro, above.

>VxP037-01-HC-DNA
(SEQ ID NO: 110)
GAGGTCCAGCTGCAGCAGTTTGGGGCTGAACTGGTGAAGCCTGGGGCTT

CAATGAAGTTGTCCTGCAAGGCTTCTGGCTACACCTTCACCAACTACTA

TGTATTCTGGGTGAAACAGAGGCCTGGACAAGGCCTTGAGTGGATTGGA

GACATTAATCCTGTCAATGGTGATACTAACTTCAATGAGAAATTCAAGA

ACAAGGCCACACTGACTGTAGACAAGTCCTCCACCACAACATACTTGCA

ACTCAGCAGCCTGACATCTGAGGACTCTGCGGTCTATTACTGTACAAGA

GGGGGTTATACTATGGACTACTGGGGCCAGGGACGCTGGTCACCGTCA

GCTCAGCCTCCACCAAGGGCCCATCGGTCTTCCCCCTGGCACCCTCCTC

CAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCA

GCGGCGTGCACACCTTCCCGGCTGTCCTACAGTCCTCAGGACTCTACTC

CCTCAGCAGCGTGGTGACCGTGCCCTCCAGCAGCTTGGGCACCCAGACC

TACATCTGCAACGTGAATCACAAGCCCAGCAACACCAAGGTGGACAAGA

AAGTTGAGCCCAAATCTTGTGACAAAACTCACACATGCCCACCGTGCCC

AGCACCTGAACTCCTGGGGGGACCGTCAGTCTTCCTCTTCCCCCCAAAA

CCCAAGGACACCCTCATGATCTCCCGGACCCCTGAGGTCACATGCGTGG

TGGTGGACGTGAGCCACGAAGACCCTGAGGTCAAGTTCAACTGGTACGT

GGACGGCGTGGAGGTGCATAATGCCAAGACAAAGCCGCGGGAGGAGCAG

TACAACAGCACGTACCGTGTGGTCAGCGTCCTCACCGTCCTGCACCAGG

ACTGGCTGAATGGCAAGGAGTACAAGTGCAAGGTCAGCAACAAAGCCCT

CCCAGCCCCCATCGAGAAAACCATCTCCAAAGCCAAAGGGCAGCCCCGA

GAACCACAGGTGTACACCCTGCCCCCATCCCGGGATGAGCTGACCAAGA

ACCAGGTCAGCCTGACCTGCCTGGTCAAAGGCTTCTATCCCAGCGACAT

CGCCGTGGAGTGGGAGAGCAATGGGCAGCCGGAGAACAACTACAAGACC

ACGCCTCCCGTGCTGGACTCCGACGGCTCCTTCTTCCTCTACAGCAAGC

TCACCGTGGACAAGAGCAGGTGGCAGCAGGGGAACGTCTTCTCATGCTC

CGTGATGCATGAGGCTCTGCACAACCACTACACGCAGAAGAGCCTCTCC

CTGTCTCCGGGTAAATGA

Complete IgG1 N2970, IgG2, and IgG4 S228P Heavy Chain Amino Acid Sequences

>VxP037-01-HC-IgG1 N297Q-Pro, below, represents a full length heavy chain variable domain (SEQ ID NO:57)+a constant domain amino acid sequence. The underlined amino acid sequence=framework 4+the constant IgG1 constant domain containing a N Q mutation at amino acid position 297. All full length humanized heavy chain sequences can contain a heavy chain variable region sequence selected from SEQ ID NOs:57-81 in combination with framework 4+the same constant domain as >VxP037-01-HC-IgG1 N297Q-Pro. However, while present, this constant domain is not shown for all the complete humanized heavy chain amino acid sequences.

>VxP037-01-HC-IgG1 N297Q-Pro
(SEQ ID NO: 111)
EVQLQQFGAELVKPGASMKLSCKASGYTFTNYYVFWVKQRPGQGLEWIG

DINPVNGDTNFNEKFKNKATLTVDKSSTTTYLQLSSLTSEDSAVYYCTR

GGYTMDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YQSTYRVVSVLTVLHQDWLNGKEYKCKVSNKALPAPIEKTISKAKGQPR

EPQVYTLPPSR

>pVxK7b-037-hum01-HC-IgG2-Pro, below, represents a full length heavy chain variable domain (SEQ ID NO:58)+a constant domain amino acid sequence. The underlined amino acid sequence=framework 4+the constant IgG2 domain. All full length humanized heavy chain sequences can contain a heavy chain variable region sequence selected from SEQ ID NOs:57-81 in combination with framework 4+the same constant domain as >pVxK7b-037-hum01-HC-IgG2-Pro. However, while present, this constant domain is not shown for all the complete humanized heavy chain amino acid sequences.

> pVxK7b-037-hum01-HC-IgG2-Pro
(SEQ ID NO: 112)
QVQLQESGPGLVKPSQTLSLTCTVSGYTFTNYYVFWVRQARGQRLEWI

GDINPVNGDTNFNEKFKNRVTISADKSISTAYLQWSSLKASDTAMYYC

ARGGYTMDYWGQGTLVTVSSASTKGPSVFPLAPCSRSTSESTAALGCL

VKDYFPEPVTVSWNSGALTSGVHTFPAVLQSSGLYSLSSVVTVPSSNF

GTQTYTCNVDHKPSNTKVDKTVERKCCVECPPCPAPPVAGPSVFLFPP

KPKDTLMISRTPEVTCVVVDVSHEDPEVQFNWYVDGVEVHNAKTKPRE

EQFNSTFRVVSVLTVVHQDWLNGKEYKCKVSNKGLPAPIEKTISKTKG

QPREPQVYTLPPSREEMTKNQVSLTCLVKGFYPSDIAVEWESNGQPEN

NYNTTPPMLDSDGSFFLYSKLTVDKSRWQQGNVFSCSVMHEALHNHYT

QKSLSLSPGK

>pVxK7b-037-hum01-HC-IgG4 S228P-Pro, below, represents a full length heavy chain variable domain (SEQ ID NO:58)+a constant domain amino acid sequence. The underlined amino acid sequence=framework 4+the constant IgG4 S228P domain. All full length humanized heavy chain sequences can contain a heavy chain variable region sequence selected from SEQ ID NOs:57-81 in combination with framework 4+the same constant domain as >pVxK7b-037-hum01-HC-IgG4 S228P-Pro. However, while present, this constant domain is not shown for all the complete humanized heavy chain amino acid sequences.

> pVxK7b-037-hum01-HC-IgG4 S228P-Pro
(SEQ ID NO: 113)
QVQLQESGPGLVKPSQTLSLTCTVSGYTFTNYYVFWVRQARGQRLEWIG

DINPVNGDTNFNEKFKNRVTISADKSISTAYLQWSSLKASDTAMYYCAR

GGYTMDYWGQGTTVTVSSASTKGPSVFPLAPCSRSTSESTAALGCLVKD

YFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNS

TYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPP

VLDSDGSFFLYSRLTVDKSRWQEGNVFSCSVMHEALHNHYTQKSLSLSL

GK

Complete IgG1 N2970, IgG2, and IgG4 S228P Heavy Chain Nucleic Acid Sequences

The underlined nucleic acid sequence encodes the underlined protein sequence in >VxP037-01-HC-IgG1 N297Q-Pro, above.

>VxP037-01-HC-IgG1 N297Q-DNA
(SEQ ID NO: 114)
GAGGTCCAGCTGCAGCAGTTTGGGGCTGAACTGGTGAAGCCTGGGGCTT

CAATGAAGTTGTCCTGCAAGGCTTCTGGCTACACCTTCACCAACTACTA

TGTATTCTGGGTGAAACAGAGGCCTGGACAAGGCCTTGAGTGGATTGGA

GACATTAATCCTGTCAATGGTGATACTAACTTCAATGAGAAATTCAAGA

ACAAGGCCACACTGACTGTAGACAAGTCCTCCACCACAACATACTTGCA

ACTCAGCAGCCTGACATCTGAGGACTCTGCGGTCTATTACTGTACAAGA

GGGGGTTATACTATGGACTACTGGGGCCAGGGAACGCTGGTCACCGTCA

GCTCAGCCTCCACCAAGGGCCCATCGGTCTTCCCCCTGGCACCCTCCTC

CAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCA

GCGGCGTGCACACCTTCCCGGCTGTCCTACAGTCCTCAGGACTCTACTC

CCTCAGCAGCGTGGTGACCGTGCCCTCCAGCAGCTTGGGCACCCAGACC

TACATCTGCAACGTGAATCACAAGCCCAGCAACACCAAGGTGGACAAGA

AAGTTGAGCCCAAATCTTGTGACAAAACTCACACATGCCCACCGTGCCC

-continued

AGCACCTGAACTCCTGGGGGGACCGTCAGTCTTCCTCTTCCCCCCAAAA

CCCAAGGACACCCTCATGATCTCCCGGACCCCTGAGGTCACATGCGTGG

TGGTGGACGTGAGCCACGAAGACCCTGAGGTCAAGTTCAACTGGTACGT

GGACGGCGTGGAGGTGCATAATGCCAAGACAAAGCCGCGGGAGGAGCAG

TACCAGAGCACGTACCGTGTGGTCAGCGTCCTCACCGTCCTGCACCAGG

ACTGGCTGAATGGCAAGGAGTACAAGTGCAAGGTCAGCAACAAAGCCCT

CCCAGCCCCATCGAGAAAACCATCTCCAAAGCCAAAGGGCAGCCCCGA

GAACCACAGGTGTACACCCTGCCCCCATCCCGGGATGAGCTGACCAAGA

ACCAGGTCAGCCTGACCTGCCTGGTCAAAGGCTTCTATCCCAGCGACAT

CGCCGTGGAGTGGGAGAGCAATGGGCAGCCGGAGAACAACTACAAGACC

ACGCCTCCCGTGCTGGACTCCGACGGCTCCTTCTTCCTCTACAGCAAGC

TCACCGTGGACAAGAGCAGGTGGCAGCAGGGGAACGTCTTCTCATGCTC

CGTGATGCATGAGGCTCTGCACAACCACTACACGCAGAAGAGCCTCTCC

CTGTCTCCGGGTAAATGA

The underlined nucleic acid sequence encodes the underlined protein sequence in >VxP037-hum 01-HC-IgG2-Pro, above.

```
> pVxK7b-037-hum01-HC-IgG2-Pro-DNA
                                (SEQ ID NO: 115)
```
CAGGTGCAGCTGCAGGAGTCGGGCCCAGGACTGGTGAAGCCTTCACAGA

CCCTGTCCCTCACCTGCACTGTCTCTGGCTACACCTTCACCAACTACTA

TGTATTCTGGGTGCGACAGGCTCGTGGACAACGCCTTGAGTGGATAGGT

GACATTAATCCTGTCAATGGTGATACTAACTTCAATGAGAAATTCAAGA

ACAGAGTCACCATCTCAGCCGACAAGTCCATCAGCACCGCCTACCTGCA

GTGGAGCAGCCTGAAGGCCTCGGACACCGCCATGTATTACTGTGCGAGA

GGGGGTTATACTATGGACTACTGGGGCCAGGGAACGCTGGTCACCGTCA

GCTCAGCCTCCACCAAGGGCCCATCGGTCTTCCCCCTGGCACCCTGCTC

CAGGAGCACCTCCGAGAGCACAGCGGCCCTGGGCTGCCTGGTCAAGGAC

TACTTCCCCGAACCGGTGACGGTGTCGTGGAACTCAGGCGCTCTGACCA

GCGGCGTGCACACCTTCCCGGCTGTCCTACAGTCCTCAGGACTCTACTC

CCTCAGCAGCGTGGTGACCGTGCCCTCCAGCAACTTCGGCACCCAGACC

TACACCTGCAACGTAGATCACAAGCCCAGCAACACCAAGGTGGACAAGA

CAGTTGAGCGCAAATGTTGTGTCGAGTGCCCACCGTGCCCAGCACCACC

TGTGGCAGGACCGTCAGTCTTCCTCTTCCCCCAAAACCCAAGGACACC

CTCATGATCTCCCGGACCCCTGAGGTCACGTGCGTGGTGGTGGACGTGA

GCCACGAAGACCCCGAGGTCCAGTTCAACTGGTACGTGGACGGCGTGGA

GGTGCATAATGCCAAGACAAAGCCACGGGAGGAGCAGTTCAACAGCACG

TTCCGTGTGGTCAGCGTCCTCACCGTCGTGCACCAGGACTGGCTGAACG

GCAAGGAGTACAAGTGCAAGGTGTCCAACAAAGGCCTCCCAGCCCCCAT

CGAGAAAACCATCTCCAAAACCAAAGGGCAGCCCCGAGAACCACAGGTG

TACACCCTGCCCCCATCCCGGGAGGAGATGACCAAGAACCAGGTCAGCC

TGACCTGCCTGGTCAAAGGCTTCTACCCCAGCGACATCGCCGTGGAGTG

GGAGAGCAATGGGCAGCCGGAGAACAACTACAACACCACACCTCCCATG

CTGGACTCCGACGGCTCCTTCTTCCTCTACAGCAAGCTCACCGTGGACA

AGAGCAGGTGGCAGCAGGGGAACGTCTTCTCATGCTCCGTGATGCATGA

GGCTCTGCACAACCACTACACGCAGAAGAGCCTCTCCCTGTCTCCGGGT

AAA

The underlined nucleic acid sequence encodes the underlined protein sequence in >VxP037-hum 01-HC-IgG4 S228P Pro, above.

```
> pVxK7b-037-hum01-HC-IgG4 S228P-Pro
                                (SEQ ID NO: 116)
```
CAGGTGCAGCTGCAGGAGTCGGGCCCAGGACTGGTGAAGCCTTCACAGA

CCCTGTCCCTCACCTGCACTGTCTCTGGCTACACCTTCACCAACTACTA

TGTATTCTGGGTGCGACAGGCTCGTGGACAACGCCTTGAGTGGATAGGT

GACATTAATCCTGTCAATGGTGATACTAACTTCAATGAGAAATTCAAGA

ACAGAGTCACCATCTCAGCCGACAAGTCCATCAGCACCGCCTACCTGCA

GTGGAGCAGCCTGAAGGCCTCGGACACCGCCATGTATTACTGTGCGAGA

GGGGGTTATACTATGGACTACTGGGGCCAGGGACCACCGTGACCGTGT

CCTCCGCTTCCACCAAGGGCCCATCCGTCTTCCCCCTGGCGCCCTGCTC

CAGGAGCACCTCCGAGAGCACAGCCGCCCTGGGCTGCCTGGTCAAGGAC

TACTTCCCCGAACCGGTGACGGTGTCGTGGAACTCAGGCGCCCTGACCA

GCGGCGTGCACACCTTCCCGGCTGTCCTACAGTCCTCAGGACTCTACTC

CCTCAGCAGCGTGGTGACCGTGCCCTCCAGCAGCTTGGGCACGAAGACC

TACACCTGCAACGTAGATCACAAGCCCAGCAACACCAAGGTGGACAAGA

GAGTTGAGTCCAAATATGGTCCCCCATGCCCACCGTGCCCAGCACCTGA

GTTCCTGGGGGGACCATCAGTCTTCCTGTTCCCCCCAAAACCCAAGGAC

ACTCTCATGATCTCCCGGACCCCTGAGGTCACGTGCGTGGTGGTGGACG

TGAGCCAGGAAGACCCCGAGGTCCAGTTCAACTGGTACGTGGATGGCGT

GGAGGTGCATAATGCCAAGACAAAGCCGCGGGAGGAGCAGTTCAACAGC

ACGTACCGTGTGGTCAGCGTCCTCACCGTCCTGCACCAGGACTGGCTGA

ACGGCAAGGAGTACAAGTGCAAGGTGTCCAACAAAGGCCTCCCGTCCTC

CATCGAGAAAACCATCTCCAAAGCCAAAGGGCAGCCCCGAGAGCCACAG

GTGTACACCCTGCCCCCATCCCAGGAGGAGATGACCAAGAACCAGGTCA

GCCTGACCTGCCTGGTCAAAGGCTTCTACCCCAGCGACATCGCCGTGGA

GTGGGAGAGCAATGGGCAGCCGGAGAACAACTACAAGACCACGCCTCCC

GTGCTGGACTCCGACGGCTCCTTCTTCCTCTACAGCAGGCTAACCGTGG

ACAAGAGCAGGTGGCAGGAGGGGAATGTCTTCTCATGCTCCGTGATGCA

TGAGGCTCTGCACAACCACTACACACAGAAGAGCCTCTCCCTGTCTCTG

GGTAAA

Framework 4+Light Chain Constant Domain Amino Acid Sequence (SEQ ID NO: 117)
TKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQ

GLSSPVTKSFNRGEC

Framework 4+Heavy Chain Constant IgG1 Domain (SEQ ID NO: 118)
TLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSN

TKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSF

FLYSKLTVDKSRWQQGNVFSCSVMHEALHNHYTQKSLSLSPGK

Framework 4+Heavy Chain Constant IgG1 N297Q Domain (SEQ ID NO: 119)
TLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSN

TKVDKKVEPKSCDKTHTCPPCPAPELLGGPSVFLFPPKPKDTLMISRTP

EVTCVVVDVSHEDPEVKFNWYVDGVEVHNAKTKPREEQYQSTYRVVSVL

TVLHQDWLNGKEYKCKVSNKALPAPIEKTISKAKGQPREPQVYTLPPSR

Framework 4+Heavy Chain Constant IgG2 Domain (SEQ ID NO: 120)
WGQGTLVTVSSASTKGPSVFPLAPCSRSTSESTAALGCLVKDYFPEPVT

VSWNSGALTSGVHTFPAVLQSSGLYSLSSVVTVPSSNFGTQTYTCNVDH

KPSNTKVDKTVERKCCVECPPCPAPPVAGPSVFLFPPKPKDTLMISRTP

EVTCVVVDVSHEDPEVQFNWYVDGVEVHNAKTKPREEQFNSTFRVVSVL

TVVHQDWLNGKEYKCKVSNKGLPAPIEKTISKTKGQPREPQVYTLPPSR

EEMTKNQVSLTCLVKGFYPSDIAVEWESNGQPENNYNTTPPMLDSDGSF

FLYSKLTVDKSRWQQGNVFSCSVMHEALHNHYTQKSLSLSPGK

Framework 4+Heavy Chain Constant IgG4 S228P Domain (SEQ ID NO: 121)
TTVTVSSASTKGPSVFPLAPCSRSTSESTAALGCLVKDYFPEPVTVSWN

SGALTSGVHTFPAVLQSSGLYSLSSVVTVPSSSLGTKTYTCNVDHKPSN

TKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLY

SRLTVDKSRWQEGNVFSCSVMHEALHNHYTQKSLSLSLGK

---

What is claimed is:

1. A monoclonal antibody, or antigen-binding fragment thereof, that specifically binds CD47, wherein the monoclonal antibody, or antigen-binding fragment thereof, comprises three light chain complementarity determining regions (LCDRs 1-3) and three heavy chain complementarity determining regions (HCDRs 1-3), wherein:
   LCDR1 comprises the amino acid sequence RSSQSLVHSNGNTYLH (SEQ ID NO:1);
   LCDR2 comprises the amino acid sequence KVSYRFS (SEQ ID NO:2); and
   LCDR3 comprises the amino acid sequence SQNTHVPRT (SEQ ID NO:3);
   HCDR1 comprises the amino acid sequence GYTFTNYYVF (SEQ ID NO:4);
   HCDR2 comprises the amino acid sequence DINPVNGDTNFNEKFKN (SEQ ID NO:5); and
   HCDR3 comprises the amino acid sequence GGYTMDY (SEQ ID NO:6); and
   wherein the monoclonal antibody, or antigen-binding fragment thereof, further comprises a light chain constant domain of SEQ ID NO: 117; and
   wherein the monoclonal antibody, or antigen-binding fragment thereof, further comprises a heavy chain constant domain selected from among SEQ ID NO:118, SEQ ID NO:119, SEQ ID NO:120, and SEQ ID NO:121.

2. The monoclonal antibody, or antigen-binding fragment thereof of claim 1, which is chimeric or humanized.

3. The monoclonal antibody, or antigen-binding fragment thereof of claim 1, which specifically binds human, rat, mouse, and pig CD47.

4. The monoclonal antibody, or antigen-binding fragment thereof of claim 1, which comprises a light chain variable region (LCVR) and a heavy chain variable region (HCVR), wherein said LCVR and said HCVR comprise, respectively, amino acid sequences selected from among the following combinations of LCVRs and HCVRs:
   SEQ ID NO:7 and SEQ ID NO:57;
   SEQ ID NO:8 and SEQ ID NO:58;
   SEQ ID NO:9 and SEQ ID NO:59;
   SEQ ID NO:10 and SEQ ID NO:60;
   SEQ ID NO:11 and SEQ ID NO:61;
   SEQ ID NO:12 and SEQ ID NO:62;
   SEQ ID NO:13 and SEQ ID NO:63;
   SEQ ID NO:14 and SEQ ID NO:64;
   SEQ ID NO:15 and SEQ ID NO:65;
   SEQ ID NO:16 and SEQ ID NO:66;
   SEQ ID NO:17 and SEQ ID NO:67;
   SEQ ID NO:18 and SEQ ID NO:68;
   SEQ ID NO:19 and SEQ ID NO:69;
   SEQ ID NO:20 and SEQ ID NO:70;
   SEQ ID NO:21 and SEQ ID NO:71;
   SEQ ID NO:22 and SEQ ID NO:72;
   SEQ ID NO:23 and SEQ ID NO:73;
   SEQ ID NO:24 and SEQ ID NO:74;
   SEQ ID NO:25 and SEQ ID NO:75;
   SEQ ID NO:26 and SEQ ID NO:76;
   SEQ ID NO:27 and SEQ ID NO:77;
   SEQ ID NO:28 and SEQ ID NO:78;
   SEQ ID NO:29 and SEQ ID NO:79;
   SEQ ID NO:30 and SEQ ID NO:80; and
   SEQ ID NO:31 and SEQ ID NO:81.

\* \* \* \* \*